United States Patent [19]

Wakatsuka et al.

[11] 4,367,237
[45] Jan. 4, 1983

[54] PROSTACYCLIN ANALOGUES

[75] Inventors: Hirohisa Wakatsuka; Katsuichi Shimoji, both of Takatsuki; Sadahiko Iguchi, Otsu; Yoshitaka Konishi; Hisashi Suga, both of Takatsuki; Yasuyuki Miyata, Kyoto; Yoichi Iguchi, Kusatsu; Hajimu Miyake; Masaki Hayashi, both of Takatsuki, all of Japan

[73] Assignee: Ono Pharmaceutical Co., Ltd., Japan

[21] Appl. No.: 97,675

[22] Filed: Nov. 27, 1979

[30] Foreign Application Priority Data

Nov. 26, 1978 [JP] Japan ................................. 53-159207
Nov. 29, 1978 [JP] Japan ................................. 53-147637

[51] Int. Cl.³ ..................... A61K 31/38; C07D 333/78
[52] U.S. Cl. .................... 424/275; 260/330.3; 424/180; 424/248.51; 424/250; 424/263; 424/267; 424/274; 536/103; 542/426; 542/429; 544/145; 544/376; 546/202; 546/274; 549/23; 549/51; 549/53; 549/58; 548/525
[58] Field of Search ..................... 549/13, 29, 51, 53, 549/58; 542/421, 426, 429; 424/275, 278, 285, 180, 248.51, 250, 263, 267, 274; 536/103

[56] References Cited

U.S. PATENT DOCUMENTS

| | | | |
|---|---|---|---|
| 4,150,222 | 4/1979 | Johnson | 542/426 |
| 4,158,667 | 6/1979 | Axen | 542/426 X |
| 4,178,367 | 12/1979 | Masaki et al. | 424/285 |
| 4,180,512 | 12/1979 | Smith | 260/345.2 |
| 4,187,381 | 2/1980 | Holland et al. | 560/121 |
| 4,208,428 | 6/1980 | Kurono et al. | 542/426 X |
| 4,258,199 | 3/1981 | Nicolaou et al. | 549/51 |
| 4,271,184 | 6/1981 | Gandolfi et al. | 424/285 |
| 4,291,166 | 9/1981 | Nicolaou et al. | 549/51 |

OTHER PUBLICATIONS

Nicolaou et al, J. Chem. Soc. Chem. Comm. 1978, pp. 375 to 377.
Nicolaou et al, J. Am. Chem. Soc. vol. 100, pp. 2567 to 2570 (4-12-78).
Gryglewski et al, Experientia vol. 34, pp. 1336 to 1338 (10-15-78).
Shibasaki et al, Tetrahedron Letters, No. 6, pp. 559–562 (Jun. 1978).
Horii et al, Eur. J. Pharmacol. 1978, pp. 313–316, vol. 51, No. 3.
Shimoji et al, Chem. Lett. 1978 (12), 1375–1376.
Derwent of Japanese 130,665 (5-29-79).

Primary Examiner—Richard Raymond
Attorney, Agent, or Firm—Stevens, Davis, Miller & Mosher

[57] ABSTRACT

Prostaglandin analogues of the general formula:

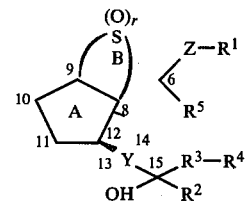

[wherein the ring A represents:

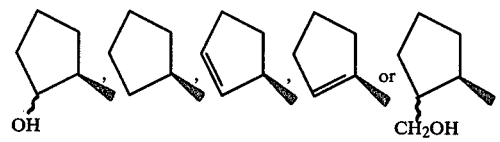

the ring B represents:

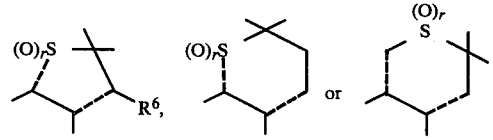

(wherein $R^6$ represents hydrogen, methyl or ethyl, and r is zero, one or two), Y represents ethylene, cis- or trans-vinylene or ethynylene, Z represents a grouping of the formula: $-(CH_2)_m-$, $-(CH_2)_3-CHR^7-$, $-(CH_2)_2-CHR^7-CH_2-$, $-CH_2-CHR^7-(CH_2)_2-$, $-CHR^7-(CH_2)_3-$, or trans-$(CH_2)_2-CH=CH-$ (wherein m is 3, 4 or 5, and $R^7$ represents methyl or ethyl), $R^1$ represents a grouping of the formula: $-COOR^8$,

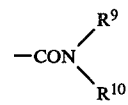

or $-CH_2OR^{11}$ (wherein $R^8$ represents hydrogen, alkyl, aralkyl, cycloalkyl which is unsubstituted or substituted by at least one alkyl group, or $R^8$ represents phenyl which is unsubstituted or substituted by halogen, trifluoromethyl, alkyl, alkoxy, alkylthio or phenyl, or represents naphthyl, 2,3- or 1,3-dihydroxypropyl, 2,3- or 1,3-bisalkanoyloxypropyl, a grouping of the formula: -$D_1$-COOR¹²,

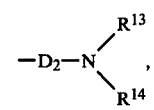

-$D_2$-$R^{15}$ or -$D_3$-$R^{16}$, wherein $D_1$ represents alkylene, $D_2$ represents alkylene, $D_3$ represents a single bond or alkylene, $R^{12}$, $R^{13}$ and $R^{14}$, each represent alkyl, $R^{15}$ represents hydroxy, alkoxy or alkylthio and $R^{16}$ represents a heterocyclic ring, or $R^8$ represents a grouping of the formula:

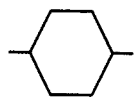

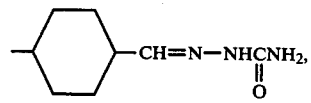

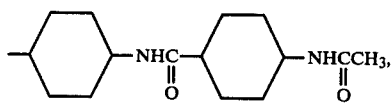

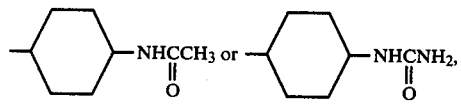

$R^9$ and $R^{10}$, each represent hydrogen, alkyl, alkylsulphonyl, alkanoyl or

represents a heterocyclic ring, and $R^{11}$ represents hydrogen or alkanoyl, $R^2$ represents hydrogen, methyl or ethyl, $R^3$ represents a single bond or alkylene, $R^4$ represents hydrogen, alkyl, alkoxy, cycloalkyl or cycloalkyloxy unsubstituted or substituted by alkyl, or represents phenyl or phenoxy unsubstituted or substituted by halogen, trifluoromethyl or alkyl with the proviso that, when $R^3$ represents a single bond, $R^4$ does not represent alkoxy, cycloalkyloxy or phenoxy, $R^5$ represents hydrogen, methyl or ethyl and with the proviso that, when one of the groups $R^5$, $R^6$ and $R^7$ represents methyl or ethyl the other two groups are hydrogen atoms] and cyclodextrin clathrates, non-toxic salts and non-toxic acid addition salts thereof, possess selective strong stimulatory activity on uterine contraction in female mammals.

9 Claims, No Drawings

PROSTACYCLIN ANALOGUES

This invention relates to new thioprostaglandin $I_1$ (thio-$PGI_1$) analogues, to a process for their preparation, to pharmaceutical compositions containing them, and to their use.

Prostaglandin $I_2$ ($PGI_2$) is a physiologically active substance having the following formula:

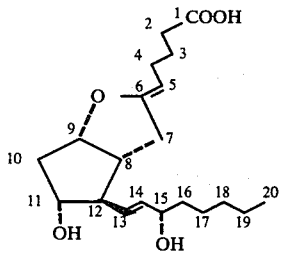

and its chemical name is (5Z,13E)-(9α,11α,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17(1976)].

It is well known that $PGI_2$ can be prepared by incubation of prostaglandin $G_2$ ($PGG_2$) or prostaglandin $H_2$ ($PGH_2$) with microsomal fractions prepared from thoracic aorta of swine, mesenteric artery of swine, rabbit aorta or the stomach fundus of rats. $PGI_2$ has a relaxing activity on the artery, which is peculiar to the artery and which does not operate on other smooth muscle. Furthermore, $PGI_2$ strongly inhibits arachidonic acid-induced blood platelet aggregation of the human.

Taking into consideration that thromboxane $A_2$ prepared by incubation of $PGG_2$ or $PGH_2$ with blood platelet microsome, has a contracting activity on the artery and an aggregating activity on blood platelets, the properties of $PGI_2$ heretofore mentioned show that $PGI_2$ fulfils a very important physiological part in a living body. $PGI_2$ may be useful in the treatment of arteriosclerosis, cardiac failure or thrombosis.

Widespread investigations have been carried out in order to discover inter alia new products possessing the pharmacological properties of the "natural" prostaglandins including $PGI_2$, or one or more of such properties to an enhanced degree, or hitherto unknown pharmacological properties. As a result of extensive research and experimentation, it has been discovered that by replacing the 6,9-epoxy group (i.e. —O—) by an epithio (i.e. —S—), sulphinyl [i.e. —S(O)—] or sulphonyl [i.e. —S(O)$_2$—] group of $PGI_1$ of the formula:

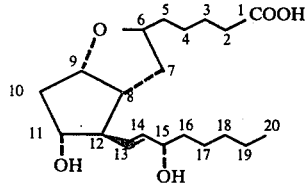

, or of analogues of $PGI_1$, the pharmacological properties of "natural" prostaglandins and analogues thereof are, in some aspects of their activities, improved or modified.

Prostaglandins including $PGI_2$ are generally known to possess various pharmacological properties, for example hypotensive activity, diuretic activity, inhibitory activity on blood platelet aggregation, inhibitory activity on gastric acid secretion and gastric ulceration, bronchodilator activity, antilipolytic activity, antinidatory activity and diarrhoea-producing activity.

Derivatives of a related compound, prostanoic acid, of the formula:

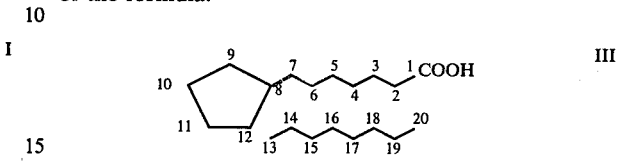

, which have a selective effect (i.e. a separation of a desired activity from undesired side-effects) and possess the same or greater activity in comparison with that of natural prostaglandins, are exceptionally desired. One of the pharmacological activities is used and the other undesired activities are then side-effects.

$PGI_1$ analogues in which the 6,9-epoxy group of $PGI_1$ of formula II is replaced by a 6,9-epithio group, i.e. thio-$PGI_1$ [or (13E)-(6RS,9α,11α,15S)-6,9-epithio-11,15-dihydroxyprost-13-enoic acid] of the formula:

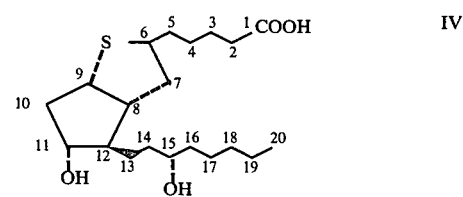

and the sodium salt and methyl ester thereof, are known to possess $PGI_2$-like pharmacological activities such as inhibitory activity on human blood platelet aggregation and vasoconstricting activity on isolated cat coronary artery [cf. J.C.S. Chem. Comm., 375 (1978)].

Unexpectedly, the thio-$PGI_1$ analogues of the present invention and thio-$PGI_1$ itself, have been found to possess a selective strong stimulatory activity on uterine contraction, and are useful in the termination of pregnancy and the induction of labour in pregnant female mammals, and in the control of menstrual regulation in female mammals.

In standard laboratory tests, other pharmacological activities of prostacyclins according to the invention, such as inhibitory activity on blood platelet aggregation, hypotensive activity, inhibitory activity on gastric acid secretion and gastric ulceration and diarrhoea-producing activity were little or very weak, in comparison with, for example, these of $PGE_1$ and $PGI_2$ methyl ester.

In acute toxicity tests, it was confirmed that the thio-$PGI_1$ analogues of the present invention were suitable for use as medicaments.

The properties described above indicate that the thio-$PGI_1$ analogues of this invention are excellent compounds as medicaments possessing useful activity for the purpose of menstrual regulation in females, and the termination of pregnancy and the induction of labour in pregnant females, and have no side-effects. In practice, in clinical tests, the compounds of the present invention showed useful activity and, on the other hand, produced no side-effects such as the various signs caused by change of blood pressure, diarrhoea, vomiting, and, in particular, pains in the hypogastric region.

The results of standard laboratory tests are shown below in Table 1, wherein the various activities are shown relative to $PGE_1$.

TABLE 1

| Compound | UCA | BP | PAI | GSI | GUI | Diarrhoea | $LD_{50}$ (mg/kg) |
|---|---|---|---|---|---|---|---|
| A | 11.5 | 0.2 | 0.03 | <0.1 | <0.5 | 0.072 | 100 |
| B | 10 | 0.2 | 0.038 | <0.1 | <0.5 | <0.1 | — |
| C | 15.8 | <0.1 | 0.011 | 0.3 | <0.5 | <0.02 | 100 |
| D | 23.1 | <0.1 | 0.006 | <0.3 | <0.5 | 0.095 | 25 |
| E | 27.3 | 0.55 | 0.21 | <0.3 | <0.5 | 0.514 | — |
| $PGE_1$ | 1 | 1 | 1 | 1 | 1 | 1 | — |
| $PGI_2$ methyl ester | 0.5 | 20 | 85 | — | — | <0.1 | — |

Referring to the compounds tested and the column headings:

A: (13E)-(6RS,9α,11α,15S)-6,9-epithio-11,15-dihydroxyprost-13-enoic acid methyl ester.

B: (13E)-(6RS,9α,11α,15S)-6,9-epithio-11,15-dihydroxyprost-13-enoic acid.

C: (13E)-(6RS,9α,11α,15R)-6,9-epithio-11,15-dihydroxy-15-(1-butylcyclobutyl)-16,17,18,19,20-pentanorprost-13-enoic acid methyl ester.

D: (13E)-(6RS,9α,11α,15R)-6,9-epithio-11,15-dihydroxy-16,16-dimethylprost-13-enoic acid methyl ester.

E: (13E)-(6RS,9α,11α,15S,16S)-6,9-epithio-11,15-dihydroxy-16-methylprost-13-enoic acid methyl ester.

UCA (Uterine contraction activity)

The compounds stimulate uterine contraction in the pregnant female rat when administered intravenously on the 20th day of gestation.

BP (Hypotensive activity)

The compounds produce falls in blood pressure when administered intravenously to the allobarbital-anaesthetised dog.

PAI (Inhibitory activity on blood platelet aggregation)

The compounds produce a 50% inhibition of adenosine diphosphate-induced blood platelet aggregation in platelet-rich plasma of rats.

GSI (Inhibitory activity on gastric acid secretion)

The compounds produce an increase in gastric acid pH from 2.0-2.5 to at least 4.0 in 50% of pentagastrin-treated rats when perfused intravenously.

GUI (Inhibitory activity on gastric ulceration)

The compounds produce an inhibition of stress ulceration by oral administration in the stress ulceration of rats produced according to the method of Takagi and Okabe [Jap. J. Pharmc., 18, 9–18 (1968)], i.e. by soaking rats in a water bath at 19° C. for 6 hours.

Diarrhoea (Diarrhoea-producing activity)

The compounds produce diarrhoea in 50% of mice by oral administration.

$LD_{50}$ (Acute toxicity tests)

The compounds are injected intravenously into mice.
Moreover, other compounds of the present invention [prepared as hereafter described in the Examples] other than the above compounds for which results are given in Table 1 stimulate uterine contraction when administered intravenously to the pregnant female rat on the 20th day of gestation at doses of 0.2–100 μg/kg animal body weight.

The present invention accordingly provides new prostaglandin $I_1$ analogues of the general formula:

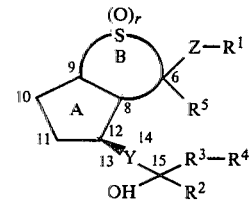

[wherein the ring A represents a grouping of the formula:

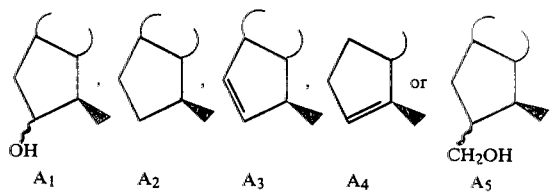

(wherein the wavy line ~~~ represents α- or β-configuration, or mixtures thereof), the ring B represents a grouping of the formula:

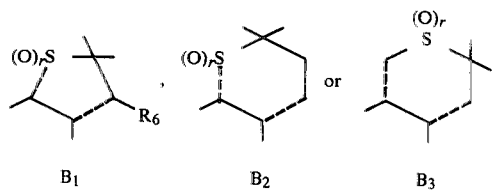

(wherein $R^6$ represents a hydrogen atom or a methyl or ethyl group, and r is zero, one or two), Y represents an ethylene group, i.e. —$CH_2CH_2$—, a cis- or trans-vinylene group, i.e. —CH=CH—, or an ethynylene group, i.e. —C≡C—, Z represents a grouping of the formula:

| —(CH_2)_m— | $Z_1$ |
| —(CH_2)_3—CHR^7— | $Z_2$ |
| —(CH_2)_2—CHR^7—CH_2— | $Z_3$ |
| —CH_2—CHR^7—(CH_2)_2— | $Z_4$ |
| —CHR^7—(CH_2)_3— | $Z_5$ |
| or trans-(CH_2)_2—CH=CH— | $Z_6$ |

(wherein m is 3, 4 or 5, and $R^7$ represents a methyl or ethyl group) $R^1$ represents a grouping of the formula:

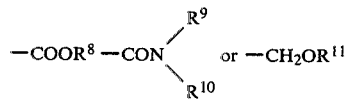

(wherein $R^8$ represents)
(1) a hydrogen atom,
(2) an alkyl group containing from 1 to 12 carbon atoms,
(3) an aralkyl group containing from 7 to 13 carbon atoms, (4) a cycloalkyl group containing from 4 to 7 carbon atoms unsubstituted or substituted by at least one alkyl group containing from 1 to 4 carbon atoms,
(5) a phenyl group unsubstituted or substituted by at least one halogen atom, trifluoromethyl group, alkyl, alkoxy or alkylthio group containing from 1 to 4 carbon atoms, or by a phenyl group,
(6) a naphthyl group,
(7) a 2,3- or 1,3-dihydroxypropyl group,
(8) a 2,3- or 1,3-bisalkanoyloxypropyl group,
(9) a grouping of the formula:

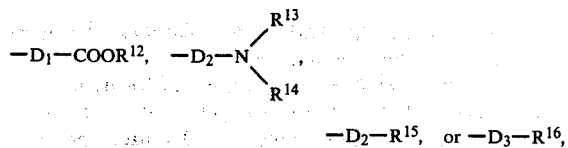

wherein $D_1$ represents an alkylene group containing from 1 to 12 carbon atoms, $D_2$ represents an alkylene group containing from 2 to 12 carbon atoms, $D_3$ represents a single bond, or an alkylene group containing from 1 to 12 carbon atoms, $R^{12}$, $R^{13}$ and $R^{14}$, which may be the same or different, each represent an alkyl group containing from 1 to 4 carbon atoms, $R^{15}$ represents a hydroxy group or an alkoxy or alkylthio group containing from 1 to 4 carbon atoms, and $R^{16}$ represents a heterocyclic ring,
or (10) a grouping of the formula:

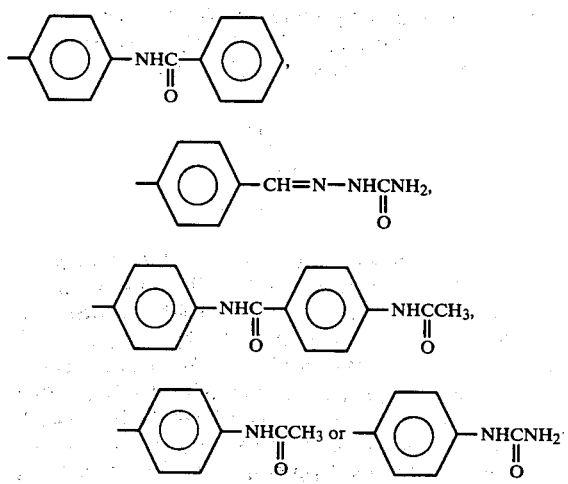

$R^9$ and $R^{10}$, which may be the same or different, each represent a hydrogen atom, an alkyl group containing from 1 to 12 carbon atoms, an alkylsulphonyl group containing from 1 to 4 carbon atoms, an alkanoyl group containing from 2 to 5 carbon atoms, or

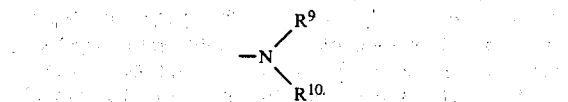

represents a heterocyclic ring, and $R^{11}$ represents a hydrogen atom, or an alkanoyl group containing from 2 to 5 carbon atoms), $R^2$ represents a hydrogen atom, or a methyl or ethyl group, $R^3$ represents a single bond or an alkylene group containing from 1 to 5 carbon atoms, $R^4$ represents a hydrogen atom, an alkyl or alkoxy group containing from 1 to 8 carbon atoms, a cycloalkyl or cycloalkyloxy group containing from 4 to 7 carbon atoms unsubstituted or substituted by at least one alkyl group containing from 1 to 8 carbon atoms, or represents a phenyl or phenoxy group unsubstituted or substituted by at least one halogen atom, trifluoromethyl group, or alkyl group containing from 1 to 4 carbon atoms, with the proviso that, when $R^3$ represents a single bond, $R^4$ does not represent an alkoxy, cycloalkyloxy or phenoxy group, $R^5$ represents a hydrogen atom, or a methyl or ethyl group, the absolute configuraton of $C_6$ and $C_{15}$ which may be the same or different is R or S, or mixtures thereof, i.e. RS, and with the proviso that, when one of the groups $R^5$, $R^6$ and $R^7$ represents a methyl or ethyl group the other two groups are hydrogen atoms], and cyclodextrin clathrates thereof and, when the compound of general formula V contains a carboxy group, non-toxic (e.g. sodium) salts thereof and, when the compound of general formula V contains an amino group, non-toxic acid addition salts thereof, with the exclusion of those prostaglandin analogues wherein $R^1$ represents a group $—COOR^8$ in which $R^8$ represents a hydrogen atom or a methyl group, Z represents a grouping $Z_1$ in which m is 4, $R^5$ represents a hydrogen atom, B represents a grouping $B_1$ in which $R^6$ represents a hydrogen atom, A represents a grouping $A_1$ in which the hydroxy group is in α-configuration, Y represents trans-vinylene, the hydroxy group attached to the 15-position is in S-configuration, $R^2$ represents a hydrogen atom and the grouping $—R^3—R^4$ represents an n-pentyl group, and the corresponding sodium salts of such prostaglandin analogues wherein $R^1$ represents a group —COOH.

Preferably the hydroxy group attached to the C-15 carbon atom and the hydroxy or hydroxymethyl group attached to the C-11 carbon atom are in α-configuration.

It is to be understood that alkyl and alkylene groups and alkyl and alkylene moieties of groups referred to in this specification and the accompanying claims may be straight- or branched-chain.

The present invention is concerned with all compounds of general formula V in the optically active "natural" form or its enantiomeric form, or mixtures thereof, more particularly the racemic form, consisting of equimolecular mixtures of the optically active "natural" form and its enantiomeric form.

As will be apparent to those skilled in the art, the compounds depicted in general formula V have at least five centres of chirality at the C-6, C-8, C-9, C-12 and C-15 carbon atoms. Still further centres of chirality may occur in branched-chain alkyl or alkylene groups, or when one of the groups $R^6$ and $R^7$ is a methyl or ethyl group, or the ring A is a grouping of formula $A_1$ or $A_5$. The presence of chirality leads as is well known to the existence of isomerism. However, the compounds of general formula V all have such a configuration that the substituent groups attached to the cyclopentane ring carbon atoms in positions identified as 8 and 12 are trans with respect to each other and that the substituent groups attached to the cyclopentane ring carbon atoms in the positions identified as 8 and 9 are cis with respect to each other. Accordingly, all isomers of general formula V, and mixtures thereof, which have those substituent groups attached to the cyclopentane ring carbon atoms in positions 8 and 12 in the trans-configuration, and those attached in 8 and 9 position in the cis-configuration and have hydroxy group(s) as depicted in the 11 and/or 15-position(s) are to be considered within the scope of general formula V.

Examples of the alkyl group containing from 1 to 12 carbon atoms represented by $R^8$, $R^9$ and $R^{10}$ are methyl, ethyl, propyl, butyl, pentyl, hexyl, heptyl, octyl, nonyl, decyl, undecyl, dodecyl, and their isomers.

Examples of the aralkyl group containing from 7 to 13 carbon atoms represented by $R^8$ are benzyl, 1-phenylethyl, 2-phenylethyl, 3-phenylbutyl, 4-phenylbutyl, 1-(2-naphthyl)ethyl, 2-(1-naphthyl)ethyl and biphenylmethyl.

Examples of the cycloalkyl group containing from 4 to 7 carbon atoms unsubstituted or substituted by at least one alkyl group containing from 1 to 4 carbon atoms represented by $R^8$ are cyclobutyl, 1-propylcyclobutyl, 1-butylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, (1-methyl-3-propyl)cyclopentyl, (2-methyl-3-propyl)cyclopentyl, (2-methyl-4-propyl)cyclopentyl, cyclohexyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, (2,6-dimethyl-4-propyl)cyclohexyl and cycloheptyl.

Examples of the phenyl group unsubstituted or substituted by at least one halogen atom, trifluoromethyl group, alkyl, alkoxy or alkythio group containing from 1 to 4 carbon atoms, or by a phenyl group represented by $R^8$ are phenyl, 2-, 3- or 4-chlorophenyl, 2,4-dichlorophenyl, 2,4,6-trichlorophenyl, 2-, 3- or 4-tolyl, 2-, 3- or 4-ethylphenyl, 2-, 3- or 4-isopropylphenyl, 2-, 3- or 4-tert-butylphenyl, 4-sec-butylphenyl, 2,4-dimethylphenyl, 2,5-dimethylphenyl, 2,6-dimethylphenyl, 2,6-diethylphenyl, (2-isopropyl-5-methyl)phenyl, 2,6-diisopropylphenyl, (2-tert-butyl-6-methyl)phenyl, (2-tert-butyl-4-methyl)phenyl, 2,4-di-tert-butylphenyl, 2,6-di-tert-butylphenyl, 2,4,6-trimethylphenyl, (2-tert-butyl-4,6-dimethyl)phenyl, (2,6-di-tert-butyl-4-methyl)phenyl, 2,4,6-tri-tert-butylphenyl, 3-trifluoromethylphenyl, 4-biphenyl, 2-, 3- or 4-methoxyphenyl, 2-, 3- or 4-ethoxyphenyl, 2-, 3- or 4-methylthiophenyl and 2-, 3- or 4-ethylthiophenyl.

Examples of the alkanoyl moiety of the 2,3- and 1,3-bisalkanoyloxypropyl groups represented by $R^8$ are acetyl, propionyl, butyryl, isobutyryl, valeryl, dodecanoyl, tetradecanoyl, hexadecanoyl and octadecanoyl.

Examples of the alkylene moiety of the —D$_1$—COOR$^{12}$,

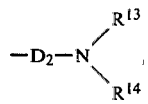

—D$_2$—R$^{15}$ and —D$_3$—R$^{16}$ groups represented by $R^8$ are methylene (except for the D$_2$ moiety), ethylene, trimethylene, tetramethylene, pentamethylene, hexamethylene, heptamethylene, octamethylene, nonamethylene, decamethylene, undecamethylene, dodecamethylene and their isomers.

Examples of the alkyl group or the alkyl moiety of the alkoxy, alkylthio and alkylsulphonyl groups represented by $R^9$, $R^{10}$, $R^{12}$, $R^{13}$, $R^{14}$ and $R^{15}$ are methyl, ethyl, propyl, isopropyl, butyl, isobutyl, sec-butyl and tert-butyl.

Examples of the heterocyclic ring represented by $R^{16}$ are furyl, tetrahydrofuryl, 3-phthalidyl, pyridyl and thienyl.

Examples of the heterocyclic ring represented by

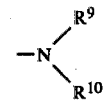

are pyrrolidyl, piperidino, morpholino, hexamethyleneiminyl, and piperazinyl.

Preferably the ring A is a grouping of formula A$_1$ or A$_2$. Preferably the ring B is a grouping of formula B$_1$ (wherein $R^6$ is a hydrdogen atom) or B$_2$. More preferably the ring A and the ring B together represent a grouping of the formula:

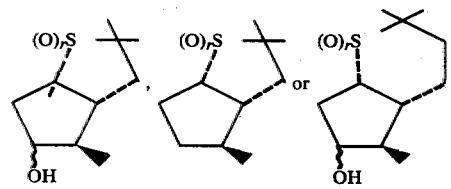

wherein r is as hereinbefore defined, Y preferably represents a trans-vinylene group. Z preferably represents a grouping of formula Z$_1$ or Z$_6$. $R^1$ preferably represents a grouping of the formula —COOR$^8$ or

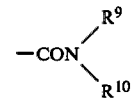

wherein $R^8$, $R^9$ and $R^{10}$ are as hereinbefore defined.

Preferably the grouping —R$^3$—R$^4$ represents, for example methyl, ethyl, 1-methylethyl, propyl, 1-methylpropyl, 2-methylpropyl, 1-ethylpropyl, butyl, 1-methylbutyl, 2-methylbutyl, 3-methylbutyl, 1-ethylbutyl, 2-ethylbutyl, pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, hexyl, 1-methylhexyl, 2-methylhexyl, 1,1-dimethylhexyl, 1-ethylhexyl, 2-ethylhexyl, heptyl, 2-ethylheptyl, nonyl, undecyl, cyclobutyl, 1-propylcyclobutyl, 1-butylcyclobutyl, 1-pentylcyclobutyl, 1-hexylcyclobutyl, 2-methylcyclobutyl, 2-propylcyclobutyl, 3-ethylcyclobutyl, 3-propylcyclobutyl, 2,3,4-triethylcyclobutyl, cyclopentyl, cyclopentylmethyl, 1-cyclopentylethyl, 2-cyclopentylethyl, 2-cyclopentylpropyl, 3-cyclopentylpropyl, 2-pentylcyclopentyl, 2,2-dimethylcyclopentyl, 3-ethylcyclopentyl, 3-propylcyclopentyl, 3-butylcyclopentyl, 3-tert- butylcyclopentyl, (1-methyl-3-propyl)cyclopentyl, (2-methyl-3-propyl)cyclopentyl, (2-methyl-4-propyl)cyclopentyl, cyclohexyl, cyclohexylmethyl, 1-cyclohexylethyl, 2-cyclohexylethyl, 3-cyclohexylpropyl, (1-methyl-2-cyclohexyl)ethyl, 2-cyclohexylpropyl, (1-methyl-2-cyclohexyl)ethyl, 2-cyclohexylpropyl, (1-methyl-1-cyclohexyl)ethyl, 4-cyclohexylbutyl, 3-ethylcyclohexyl, 3-isopropylcyclohexyl, 4-methylcyclohexyl, 4-ethylcyclohexyl, 4- propylcyclohexyl, 4-tert-butylcyclohexyl, 2,6-dimethylcyclohexyl, 2,2-dimethylcyclohexyl, (2,6-dimethyl-4-propyl)cyclohexyl, 1-methylcyclohexylmethyl, cycloheptyl, cycloheptylmethyl, 1-cycloheptylethyl, 2-cycloheptylethyl, phenyl, benzyl, 1-phenylethyl, 2-phenylethyl, 3-phenylpropyl, 4-phenylbutyl, 5-phenylpentyl, (1-methyl-2-phenyl)ethyl, (1,1-dimethyl-2-phenyl)ethyl, (1-methyl-1-phenyl)ethyl, 1-phenylpentyl, phenoxymethyl, 2-phenoxyethyl, 3-phenoxypropyl, 4-phenoxybutyl, 5-phenoxypentyl, 3-chlorophenoxymethyl, 4-chlorophenoxymethyl, 4-fluorophenoxymethyl, 3-trifluoromethylphenoxymethyl, 2-methylphenoxymethyl, 3-methylphenoxymethyl, 4-methylphenoxymethyl, 4-ethylphenoxymethyl, 4-tert-butylphenoxymethyl, 4-sec-butylphenoxymethyl, propoxymethyl, isopropoxymethyl, butoxymethyl, pentyloxymethyl, hexyloxymethyl, 1-ethoxyethyl, 1-propoxyethyl, 1-isopropoxyethyl, 1-neopentyloxyethyl, 1-pentyloxyethyl, (1-methyl-1-ethoxy)ethyl, (1-methyl-1-propoxy)ethyl, (1-methyl-1-isobutoxy)ethyl, (1-methyl-1-neopentyloxy)ethyl, (1-methyl-1-butoxy)ethyl, (1-methyl-1-isopentyloxy)ethyl, (1-methyl-1-pentyloxy)ethyl, 2-ethoxyethyl, 2-propoxyethyl, 2-butoxyethyl, 2-(1-ethylbutoxy)ethyl, 2-pentyloxyethyl, 1-ethoxypropyl, 1-propoxypropyl, 1-(2-methylbutoxy)propyl, 1-pentyloxypropyl, 2-metehoxypropyl, 3-methoxypropyl, 3-ethoxypropyl, 3-propoxypropyl, 3-sec-butoxypropyl, 3-isobutoxypropyl, 3-butoxypropyl, (1-methyl-2-methoxy)ethyl, (1-methyl-2-ethoxy)ethyl, (1-methyl-2-isobutoxy)ethyl, 1-pentyloxybutyl, (1-pentyloxy-2-methyl)propyl, 4-methoxybutyl, 4-ethoxybutyl, 4-propoxybutyl, (1-methyl-3-methoxy)propyl, (1-methyl-3-propoxy)propyl, (2-methyl-3-methoxy)propyl, (1,1-dimethyl-2-ethoxy)ethyl, (1,1-dimethyl-2-propoxy)ethyl, (1,1-dimethyl-2-isobutoxy)ethyl, 5-methoxypentyl, 5-ethoxypentyl, 1-pentyloxypentyl, (1-ethyl-3-propoxy)propyl, cyclobutyloxymethyl, cyclopentyloxymethyl, cyclohexyloxymethyl, cycloheptyloxymethyl, 2-cyclopentyloxyethyl or 2-cyclohexyloxyethyl. Preferably $R^2$ represents a hydrogen atom and the grouping —$R^3$—$R^4$ represents an n-pentyl group unsubstituted or substituted by one or two methyl groups, a cyclobutyl group substituted by an alkyl group containing from 1 to 4 carbon atoms or a phenoxymethyl group in which the phenoxy group is substituted by a halogen atom.

Prostaglandin analogues of general formula V wherein $R^1$ represents a grouping of the formula —$COOR^8$ or

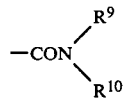

wherein $R^9$ represents a methylsulphonyl group and $R^{10}$ represents a hydrogen atom, and $R^8$ represents a hydrogen atom, an alkyl group containing from 1 to 4 carbon atoms, or a decyl, 2-hydroxyethyl, 4-ethylphenyl, 4-benzoylaminophenyl, 4-methylthiophenyl, 2,3-dihydroxypropyl, 2-ethylthioethyl, furfuryl, tetrahydrofurfuryl, phthalid-3-yl, 4-semicarbazonotolyl or 1,3-bisstearoyloxy-2-propyl group are preferred. Prostaglandin analogues of general formula V wherein $R^1$ represents a grouping of the formula —$COOR^8$ in which $R^8$ represents an alkyl group containing from 1 to 65 4 carbon atoms are especially preferred.

Examples of suitable non-toxic acid addition salts which may be formed by those compounds of general formula V which contain an amino group are the salts with inorganic acids such as hydrochloric acid, hydrobromic acid, hydroiodic acid, sulphuric acid, phosphoric acid and nitric acid, and with organic acids such as acetic acid, propionic acid, lactic acid, tartaric acid, citric acid, methanesulphonic acid, ethanesulphonic acid, benzenesulphonic acid, toluenesulphonic acid, isethionic acid and succinic acid. It is to be understood that the amino group may form part of a heterocyclic ring, for example a piperazinyl ring represented by the grouping

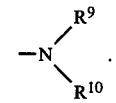

According to a feature of the present invention, the thio-$PGI_1$ analogues of general formula V, wherein the ring B is a grouping of formula $B_1$, wherein r is zero, and $R^6$ is as hereinbefore defined, Z represents a grouping of the formula $Z_1$, $Z_2$, $Z_3$, $Z_4$ or $Z_5$, $R^1$ represents a grouping of the formula —$COOR^8$, wherein $R^8$ represents a hydrogen atom, or an alkyl group containing from 1 to 4 carbon atoms, and the other aymbols are as hereinbefore defined, i.e. compounds of the general formula:

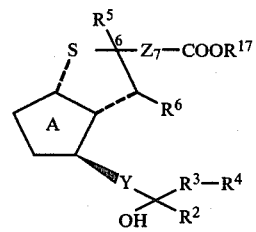

[wherein $Z_7$ represents a grouping of the formula $Z_1$, $Z_2$, $Z_3$, $Z_4$ or $Z_5$, $R^{17}$ represents a hydrogen atom, or an alkyl group containing from 1 to 4 carbon atoms, and the other symbols are as hereinbefore defined], are prepared by the reaction of a compound of general formula:

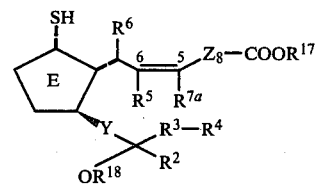

[wherein the ring E represents a group of the formula:

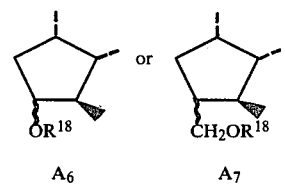

or a grouping of formula $A_2$, $A_3$ or $A_4$, $R^{18}$ represents a hydrogen atom, or a hydroxy-protecting group which is eliminated under acidic conditions (preferably a hydrogen atom), $R^{7a}$ represents a hydrogen atom, or a methyl or ethyl group, $Z_8$ represents a grouping of the formula:

| —$(CH_2)_{m-1}$— | $Z_9$, |
|---|---|
| —$(CH_2)_2$—$CHR^7$— | $Z_{10}$, |
| —$CH_2$—$CHR^7$—$CH_2$— | $Z_{11}$, |
| or —$CHR^7$—$(CH_2)_2$— | $Z_{12}$ | the double bond between $C_5$ and $C_6$ is cis, and the other symbols are as hereinbefore defined, with the proviso that, when $R^{7a}$ represents a methyl or ethyl group, $R^5$ and $R^6$ each represents a hydrogen atom and $Z_8$ represents a grouping of formula $Z_9$ (in which m is 4)] under acidic conditions.

The reaction under acidic conditions may be carried out with (1) an aqueous solution of an organic acid such as acetic acid, propionic acid, oxalic acid, p-toluenesulphonic acid, or of an inorganic acid such as hydrochloric acid, sulphuric acid, or phosphoric acid, advantageously in the presence of an inert organic solvent miscible with water, e.g. a lower alkanol such as methanol or ethanol, preferably methanol, or an ether such as 1,2-dimethoxyethane, dioxan or tetrahydrofuran, preferably tetrahydrofuran, at a temperature of from ambient to 75° C., or (2) an anhydrous solution of an organic acid such as p-toluenesulphonic acid or trifluoroacetic acid in a lower alkanol such as methanol or ethanol at a temperature of 10° to 45° C., or (3) an anhydrous solution of p-toluenesulphonic acid-pyridine complex or trifluoroacetic acid-pyridine complex in a lower alkanol such as methanol or ethanol at a temperature of 10° to 60° C. Advantageously, the reaction under acidic conditions may be carried out with a mixture of dilute hydrochloric acid and tetrahydrofuran, a mixture of dilute hydrochloric acid and methanol, a mixture of acetic acid, water and tetrahydrofuran, a mixture of trifluoroacetic acid-pyridine complex and methanol, or a mixture of p-toluenesulphonic acid-pyridine complex and methanol.

The thio-$PGI_1$ analogues of general formula V, wherein the ring B is a grouping of formula $B_2$, in which r is zero, Z represents a grouping of the formula $Z_1$, $Z_2$, $Z_3$, $Z_4$ or $Z_5$, $R^1$ represents a grouping of the formula —$COOR^8$, wherein $R^8$ represents a hydrogen atom, or an alkyl group containing from 1 to 4 carbon atoms, and the other symbols are as hereinbefore defined, i.e. compounds of the general formula:

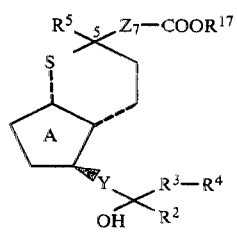

(wherein the various symbols are as hereinbefore defined) are prepared by the reaction of a compound of the general formula:

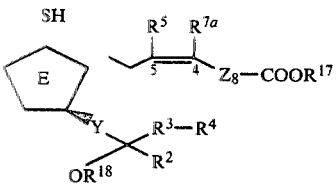

(wherein the double bond between $C_4$ and $C_5$ is cis, and various symbols are as hereinbefore defined) under acid conditions, for example, those described above for the reaction of a compound of general formula VIA.

The thio-$PGI_1$ analogues of general formula V, wherein the ring B rerpresents a grouping of formula $B_3$, in which r is zero, Z represents a grouping of formula $Z_1$, $Z_2$, $Z_3$, $Z_4$, or $Z_5$, $R^1$ represents a grouping of the formula —$COOR^8$, wherein $R^8$ represents a hydrogen atom or an alkyl group containing from 1 to 4 carbon atoms, and the other symbols are as hereinbefore defined, i.e. compounds of the general formula:

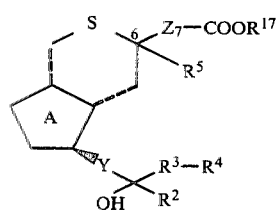

(wherein the various symbols are as hereinbefore defined) are prepared by reaction of a compound of the general formula:

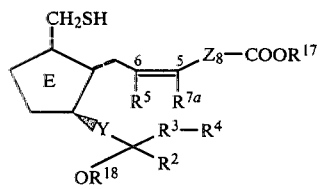

(wherein the double bond between $C_5$ and $C_6$ is cis, and the various symbols are as hereinbefore defined) under acid conditions, for example those described above for the reaction of a compound of general formula VIA.

The products of general formula VA, VB or VC, thus obtained, are a mixture of isomers in which the groups attached to the carbon atom at 6 (or 5, when the formula is VB) are in S- and R-configuration. If desired, the mixture may be separated by column or thin layer chromatography on silica gel, to give the separate isomers.

The hydroxy-protecting groups which are eliminated under acidic conditions as used in the process of the invention and referred to hereafter in this specification and the accompanying claims are groups which have no influence on other parts of the compounds during elimination of the protecting group, and which are easily eliminated under mild acidic conditions, for example, (1) a heterocyclic group such as tetrahydropyran-2-yl, tetrahydrofuran-2-yl or tetrahydrothiopyran-2-yl, (2) an ether group such as 1-ethoxyethyl, 1-methoxy-1-metehylethyl, 1-methoxycyclohexyl, or 1-methoxy-1-phenylethyl, or (3) a tri-substituted silyl group such as trimethylsilyl, triethylsilyl, tributylsilyl, tert-butyldimethylsilyl, tribenzylsilyl, or triphenylsilyl. Preferably the hydroxy-protecting group is tetrahydropyran-2-yl.

Compounds of general formula VIA may be prepared by the reaction of a compound of the general formula:

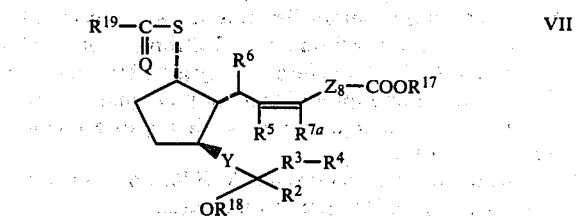
VII (wherein Q represents an oxygen or sulphur atom, $R^{19}$ represents an alkyl group containing from 1 to 4 carbon atoms or a phenyl group, and the other symbols are as hereinbefore defined) under basic conditions. The reaction under basic conditions may be carried out under an inert gas atmosphere, e.g. nitrogen or argon, with an alkali metal, e.g. sodium, potassium or lithium, hydroxide or carbonate or alkoxide containing from 1 to 4 carbon atoms at a temperature of 0° to 50° C., preferably at room temperature.

It is necessary that the reaction be carried out cautiously, because reaction for a long time at a temperature above ambient temperature, leads to a side reaction resulting in the preparation of disulphides of general formula VIII as described hereafter.

Compounds of general formula VII, wherein $R^{18}$ represents a hydrogen atom, and the other symbols are as hereinbefore defined, may be prepared from corresponding compounds of general formula VII, wherein $R^{18}$ represents a hydroxy-protecting group which is eliminated under acidic conditions, and the other symbols are as hereinbefore defined, i.e. compounds of the general formula:

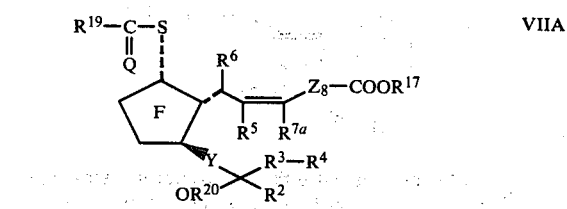
VIIA (wherein the ring F represents a grouping of the formula

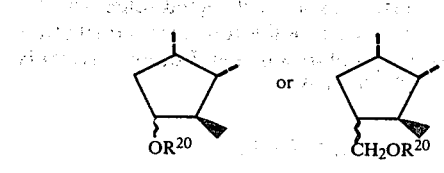

A8    A9 or a grouping of formula $A_2$, $A_3$, or $A_4$, $R^{20}$ represents a hydroxy-protecting group eliminated under acidic conditions, and the other symbols are as hereinbefore defined) by means heretofore mentioned for the conversion of compounds of general formula VIA to those of general formula VA.

Compounds of general formula VIA may also be prepared from a disulphide of the general formula:

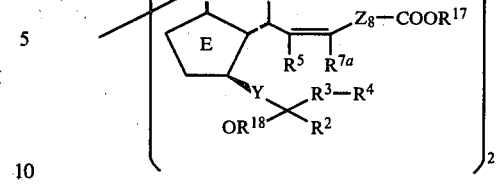
VIII (wherein the various symbols are as hereinbefore defined) by methods known per se for the conversion of a disulphide into a thiol, for example the method as described in Anal, Chem., 37(1), 164(1965). By the term 'methods known per se' as used in this specification is meant methods heretofore used or described in the chemical literature.

Compounds of general formula VIII, wherein $R^{18}$ represents a hydrogen atom, and the other symbols are as hereinbefore defined, may be obtained from corresponding compounds of general formula VIII, wherein $R^{18}$ represents a hydroxy-protecting group eliminated under acidic conditions, and the other symbols are as hereinbefore defined, by means heretofore mentioned for the conversion of compounds of general formula VIA to those of general formula VA.

Disulphides of general formula VIII, wherein $R^{18}$ represents a hydroxy-protecting group eliminated under acidic conditions, and the other symbols are as hereinbefore defined, may be prepared from compounds of general formula VIIA by means heretofore menioned for the conversion of compounds of general formula VII to those of general formula VIA, under an atmosphere of oxygen or air. The reaction occurs with conversion of the group

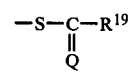

(wherein Q and $R^{19}$ are as hereinbefore defined) into the mercapto group, and subsequent oxidation with oxygen or air to give the disulphides. The reaction may also be carried out under an atmosphere of an inert gas, e.g. nitrogen or argon, at a temperature above ambient temperature using a long rection time.

Compounds of general formula VIIA may be prepared by reaction of a compound of the general formula:

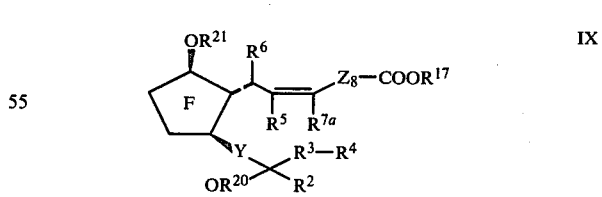
IX (wherein $R^{21}$ represents an alkylsulphonyl or arylsulphonyl group, and the other symbols are as hereinbefore defined) with a compound of the general formula:

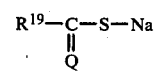
X

[wherein R[19] and Q are as hereinbefore defined] in an inert organic solvent, e.g. dimethyl sulphoxide or a mixture of dimethyl sulphoxide and 1,2-dimethoxyethane, at a temperature of 0° to 50° C. Compounds of general formula X may be prepared by methods known per se.

Compounds of general formula IX may be prepared by reaction of a compound of the general formula:

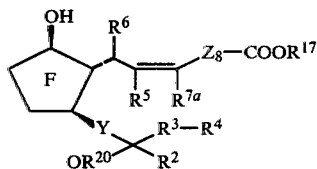   XI (wherein the various symbols are as hereinbefore defined) with an alkylsulphonyl halide, e.g. methanesulphonyl chloride or ethanesulphonyl chloride, or an arylsulphonyl halide, e.g. p-toluenesulphonyl chloride or benzenesulphonyl chloride, in an inert organic solvent, e.g. methylene chloride, in the presence of a tertiary amine, e.g. pyridine or triethylamine, at a temperature of −30° to 50° C.

Compounds of general formula XI may be prepared by the series of reactions depicted schematiclaly below in Scheme A, wherein R[22] represents an alkanoyl group containing from 2 to 5 carbon atoms, or a benzoyl or formyl group, and the other symbols are as hereinbefore defined.

SCHEME A

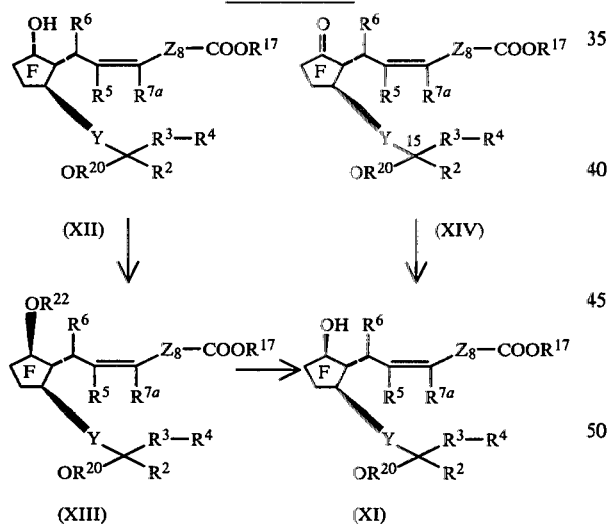

Referring to Scheme A, compounds of general formula XIII may be prepared by reacting compounds of general formula XII with an acid of the general formula:

R[22]OH    XV (wherein R[22] is as hereinbefore defined) in tetrahydrofuran in the presence of triphenylphosphine and diethyl azodicarboxylate at room temperature, and may then be converted to compounds of general formula XI by means heretofore mentioned for the conversion of compounds of general formula VII to those of general formula VIA.

Compounds of general formula XIV may also be converted to compounds of general formula XI by methods known per se for the conversion of an oxo group in the 9-position of a prostaglandin E compound to a hydroxy group, for example by means of sodium borohydride in methanol. The product is a mixture of compounds of general formula XI and those of general formula XII, and the mixture is separated by conventional means, for example, by thin layer, column or high speed liquid chromatography or silica gel to give the separate isomers.

Compounds of general formula VIB may be prepared from compounds of the general formula:

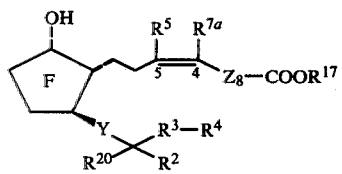   XVI

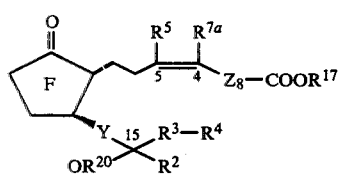   XVII (wherein the double bond between C4 and C5 is cis, and the other symbols are as hereinbefore defined) by means heretofore mentioned for the conversion of compounds of general formula XII or XIV to those of general formula VIA.

Compounds of general formula VIC may be prepared from a compound of the general formula:

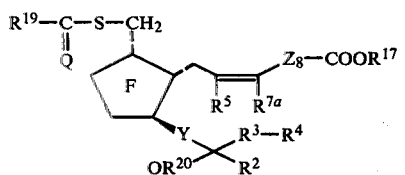   VIIB (wherein the various symbols are as hereinbefore defined) by means heretofore mentioned for the conversion of compounds of general formula VIIA to those of general formula VIA.

Compounds of general formula VIIB may be prepared by the series of reactions depicted schematically below in Scheme B, wherein R[23] represents an alkylsulphonyl or arylsulphonyl group, and the other symbols are as hereinbefore defined.

SCHEME B

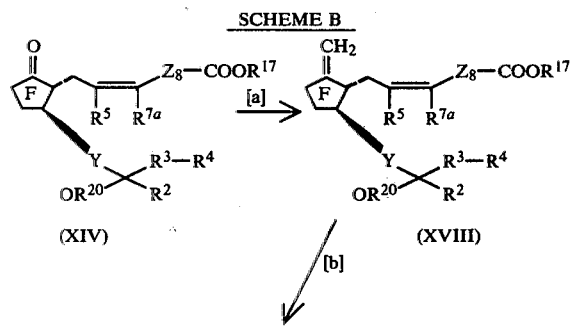

-continued
SCHEME B

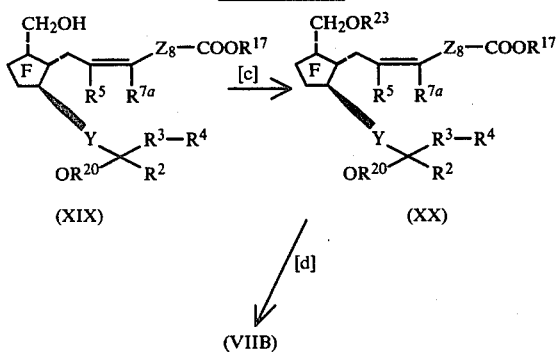

Referring to Scheme B, the conversion [a] may be carried out by the method described in J. Amer. Chem. Soc., 95, 6462 (1973). The conversion [b] may be carried out by hydroboration [cf. 'Organic Reactions', volume 13, Chapter 1 (1963), John Wiley & Sons, Inc. (USA)], and then oxidation. Preferably the hydroboration reagent is a bulky organoboron compound such as 9-borabicyclo[3.3.1]nonane (9-BBN). Preferably the oxidation is carried out with hydrogen peroxide in the presence of an alkali metal, e.g. sodium or potassium, hydroxide.

The conversion [c] may be carried out by means heretofore mentioned for the conversion of compounds of general formula XI to those of general formula IX, and the conversion [d] may be carried out by means heretofore mentioned for the conversion of compounds of general formula IX to those of general formula VIIA.

The thio-PGI$_1$ analogues of general formula V, wherein r is 1, $R^1$ represents a grouping of the formula —COOR$^8$, wherein $R^8$ represents a hydrogen atom, or an alkyl group containing from 1 to 4 carbon atoms, and the other symbols are as hereinbefore defined, i.e. sulphoxides of the general formula:

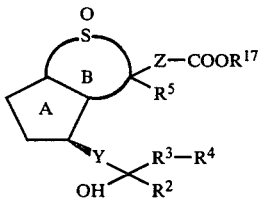   VD (wherein the various symbols are as hereinbefore defined) or the thio-PGI$_1$ analogues of general formula V, wherein r is 2, $R^1$ represents a grouping of the formula —COOR$^8$, wherein $R^8$ represents a hydrogen atom, or an alkyl group containing from 1 to 4 carbon atoms, and the other symbols are as hereinbefore defined, i.e. sulphones of the general formula:

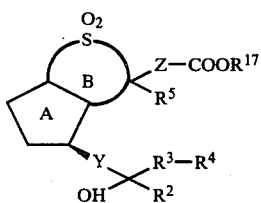   VE (wherein the various symbols are as hereinbefore defined) are prepared by oxidation of a compound of the general formula:

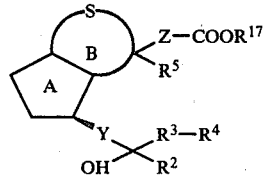   VF wherein the various symbols are as hereinbefore defined.

Suitable oxidation methods for the conversion of sulphides into sulphoxides or sulphones are well known. For example, the oxidation may be carried out with an appropriate oxidant, e.g. hydrogen peroxide, sodium periodate, peracetic acid, perbenzoic acid or m-chloroperbenzoic acid, in an inert solvent, e.g. methylene chloride, chloroform, acetone, benzene, toluene, tetrahydrofuran, ethyl acetate, acetic acid, water, methanol, ethanol, or a mixture of two or more of them, adavantageously in the presence of sodium bicarbonate or potassium bicarbonate, at a temperature of $-78°$ to 150° C., preferably at or below 45° C.

The thio-PGI$_1$ analogues of general formula V, wherein Z represents a group $Z_6$, $R^1$ represents a grouping of the formula —COOR$^8$, wherein $R^8$ represents a hydrogen atom, or an alkyl group containing from 1 to 4 carbon atoms, and the other symbols are as hereinbefore defined, i.e. compounds of the general formula:

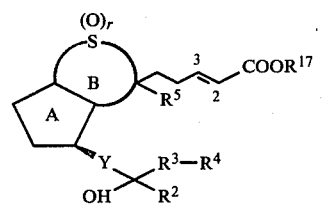   VG (wherein the double bond between $C_2$ and $C_3$ is trans, and the various symbols are as hereinbefore defined) are prepared from a compound of the general formula:

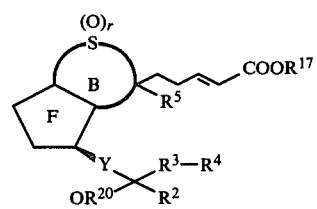   XXI (wherein the various symbols are as hereinbefore defined) by means heretofore mentioned for the conversion of compounds of general formula VIA to those of general formula VA.

Compounds of general formula XXI may be prepared from a compound of the general formula:

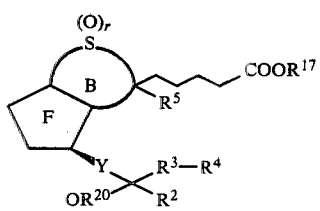

XXII wherein the various symbols are as hereinbefore defined.

Compounds of general formula XXII may be converted to compounds of the general formula:

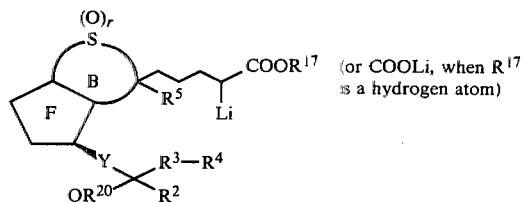

XXIII (or COOLi, when $R^{17}$ is a hydrogen atom)

(wherein the varius symbols are as hereinbefore defined) by reaction with a lithium compound of the general formula:

XXIV (wherein $R^{24}$ and $R^{25}$, which may be the same or different, each represent an alkyl group containing from 1 to 6 carbon atoms, or a cycloalkyl group containing from 3 to 6 carbon atoms), e.g. lithium diisopropylamide, in an inert organic solvent, e.g. tetrahydrofuran, hexamethylphosphoramide (HMPA), diethyl ether, hexane, pentane, or a mixture of two or more of them, at a low temperature, e.g. at 0° to −78° C.

Compounds of general formula XXIII may be converted to compounds of the general formula:

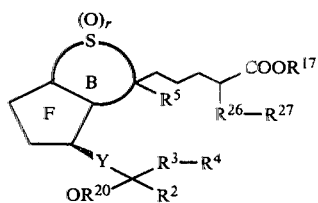

XXV (wherein $R^{26}$ represents a sulphur or selenium atom, $R^{27}$ represents an alkyl group containing from 1 to 4 carbon atoms, or a phenyl group unsubstituted or substituted by one or two chlorine atoms, trifluoromethyl, methoxy or nitro groups, and the other symbols are as hereinbefore defined) by reaction with a phenyl (or substituted-phenyl)seleno bromide or a compound of the general formula:

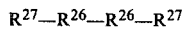

$R^{27}-R^{26}-R^{26}-R^{27}$    XXVI (the symbols $R^{26}$ are both the same, and the symbols $R^{27}$ are both the same, $R^{26}$ and $R^{27}$ being as hereinbefore defined) in an inert organic solvent, e.g. tetrahydrofuran, HMPA, diethyl ether, hexane, pentane, or a mixture of two or more of them, at a temperature from ambient to −78° C., followed by hydrolysis, e.g. with aqueous ammonium chloride.

Compounds of general formula XXV, wherein $R^{26}$ represents a selenium atom, and the other symbols are as hereinbefore defined, may be converted to compounds of general formula XXI by means heretofore mentioned for the conversion of sulphides of general formula VF to sulphoxides of general formula VD or sulphones of general formula VE.

Compounds of general formula XXV, wherein $R^{26}$ represents a sulphur atom, and the other symbols are as hereinbefore defined, may be converted to sulphoxides of the general formula:

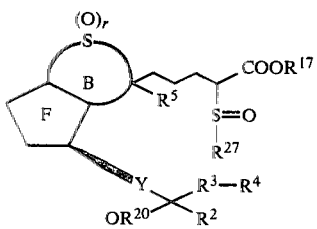

XXVII (wherein the various symbols are as hereinbefore defined) by means heretofore mentioned for the conversion of sulphides of general formula VF to sulphoxides of general formula VD or sulphones of general formula VE.

Sulphoxides of general formula XXVII may be converted to compounds of general formula XXI by reaction in toluene or carbon tetrachloride, advantageously, in the presence of calcium carbonate or trimethyl phosphite, at the reflux temperature of the reaction mixture.

Compounds of general formula XXI, wherein r is 1 or 2, and the other symbols are as hereinbefore defined, may, if desired, be prepared from compounds of general formula XXV, wherein r is zero or 1, and the other symbols are as hereinbefore defined, by means heretofore mentioned for the conversion of compounds of general formula XXV to those of general formula XXI.

Compounds of general formula XXII may be prepared from compounds of the general formula:

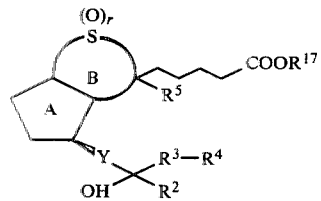

VH

[wherein the various symbols are as hereinbefore defined] by methods known per se for the conversion of a hydroxy group to a protected-hydroxy group. For example, methods for the conversion are described in 'Protective Groups in Organic Chemistry', Chapter 3 (1973), Plenum Press, particularly, ibid, pp. 104–106, for the conversion of a hydroxy group to a tetrahydropyran-2-yloxy group which is preferable as $OR^{20}$. For example, when $OR^{20}$ is a heterocyclic group or an ether group, the conversion may be effected by using 2,3-dihydropyran, 2,3-dihydrofuran, 2,3-dihydrothiopyran, ethyl vinyl ether, 2-methoxypropene, 1-methoxycyclohexene or α-methoxystyrene in an inert organic solvent, e.g. methylene chloride, in the presence of a condensing agent, e.g. p-toluenesulphonic acid, sulphuric acid, trifluoroborane-etherate or phosphorus oxychloride at a temperature from ambient to −30° C., preferably at ambient temperature, or when $R^{20}$ is a tri-substituted silyl group, the reaction may be effected by using a tri-substituted silylating reagent, e.g. trimethylchlorosilane or trimethylsilyldiethylamine in the absence or presence of a tertiary amine, e.g. pyridine or triethylamine in an inert organic solvent, e.g. methylene chloride or acetone at a temperature from ambient to −30° C.

The thio-$PGI_1$ analogues of general formula V, wherein $R^1$ represents a grouping of the formula —$CH_2OR^{11}$, and the other symbols are as hereinbefore defined, i.e. compounds of the general formula:

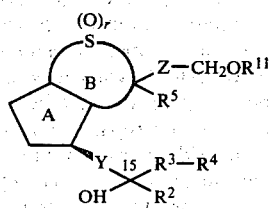

VJ (wherein the various symbols are as hereinbefore defined) are prepared from a compound of the general formula:

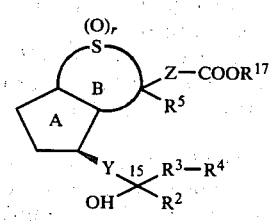

VK (wherein the various symbols are as hereinbefore defined) by reduction to convert the carboxy or ester group —$COOR^{17}$ to a hydroxymethyl group —$CH_2OH$, followed, if desired, by selective acylation of the hydroxymethyl group. Suitable reduction methods for the conversion of a carboxy or ester group to a hydroxymethyl group are well known. For example, the reduction may be effected by using lithiumaluminium hydride or diisobutylaluminium hydride in an inert organic solvent, e.g. tetrahydrofuran, diethyl ether, 1,2-dimethoxyethane, diglyme, hexane, pentane, benzene, toluene, or a mixture of two or more of them, at a temperature from ambient to −78° C.

The selective acylation of the hydroxymethyl group may be effected by using a corresponding acyl halide or acid anhydride in an inert organic solvent, e.g. methylene chloride or pyridine, in the presence of a tertiary amine, e.g. pyridine or triethylamine, at a temperature below ambient, preferably below 0° C.

Compounds of general formula VJ may also be prepared from compounds of general formula VK by reactions as follows:

(1) protection of hydroxy group(s),
(2) reduction of the carboxy or ester group $COOR^{17}$,
(3) if desired, acylation of the hydroxymethyl group thus produced, and
(4) elimination of the hydroxy-protecting group(s).

Each reaction may be carried out by means heretofore described.

The thio-$PGI_1$ analogues of general formula V, wherein $R^1$ represents a grouping of the formula

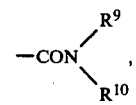

and the other symbols are as hereinbefore defined, i.e. compounds of the general formula:

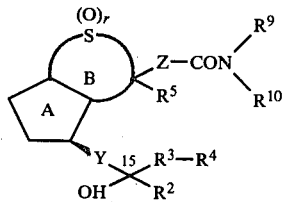

VL (wherein the various symbols are as hereinbefore defined) are prepared by amidation of an activated derivative of an acid of the general formula:

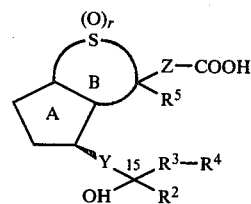

VM

[wherein the various symbols are as hereinbefore defined] with a compound of the general formula:

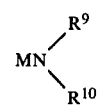

XXVIII wherein M represents an alkali metal, and $R^9$ and $R^{10}$ are as hereinbefore defined.

The reaction is carried out in an inert organic solvent, e.g. methylene chloride, diethyl ether, tetrahydrofuran, 1,2-dimethoxyethane, benzene, toluene, dioxan, acetonitrile, N,N-dimethylformamide, HMPA, or a mixture of two or more of them, at ambient temperature, if desired, with heating or cooling.

Examples of suitable activated derivatives of acids of general formula VM are acid halides, e.g. acid chlorides or acid bromides, acid anhydrides, mixed acid anhydrides with an alkylcarbonate or an inorganic halide, e.g. phosphorus oxychloride or thionyl chloride, or an organic halide, e.g. p-toluenesulphonyl chloride, or activated esters, e.g. p-nitrophenyl ester. Advantageously, the reaction is carried out with triethylamine and isobutyl chloroformate in N,N-dimethylformamide at 0° C., and followed by reaction with a sodium derivative of general formula XXVIII in the presence of HMPA at room temperature. The activated derivatives of acids and compounds of general formula XXVIII may easily be prepared by methods known per se.

Compounds of general formula VL may also be prepared from compounds of general formula VM by reactions as follows:

(1) protection of hydroxy group(s).

(2) amidation and (3) elimination of the hydroxy-protecting group(s).

Each reaction may be carried out by means heretofore described.

The thio-PGI$_1$ analogues of general formula V, wherein $R^1$ represents a grouping of the formula —COOR$^8$, wherein $R^8$ is other than a hydrogen atom, and the other symbols are as hereinbefore defined, are prepared by esterification of acids of general formula VM by methods known per se, for example, when $R^8$ is an alkyl group, by reaction with (1) a diazoalkane, (2) an alkyl halide, or (3) an N,N-dimethylformamide-dialkyl acetal, or when $R^8$ is an alkyl group or any other esterifying group within the definition of $R^8$, (4) using dicyclohexylcarbodiimide (by the procedure described in our Japanese Pat. No. 762305), (5) using a pivaloyl halide (by the procedure described in our British Pat. No. 1,364,125), (6) using an arylsulphonyl or alkylsulphonyl halide (by the procedure described in our British Pat. No. 1,362,956), (7) using isobutyl chloroformate (by the procedure described in British Pat. No. 1,492,439) or (8) using dipyridyl disulphide and triphenylphosphine [by the procedure described in "Tetrahedron Letters", 3409 (1976)].

The preparation of esters using a diazoalkane is carried out by reacting the corresponding acid with an appropriate diazoalkane in an inert organic solvent, e.g. diethyl ether, ethyl acetate, methylene chloride, acetone, methanol, or a mixture of two or more of them, at a temperature from ambient to −10° C., preferably at 0° C. The preparation of esters using an alkyl halide is carried out by reacting the corresponding acid with an appropriate alkyl halide, e.g. methyl iodide, (i) in acetone in the presence of an alkali metal, e.g. potassium or sodium, carbonate [cf. J. Org. Chem., 34, 3717 (1969)], (ii) in N,N-dimethylacetamide or N,N-dimethylformamide in the presence of an alkali metal, e.g. potassium or sodium, bicarbonate [cf. Advan. Org. Chem., 5, 37 (1965)] or (iii) in dimethyl sulphoxide in the presence of calcium oxide [cf. Synthesis, 262 (1972)], at a temperature of 0° to ambient. The preparation of esters using an N,N-dimethylformamide-dialkyl acetal is carried out by reacting the corresponding acid with an N,N-dimethylformamide-dialkyl acetal, e.g. N,N-dimethylformamide-dimethyl acetal, in anhydrous benzene [cf. Helv. Chem. Acta, 48, 1746 (1965)]. The preparation of esters using dicyclohexylcarbodiimide is carried out by reacting the corresponding acid with an appropriate alcohol $R^8$OH, wherein $R^8$ is other than a hydrogen atom, in an inert organic solvent such as a halogenated hydrocarbon, e.g. chloroform or methylene chloride, in the presence of a base such as pyridine or picoline, preferably pyridine, at a temperature of 0° C. to ambient. The preparation of esters using a pivaloyl, arylsulphonyl or alkylsulphonyl halide or isobutyl chloroformate is carried out by reacting the corresponding acid with a tertiary amine, e.g. triethylamine or pyridine, and a pivaloyl halide, e.g. pivaloyl chloride, arylsulphonyl halide, e.g. p-toluenesulphonyl chloride or benzenesulphonyl chloride, alkylsulphonyl halide, e.g. methanesulphonyl chloride or ethanesulphonyl chloride, or isobutyl chloroformate, in the presence or absence of an inert organic solvent such as a halogenated hydrocarbon, e.g. chloroform or methylene chloride, or an ether, e.g. diethyl ether or tetrahydrofuran, to prepare a mixed acid anhydride of the acid, and adding thereto, at a temperature of 0° C. to ambient, an alcohol $R^8$OH, wherein $R^8$ is other than a hydrogen atom, to obtain the desired ester. The preparation of esters using dipyridyl disulphide and triphenylphosphine is carried out by reacting the corresponding acid with an appropriate alcohol $R^8$OH, wherein $R^8$ is other than a hydrogen atom, in an inert organic solvent, e.g. toluene, benzene or xylene, at a temperature from ambient to 80° C.

Starting materials of general formula XII, XIV, XVI or XVII are well known in the field of prostaglandin synthesis, or may easily be prepared from known compounds.

For example, a method for the preparation of starting materials of general formula XII or XIV, wherein the ring F is the grouping of formula A$_2$, utilising known procedures may be represented by the series of reactions depicted schematically below in Scheme C, wherein Ac represents an acetyl group, and the other symbols are as hereinbefore defined.

SCHEME C

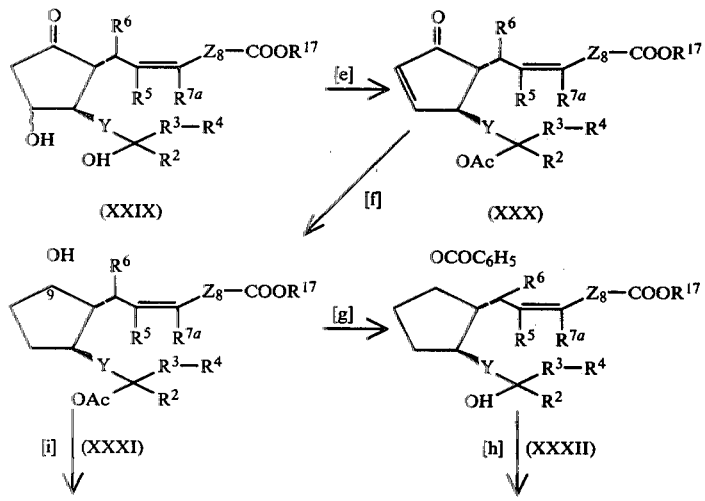

SCHEME C

-continued

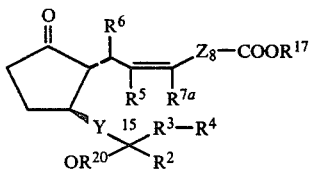
(XIVA)

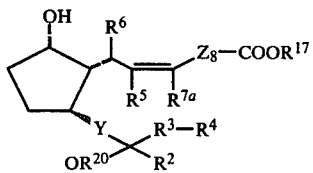
(XIIA)

The various reactions depicted above in Scheme C may be effected by methods known per se. For example, the conversion [e] may be carried out with acetic anhydride in pyridine at 35° C., the conversion [f] may be carried out with sodium borohydride in aqueous methanol at −20° to −30° C., followed if desired, by separation of the resulting 9α- and 9β-hydroxy isomers. The 9β-hydroxy isomer may be converted to compounds of general formula XI, wherein the ring F is a grouping of formula $A_2$, by means as mentioned hereafter for the conversions [g] and [h]. The conversion [g] may be carried out with benzoyl chloride in methylene chloride in the presence of pyridine at room temperature, followed by deacetylation with potassium carbonate in methanol at a temperature of 0° C. to ambient. The conversion [h] may be carried out by means heretofore mentioned for the protection of a hydroxy group, followed by reaction with potassium carbonate in methanol at a temperature above ambient temperature. The conversion [i] may be carried out by oxidation, for example using Collins reagent or Jones reagent, followed by deacetylation and then protection of the 15-hydroxy group.

The starting materials of general formula XXIX are either known or may be prepared by elimination of the hydroxy-protecting groups of the corresponding compounds of general formula XIV by means heretofore mentioned.

Starting materials of general formula XVI or XVII, wherein the ring F is a grouping of formula $A_2$ may be prepared by the procedure depicted in Scheme C.

Starting materials of general formula XII, or XVI, wherein the ring F is a grouping of formula $A_3$ or $A_4$ may be prepared by methods known per se, for example, the method described in Japanese Patent Kokai No. 54-24865, or, when the ring F is a grouping of formula $A_3$, by the method described in J. Amer. Chem. Soc., 96, 6831 (1973), or, when the ring F is a grouping of formula $A_4$, by the method described in Tetrahedron Letters, 4730 (1973).

Starting materials of general formula XIV or XVII, wherein the ring F is a grouping of formula $A_9$ may be prepared by the method described in Tetrahedron Letters, 1957 or 2053 (1975), followed by protection of hydroxy group(s).

Starting materials of general formula XII or XIV, wherein the ring F is a grouping of formula $A_8$ may be prepared by the methods described in the following patent specifications and the chemical literature, or obvious modifications thereof:

(1) when $R^2$ is a hydrogen atom and the grouping —$R^3$—$R^4$ is a pentyl group, as described in J. Amer. Chem. Soc., 91, 5675 (1969) or ibid, 92, 397 (1970);

(2) when $R^2$ is a hydrogen atom or a methyl or ethyl group and the grouping —$R^3$—$R^4$ is an alkyl group, as described in Japanese Patent Kokai Nos. 49-124048, 49-134656, 50-13362, 50-25549, 50-101340 and 51-68547, British Patent Specifications Nos. 1,398,291, 1,450,691 and 1,483,240, and U.S. Patent Specifications Nos. 3,962,312, 3,966,792 and 4,024,174;

(3) when $R^2$ is a hydrogen atom or a methyl or ethyl group, $R^3$ is a single bond or an alkylene group and $R^4$ is an unsubstituted or substituted cycloalkyl group, as described in Japanese Patent Kokai Nos. 50-13364, 50-25549, 50-148339 and 51-68547, British Patent Specifications Nos. 1,450,691, 1,464,916, 1,488,141, 1,483,240, 1,484,210 and 1,545,213, and U.S. Patent Specifications Nos. 3,962,312, 3,966,792, 4,034,003, 4,024,174, 4,045,468 and 4,087,620;

(4) when $R^2$ is a hydrogen atom or a methyl or ethyl group, $R^3$ is a single bond or an alkylene group, and $R^4$ is an unsubstituted or substituted phenyl group, as described in Japanese Patent Kokai Nos. 50-13364, 50-25549 and 51-68547, British Patent Specification No. 1,483,240 and U.S. Patent Specifications Nos. 3,962,312 and 4,024,174;

(5) when $R^2$ is a hydrogen atom or a methyl or ethyl group, $R^3$ is an alkylene group, and $R^4$ is an unsubstituted or substituted phenoxy group, as described in Japanese Patent Kokai Nos. 51-59841 and 52-25745, British Patent Specification No. 1,521,747, and U.S. Patent Specification No. 4,065,632;

(6) when $R^2$ is a hydrogen atom or a methyl or ethyl group, $R^3$ is an alkylene group, and $R^4$ is an alkoxy group or an unsubstituted or substituted cycloalkoxy group, as described in Japanese Patent Kokai Nos. 49-54349, 52-7939 and 52-31054, and British Patent Specifications Nos. 1,456,511, 1,511,261 and 1,515,896;

(7) when $R^2$ is a hydrogen atom, $R^3$ is a single bond, and $R^4$ is a hydrogen atom, from compounds of general formula XXXIII depicted hereafter, which may be prepared as described in British Patent Specification No. 1,482,928, by the series of reactions depicted schematically below in Scheme D, wherein $R^{28}$ represents an alkanoyl group containing from 2 to 5 carbon atoms, and the other symbols are as hereinbefore defined.

SCHEME D

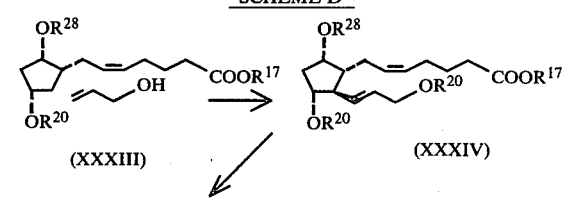
(XXXIII)     (XXXIV)

-continued
SCHEME D

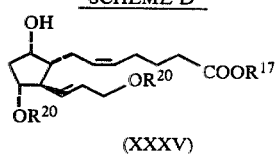

(XXXV)

Compounds of general formula XXXIV may be prepared from compounds of general formula XXXIII by means heretofore mentioned for the protection of hydroxy groups, and may be converted into compounds of general formula XXXV by hydrolysis under alkaline conditions, which may be effected with anhydrous potassium carbonate in an anhydrous alkanol containing at most four carbon atoms, preferably absolute methanol.

Starting materials of general formula XVI or XVII may be prepared by the methods described in 'Advances in Prostaglandin and Thromboxane Research' vol. 1, page 195 et seq, Raven Press, New York (1976), or in Japanese Patent Kokai No. 53-112877.

Starting materials of general formula XII or XIV when $Z_8$ is a grouping of formula $Z_{10}$, $Z_{11}$ or $Z_{12}$, may be prepared by the methods described in Japanese Patent Specification No. 773209, and, when $R^6$ is a methyl or ethyl group, in Japanese Patent Kokai No. 51-1448.

Starting materials of general formula XII, wherein the ring F is a grouping of formula $A_8$, $R^5$ or $R^{7a}$ is a methyl or ethyl group, $Z_8$ is a grouping of formula $Z_9$, in which m is 4, and the other symbols are as hereinbefore defined, may be prepared by the series of reactions depicted schematically below in Scheme E, wherein $R^{5a}$ or $R^{7b}$ represents a methyl or ethyl group, $R^{29}$ represents a methyl or ethyl group, the double bond between $C_5$ and $C_6$ is cis, and the other symbols are as hereinbefore defined.

SCHEME E

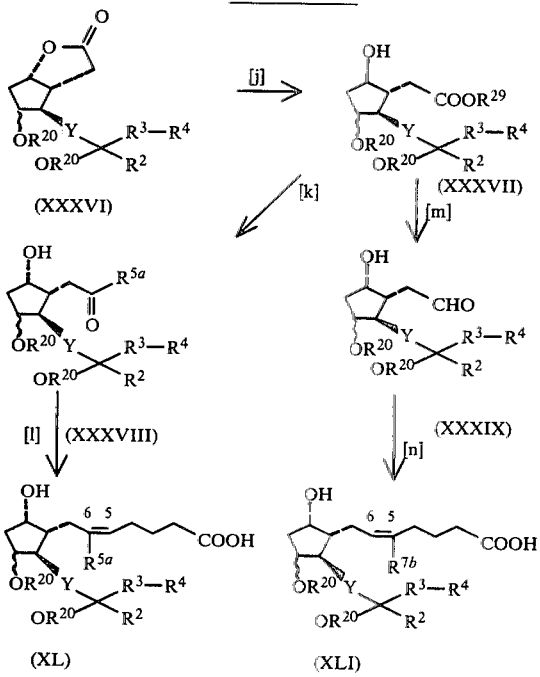

Referring to Scheme E, the conversion [j] may be carried out by saponification as described hereafter, followed by esterification as described hereinbefore.

The conversion [k] may be carried out by the method described in J.Org.Chem., 31,2355 (1966), ibid. 33,6 (1968) or J. Amer. Chem. Soc., 87, 1345 (1965). The conversion [l] may be carried out by the Wittig reaction with an ylide solution [prepared from dimsyl sodium and (4-carboxybutyl)triphenylphosphonium bromide]. The method for the Wittig reaction is described in 'Organic Reactions', 14, Chapter 3 (1965), John Wiley & Sons, Inc. Preferably the Wittig reaction is carried out in an inert organic solvent such as dimethyl sulphoxide, normally at a temperature of 10° to 60° C. The conversion [m] may be carried out with diisobutylaluminium hydride in toluene at a temperature below 0° C., preferably at −60° to −78° C. The conversion [n] may be carried out by the Wittig reaction with an ylide solution [prepared from dimsyl sodium and (5-carboxy-2-pentyl)triphenylphosphonium bromide or (6-carboxy-3-hexyl)triphenylphosphonium bromide] under the same condition as described for the conversion [l].

Starting materials of general formula XII, wherein the ring F is other than a grouping of formula $A_8$, or starting materials of general formula XVI may be prepared from the corresponding lactone by the procedure described in Scheme E.

Starting materials of general formula XII, XIV, XVI or XVII may be prepared, when Y represents the ethylene or trans-vinylene group, by the methods described in the aforementioned patent specifications or literature references, and, when Y represents the ethynylene group, by the method described in The Synthesis of Prostaglandins', page 379, John Wiley & Sons, Inc. (USA) or 'Prostaglandin Synthesis' page 465, Academic Press, Inc. (USA), and, when Y represents the cis-vinylene group, by methods known per se for the conversion of an ethynylene group into a cis-vinylene group, for example the method described in J. Amer. Chem. Soc., 78, 2518 (1956).

Acids of the thio-PGI$_1$ analogues of general formula V, wherein $R^1$ represents the grouping of formula —COOR$^8$, wherein $R^8$ represents a hydrogen atom, and the other symbols are as hereinbefore defined, i.e. compounds of general formula VM may be prepared by saponification of the corresponding ester of general formula V, wherein $R^1$ represents a grouping of formula —COOR$^8$, wherein $R^8$ is other than a hydrogen atom, and the other symbols are as hereinbefore defined, by methods known per se. For example, methods for the saponification are descried in 'Compendium of Organic Synthetic Methods', Volume 1(1971), 2(1974) or 3(1977), Section 23, John Wiley & Sons, Inc. (USA); advantageously, the saponification may be effected by using an aqueous solution of an alkali metal, e.g. sodium, potassium or lithium, hydroxide or carbonate, or an alkaline earth metal, e.g. calcium or barium, hydroxide or carbonate in the absence or presence of a water miscible solvent such as an ether, e.g. dioxan or tetrahydrofuran, or a lower alkanol, e.g. methanol or ethanol, at a temperature of −10° to 100° C., preferably at ambient temperature, or using an anhydrous solution of alkali metal, e.g. sodium, potassium or lithium, hydroxide or carbonate in an anhydrous lower alkanol, e.g. absolute methanol or ethanol, at a temperature of −10° to 100° C., preferably at ambient temperature.

Cyclodextrin clathrates of the thio-prostaglandin I$_1$ analogues of general formula V may be prepared by dissolving the cyclodextrin in water or an organic solvent which is miscible with water in the absence or presence of triethylamine and adding to the solution of the thio-prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. α-, β- or γ-Cyclodextrins or mixtures thereof may be used in the preparation of the cyclodextrin clathrates. Conversion into cyclodextrin clathrates serves to increase the stability of the thio-prostaglandin $I_1$ analogues of general formula V.

Compounds of general formula V, wherein $R^1$ is a grouping of the formula —$COOR^8$, wherein $R^8$ represents a hydrogen atom, may, if desired, be converted by methods known per se into salts. Preferably, the salts are non-toxic salts. By the term 'non-toxic salts', as used in this specification, is meant salts the cations (or in the case of acid addition salts referred to hereinafter the anions) of which are relatively innocuous to the animal organism when used in therapeutic doses so that the beneficial pharmacological properties of the compounds of general formula V are not vitiated by side-effects ascribable to those cations (or anions). Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example alkyl groups containing from 1 to 6 carbon atoms and hydroxyalkyl groups containing 2 or 3 carbon atoms. Suitable non-toxic amine salts are, e.g. tetraalkylammonium, such as tetramethylammonium salts, and other organic amine salts such as methylamine salts, dimethylamine salts, cyclopentylamine salts, benzylamine salts, phenethylamine salts, piperidine salts, monoethanolamine salts, diethanolamine salts, lysine salts and arginine salts.

Salts may be prepared from the acids of general formula V, wherein $R^1$ represents a grouping of the formula —$COOR^8$, wherein $R^8$ represents a hydrogen atom, by methods known per se, for example by reaction of stoichiometric quantities of an acid of general formula V and the appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary after removal of part of the solvent.

When the thio-prostaglandin $I_1$ analogues of general formula V contain an amino group the compounds may, if desired, be converted by methods known per se into acid addition salts, which are preferably non-toxic as hereinbefore defined.

Acid addition salts may be prepared from the compounds of general formula V by methods known per se, for example by reaction of stoichiometric quantities of a compound of general formula V and the appropriate acid, e.g. an inorganic acid such as hydrochloric acid, hydrobromic acid, hydroiodic acid, sulphuric acid, phosphoric acid or nitric acid, or an organic acid such as acetic acid, propionic acid, lactic acid, tartaric acid, citric acid, methanesulphonic acid, ethanesulphonic acid, benzenesulphonic acid, toluenesulphonic acid, isethionic acid, or succinic acid, in a suitable solvent. The acid addition salts may be purified by recrystallisation from a suitable solvent or suitable mixture of two or more solvents.

Preferred thio-$PGI_1$, analogues of the present invention are as follows [abbreviating (13E)-(6RS,9α,11α,15S)-6,9-epithio-11,15-dihydroxyprost-13-enoic acid to thio-$PGI_1$]:

thio-$PGI_1$,
2-methyl-thio-$PGI_1$,
3-methyl-thio-$PGI_1$,
4-methyl-thio-$PGI_1$,
5-methyl-thio-$PGI_1$,
6-methyl-thio-$PGI_1$,
7-methyl-thio-$PGI_1$,
16-methyl-thio-$PGI_1$,
17-methyl-thio-$PGI_1$,
18-methyl-thio-$PGI_1$,
19-methyl-thio-$PGI_1$,
20-methyl-thio-$PGI_1$,
16,16-dimethyl-thio-$PGI_1$,
16,17-dimethyl-thio-$PGI_1$,
16,19-dimethyl-thio-$PGI_1$,
16-ethyl-thio-$PGI_1$,
17-ethyl-thio-$PGI_1$,
16-propyl-thio-$PGI_1$,
17-propyl-thio-$PGI_1$,
16,20-dimethyl-thio-$PGI_1$,
17,20-dimethyl-thio-$PGI_1$,
16,16,20-trimethyl-thio-$PGI_1$,
16-ethyl-20-methyl-thio-$PGI_1$,
17-ethyl-20-methyl-thio-$PGI_1$,
20-ethyl-thio-$PGI_1$,
17,20-diethyl-thio-$PGI_1$,
20-butyl-thio-$PGI_1$,
20-hexyl-thio-$PGI_1$,
15-cyclobutyl-16,17,18,19,20-pentanor-thio-$PGI_1$,
15-(1-propylcyclobutyl)-16,17,18,19,20-pentanor-thio-$PGI_1$,
15-(1-butylcyclobutyl)-16,17,18,19,20-pentanor-thio-$PGI_1$,
15-(1-pentylcyclobutyl)-16,17,18,19,20-pentanor-thio-$PGI_1$,
15-(1-hexylcyclobutyl)-16,17,18,19,20-pentanor-thio-$PGI_1$,
15-(2-methylcyclobutyl)-16,17,18,19,20-pentanor-thio-$PGI_1$,
15-(2-propylcyclobutyl)-16,17,18,19,20-pentanor-thio-$PGI_1$,
15-(3-ethylcyclobutyl)-16,17,18,19,20-pentanor-thio-$PGI_1$,
15-(3-propylcyclobutyl)-16,17,18,19,20-pentanor-thio-$PGI_1$,
15-(2,3,4-triethylcyclobutyl)-16,17,18,19,20-pentanor-thio-$PGI_1$,
15-cyclopentyl-16,17,18,19,20-pentanor-thio-$PGI_1$, 16-cyclopentyl-17,18,19,20-tetranor-thio-$PGI_1$,
16-cyclopentyl-18,19,20-trinor-thio-$PGI_1$,
17-cyclopentyl-18,19,20-trinor-thio-$PGI_1$,
17-cyclopentyl-19,20-dinor-thio-$PGI_1$,
18-cyclopentyl-19,20-dinor-thio-$PGI_1$,
15-(2-pentylcyclopentyl)-16,17,18,19,20-pentanor-thio-$PGI_1$, 15-(2,2-dimethylcyclopentyl)-16,17,18,19,20-pentanor-thio-PGI$_1$,
15-(3-ethylcyclopentyl)-16,17,18,19,20-pentanor-thio-PGI$_1$,
15-(3-propylcyclopentyl)-16,17,18,19,20-pentanor-thio-PGI$_1$,
15-(3-butylcyclopentyl)-16,17,18,19,20-pentanor-thio-PGI$_1$,
15-(3-tert-butylcyclopentyl)-16,17,18,19,20-pentanor-thio-PGI$_1$,
15-(1-methyl-3-propylcyclopentyl)-16,17,18,19,20-pentanor-thio-PGI$_1$,
15-(2-methyl-3-propylcyclopentyl)-16,17,18,19,20-pentanor-thio-PGI$_1$,
15-(2-methyl-4-propylcyclopentyl)-16,17,18,19,20-pentanor-thio-PGI$_1$,
15-cyclohexyl-16,17,18,19,20-pentanor-thio-PGI$_1$,
16-cyclohexyl-17,18,19,20-tetranor-thio-PGI$_1$,
16-cyclohexyl-18,19,20-trinor-thio-PGI$_1$,
17-cyclohexyl-18,19,20-trinor-thio-PGI$_1$,
18-cyclohexyl-19,20-dinor-thio-PGI$_1$,
16-methyl-17-cyclohexyl-18,19,20-trinor-thio-PGI$_1$,
17-cyclohexyl-19,20-dinor-thio-PGI$_1$,
16-methyl-16-cyclohexyl-18,19,20-trinor-thio-PGI$_1$,
19-cyclohexyl-20-nor-thio-PGI$_1$,
15-(3-ethylcyclohexyl)-16,17,18,19,20-pentanor-thio-PGI$_1$,
15-(3-isopropylcyclohexyl)-16,17,18,19,20-pentanor-thio-PGI$_1$,
15-(4-methylcyclohexyl)-16,17,18,19,20-pentanor-thio-PGI$_1$,
15-(4-ethylcyclohexyl)-16,17,18,19,20-pentanor-thio-PGI$_1$,
15-(4-propylcyclohexyl)-16,17,18,19,20-pentanor-thio-PGI$_1$,
15-(4-tert-butylcyclohexyl)-16,17,18,19,20-pentanor-thio-PGI$_1$,
15-(2,6-dimethylcyclohexyl)-16,17,18,19,20-pentanor-thio-PGI$_1$,
15-(2,2-dimethylcyclohexyl)-16,17,18,19,20-pentanor-thio-PGI$_1$,
15-(2,6-dimethyl-4-propylcyclohexyl)-16,17,18,19,20-pentanor-thio-PGI$_1$,
16-(1-methylcyclohexyl)-17,18,19,20-tetranor-thio-PGI$_1$,
15-cycloheptyl-16,17,18,19,20-pentanor-thio-PGI$_1$,
16-cycloheptyl-17,18,19,20-tetranor-thio-PGI$_1$,
16-cycloheptyl-18,19,20-trinor-thio-PGI$_1$,
17-cycloheptyl-18,19,20-trinor-thio-PGI$_1$,
15-phenyl-16,17,18,19,20-pentanor-thio-PGI$_1$,
16-phenyl-17,18,19,20-tetranor-thio-PGI$_1$,
16-phenyl-18,19,20-trinor-thio-PGI$_1$,
17-phenyl-18,19,20-trinor-thio-PGI$_1$,
18-phenyl-19,20-dinor-thio-PGI$_1$,
19-phenyl-20-nor-thio-PGI$_1$,
20-phenyl-thio-PGI$_1$,
16-methyl-17-phenyl-18,19,20-trinor-thio-PGI$_1$,
16,16-dimethyl-17-phenyl-18,19,20-trinor-thio-PGI$_1$,
16-methyl-16-phenyl-18,19,20-trinor-thio-PGI$_1$,
16-phenyl-thio-PGI$_1$,
16-phenoxy-17,18,19,20-tetranor-thio-PGI$_1$,
17-phenoxy-18,19,20-trinor-thio-PGI$_1$,
18-phenoxy-19,20-dinor-thio-PGI$_1$,
19-phenoxy-20-nor-thio-PGI$_1$,
20-phenoxy-thio-PGI$_1$,
16-(3-chlorophenoxy)-17,18,19,20-tetranor-thio-PGI$_1$,
16-(4-chlorophenoxy)-17,18,19,20-tetranor-thio-PGI$_1$,
16-(4-fluorophenoxy)-17,18,19,20-tetranor-thio-PGI$_1$,
16-(3-trifluoromethylphenoxy)-17,18,19,20-tetranor-thio-PGI$_1$,
16-(2-methylphenoxy)-17,18,19,20-tetranor-thio-PGI$_1$,
16-(3-methylphenoxy)-17,18,19,20-tetranor-thio-PGI$_1$,
16-(4-methylphenoxy)-17,18,19,20-tetranor-thio-PGI$_1$,
16-(4-ethylphenoxy)-17,18,19,20-tetranor-thio-PGI$_1$,
16-(4-tert-butylphenoxy)-17,18,19,20-tetranor-thio-PGI$_1$,
16-(4-sec-butylphenoxy)-17,18,19,20-tetranor-thio-PGI$_1$,
16-propoxy-17,18,19,20-tetranor-thio-PGI$_1$,
16-isopropoxy-17,18,19,20-tetranor-thio-PGI$_1$,
16-butoxy-17,18,19,20-tetranor-thio-PGI$_1$,
16-pentyloxy-17,18,19,20-tetranor-thio-PGI$_1$,
16-hexyloxy-17,18,19,20-tetranor-thio-PGI$_1$,
16-ethoxy-18,19,20-trinor-thio-PGI$_1$,
16-propoxy-18,19,20-trinor-thio-PGI$_1$,
16-isopropoxy-18,19,20-trinor-thio-PGI$_1$,
16-neopentyloxy-18,19,20-trinor-thio-PGI$_1$,
16-pentyloxy-18,19,20-trinor-thio-PGI$_1$,
16-ethoxy-16-methyl-18,19,20-trinor-thio-PGI$_1$,
16-propoxy-16-methyl-18,19,20-trinor-thio-PGI$_1$,
16-isobutoxy-16-methyl-18,19,20-trinor-thio-PGI$_1$,
16-methyl-16-neopentyloxy-18,19,20-trinor-thio-PGI$_1$,
16-butoxy-16-methyl-18,19,20-trinor-thio-PGI$_1$,
16-isopentyloxy-16-methyl-18,19,20-trinor-thio-PGI$_1$,
16-methyl-16-pentyloxy-18,19,20-trinor-thio-PGI$_1$,
17-ethoxy-18,19,20-trinor-thio-PGI$_1$,
17-propoxy-18,19,20-trinor-thio-PGI$_1$,
17-butoxy-18,19,20-trinor-thio-PGI$_1$,
17-(2-ethylbutoxy)-18,19,20-trinor-thio-PGI$_1$,
17-pentyloxy-18,19,20-trinor-thio-PGI$_1$,
16-ethoxy-19,20-dinor-thio-PGI$_1$,
16-propoxy-19,20-dinor-thio-PGI$_1$,
16-(2-methylbutoxy)-19,20-dinor-thio-PGI$_1$,
16-pentyloxy-19,20-dinor-thio-PGI$_1$,
17-methoxy-19,20-dinor-thio-PGI$_1$,
18-methoxy-19,20-dinor-thio-PGI$_1$,
18-ethoxy-19,20-dinor-thio-PGI$_1$,
18-propoxy-19,20-dinor-thio-PGI$_1$,
18-sec-butoxy-19,20-dinor-thio-PGI$_1$,
18-isobutoxy-19,20-dinor-thio-PGI$_1$,
18-butoxy-19,20-dinor-thio-PGI$_1$,
16-methyl-17-methoxy-18,19,20-trinor-thio-PGI$_1$,
16-methyl-17-ethoxy-18,19,20-trinor-thio-PGI$_1$,
16-methyl-17-isobutoxy-18,19,20-trinor-thio-PGI$_1$,
16-pentyloxy-20-nor-thio-PGI$_1$,
16-pentyloxy-17-methyl-19,20-dinor-thio-PGI$_1$,
19-methoxy-20-nor-thio-PGI$_1$,
19-ethoxy-20-nor-thio-PGI$_1$,
19-propoxy-20-nor-thio-PGI$_1$,
16-methyl-18-methoxy-19,20-dinor-thio-PGI$_1$,
16-methyl-18-propoxy-19,20-dinor-thio-PGI$_1$,
17-methyl-18-methoxy-19,20-dinor-thio-PGI$_1$,
16,16-dimethyl-17-ethoxy-18,19,20-trinor-thio-PGI$_1$,
16,16-dimethyl-17-propoxy-18,19,20-trinor-thio-PGI$_1$,
16,16-dimethyl-17-isobutoxy-18,19,20-trinor-thio-PGI$_1$,
20-methoxy-thio-PGI$_1$,
20-ethoxy-thio-PGI$_1$,
16-pentyloxy-thio-PGI$_1$,
16-ethyl-18-propoxy-19,20-dinor-thio-PGI$_1$,
16-cyclobutoxy-17,18,19,20-tetranor-thio-PGI$_1$,
16-cyclopentyloxy-17,18,19,20-tetranor-thio-PGI$_1$,
16-cyclohexyloxy-17,18,19,20-tetranor-thio-PGI$_1$,
16-cycloheptyloxy-17,18,19,20-tetranor-thio-PGI$_1$,
17-cyclopentyloxy-18,19,20-trinor-thio-PGI$_1$,
17-cyclohexyloxy-18,19,20-trinor-thio-PGI$_1$, the corresponding 15-methyl and 15-ethyl analogues and corresponding (6R)-isomers and (6S)-isomers, and corresponding 13,14-dihydro, 13,14-didehydro, 11-deoxy, cis-13 and trans-2 analogues, and esters, amides, alcohols, cyclodextrin clathrates, non-toxic salts, and non-toxic acid addition salts thereof, and their 5,9-epithio analogues, and the corresponding sulphinyl and sulphonyl analogues.

Particularly preferred thio-PGI$_1$, analogues of the present invention are the esters: (13E)-(6RS,9α,11α,15R)-6,9-epithio-11,15-dihydroxy-15-(1-butylcyclobutyl)-16,17,18,19,20-pentanorprost-13-enoic acid methyl ester, (13E)-(6RS,9α,11α,15R)-6,9-epithio-11,15-dihydroxy-16,16-dimethylprost-13-enoic acid methyl ester, (13E)-(6RS,9α,11α,15S,16S)-6,9-epithio-11,15-dihydroxy-16-methylprost-13-enoic acid methyl ester, (13E)-(6RS, 9α,11α,15R,)-6,9-epithio-11,15-dihydroxy-16-(4-chlorophenoxy)-17,18,19,20-tetranorprost-13-enoic acid methyl ester, (13E)-(6RS,9α,11α,15S,16R)-6,9-epithio-11,15-dihydroxy-16-methylprost-13-enoic acid methyl ester, (13E)-(6RS,9α,15S)-6,9-epithio-15-hydroxyprost-13-enoic acid methyl ester, (13E)-(5RS,9α,11α,15S)-5,9-epithio-11,15-dihydroxyprost-13-enoic acid methyl ester, (13E)-(6RS,9α,11α,15S)-6,9-epithio-11,15-dihydroxyprost-13-enoic acid methyl ester, (13E)-(6R,9α,11α,15S)-6,9-epithio-11,15-dihydroxyprost-13-enoic acid methyl ester, (13E)-(6S,9α,11α,15S)-6,9-epithio-11,15-dihydroxyprost-13-enoic acid methyl ester, (2E,13E)-(6RS,9α,11α,15S)-6,9-epithio-11,15-dihydroxyprosta-2,13-dienoic acid methyl ester, (2E,13E)-(6RS,9α,11α,15S)-6,9-sulphinyl-11,15-dihydroxyprosta-2,13-dienoic acid methyl ester, (2E,13E)-(6RS,9α,11α,15S)-6,9-sulphonyl-11,15-dihydroxyprosta-2,13-dienoic acid methyl ester, (13E)-(6RS,9α,11α,15S)-6,9-sulphinyl-11,15-dihydroxyprost-13-enoic acid methyl ester, (13E)-(6RS,9α,11α,15S)-6,9-sulphonyl-11,15-dihydroxyprost-13-enoic acid methyl ester, (13E)-(6RS,9α,11α,15S,16R)-6,9-sulphonyl-11,15-dihydroxy-16-methylprost-13-enoic acid methyl ester, (13E)-(6RS,9α,11α,15S)-6,9-epithio-11,15-dihydroxyprost-13-enoic acid decyl ester, (13E)-(6RS,9α,11α,15S)-6,9-epithio-11,15-dihydroxyprost-13-enoic acid 2-hydroxyethyl ester, (13E)-(6RS,9α,11α,15S)-6,9-epithio-11,15-dihydroxyprost-13-enoic acid 4-ethylphenyl ester, (13E)-(6RS,9α,11α,15S)-6,9-epithio-11,15-dihydroxyprost-13-enoic acid 4-benzoylaminophenyl ester, (13E)-(6RS,9α,11α,15S)-6,9-epithio-11,15-dihydroxyprost-13-enoic acid 4-methylthiophenyl ester, (13E)-(6RS,9α,11α,15S)-6,9-epithio-11,15-dihydroxyprost-13-enoic acid 2,3-dihydroxypropyl ester, (13E)-(6RS,9α,11α,15S)-6,9-epithio-11,15-dihydroxyprost-13-enoic acid 2-ethylthioethyl ester, (13E)-(6RS,9α,11α,15S)-6,9-epithio-11,15-dihydroxyprost-13-enoic acid furfuryl ester, (13E)-(6RS,9α,11α,15S)-6,9-epithio-11,15-dihydroxyprost-13-enoic acid tetrahydrofurfuryl ester, (13E)-(6RS,9α,11α,15S)-6,9-epithio-11,15-dihydroxyprost-13-enoic acid phthalid-3-yl ester, (13E)-(6RS,9α,11α,15S)-6,9-epithio-11,15-dihydroxyprost-13-enoic acid 4-semicarbazonotolyl ester, and (13E)-(6RS,9α,11α,15S)-6,9-epithio-11,15-dihydroxyprost-13-enoic acid 1,3bisstearoyloxy-2-propyl ester; the amide: (13E)-(6RS,9α,11α,15S)-N-methanesulphonyl-6,9-epithio-11,15-dihydroprost-13-en-1-amide, and the acid: (13E)-(6RS,9α,11α,15S)-6,9-epithio-11,15-dihydroxyprost-13-enoic acid, and cyclodextrin clathrates, non-toxic salts and non-toxic acid additions salts thereof.

The following Reference Examples and Examples illustrate the preparation of thio-prostaglandin I$_1$ analogues of the present invention. In the Reference Examples and Examples 'TLC', 'IR', 'NMR' and 'MS' represent respectively 'Thin layer chromatography', 'Infrared absorption spectrum', 'Nuclear magnetic resonance spectrum' and 'Mass spectrum'. Where solvent ratios are specified in chromatographic separations, the ratios are by volume: the solvents in parentheses show the developing solvent used. Except when specified otherwise, infrared spectra are recorded by the liquid film method, and nuclear magnetic resonance spectra are recorded in deuterochloroform (CDCl$_3$) solution.

REFERENCE EXAMPLE 1

(5Z,13E)-(9α,11α,15R)-9-Hydroxy-11,15-bis(tetrahydropyran-2-yloxy)-16-(4-chlorophenoxy)-17,18,19,20-tetranorprosta-5,13-dienoic acid methyl ester A mixture of 1.76 g of (5Z,13E)-(9α,11α,15R)-9-acetoxy-11-(tetrahydropyran-2-yloxy)-15-hydroxy-16-(4-chlorophenoxy)-17,18,19,20-tetranorprosta-5,13-dienoic acid methyl ester (prepared as described in Reference Example 21 of British Patent Specification No. 1521747), 6 mg of p-toluenesulphonic acid, 0.27 ml of 2,3-dihydropyran and 10 ml of methylene chloride was stirred at room temperature for 10 minutes. The reaction mixture was alkalinized to pH 8 with a saturated aqueous solution of sodium bicarbonate, and extracted with ethyl acetate. The extract was washed with a saturated aqueous solution of sodium chloride, dried over magnesium sulphate and concentrated under reduced pressure to give (5Z,13E)-(9α,11α,15R)-9-acetoxy-11,15-bis-(tetrahydropyran-2-yloxy)-16-(4-chlorophenoxy)-17,18,19,20-tetranorprosta-5,13-dienoic acid methyl ester having the following physical characteristic: TLC (cyclohexane:ethyl acetate=1:1): Rf=0.54.

A solution of the compound thus obtained in 20 ml of methanol was stirred with 516 mg of potassium carbonate at 50° to 55° C. for one hour. The reaction mixture was acidified to pH 4 with acetic acid, and concentrated under reduced pressure. The residue was dissolved in ethyl acetate, washed with water, a saturated aqueous solution of sodium bicarbonate, and a saturated aqueous solution of sodium chloride, dried over magnesium sulphate and concentrated under reduced pressure. The residue was purified by column chromatography on silica gel using a mixture of cyclohexane and ethyl acetate (3:1) as eluent to give 1.58 g of the title compound having the following physical characteristics: TLC (cyclohexane:ethyl acetate=1:1): Rf=0.40; IR: ν=1740 cm$^{-1}$;

NMR: δ=7.13(2H,d), 6.73(2H,d), 5.75–5.20(4H,m), 3.58(3H,s).

REFERENCE EXAMPLE 2

(5Z,13E)-(9α,11α,15R)-9-Hydroxy-11,15-bis(tetrahydropyran-2-yloxy)-15-(1butylcyclobutyl)-16,17,18,19,20-pentanorprosta-5,13-dienoic acid methyl ester An ethereal solution of diazomethane was added to a solution of 740 mg of (5Z,13E)-(9α,11α,15R)-9-hydroxy-11,15-bis(tetrahydropyran-2-yloxy)-15-(1-butylcyclobutyl)-16,17,18,19,20-pentanorprosta-5,13-dienoic acid (prepared as described in Example 1 of British Patent Specification No. 1484210) in 10 ml of diethyl ether until the solution was coloured pale yellow, and the solution was then concentrated under reduced pressure. The residue was purified by column chromatography on silica gel using a mixture of cyclohexane and ethyl acetate (6:1) as eluent to give 500 mg of the title compound having the following physical characteristics: TLC (cyclohexane:ethyl acetate=1:1): Rf=0.54; NMR: δ=5.70–5.20(4H,m), 4.60(2H,m), 3.60(3H,s), 0.90(3H,m).

The following compounds were prepared from the corresponding acid compounds by the procedure described above.

(A) (5Z,13E)-(9α,11α,15R)-9-Hydroxy-11,15-bis(tetrahydropyran-2-yloxy)-16,16-dimethylprosta-5,13dienoic acid methyl ester using as starting material (5Z,13E)-(9α,11α,15R)-9-hydroxy-11,15-bis(tetrahydropyran-2-yloxy)- 16,16-dimethylprosta-5,13-dienoic acid (prepared as described in Example 1 of British Patent Specification No. 1398291).

TLC (cyclohexane:ethyl acetate=2:1): Rf=0.49.

(B) (5Z,13E)-(9α,11α,15S,16S)-9-Hydroxy-11,15-bis-(tetrahydropyran-2-yloxy)-16-methylprosta-5,13-dienoic acid methyl ester using as starting material (5Z,13E)-(9α,11α,15S,16S)-9-hydroxy-11,15-bis(tetrahydropyran-2-yloxy)-16-methylprosta-15,13-dienoic acid (prepared as described in Example 1 of British Patent Specification No. 1398291).

TLC (benzene:ethyl acetate=2:1): Rf=0.39.

(C) (5Z,13E)-(9α,11α,15S,16R)-9-Hydroxy-11,15-bis(tetrahydropyran-2-yloxy)-16-methylprosta-5,13-dienoic acid methyl ester using as starting material (5Z,13E)-(9α,11α,15S,16R)-9-hydroxy-11,15-bis(tetrahydropyran-2-yloxy)-16-methylprosta-5,13-dienoic acid (prepared as described in Example 1 of British Patent Spcification No. 1398291).

TLC (methylene chloride: ethyl acetate=4:1): Rf=0.45.

REFERENCE EXAMPLE 3

(5Z,13E)-(9β,11α,15R)-9-Formyloxy-11,15-bis(tetrahydropyran-2-yloxy)-15-(1-butylcyclobutyl)-16,17,18,19,20-pentanorprosta-5,13-dienoic acid methyl ester Under an atmosphere of nitrogen, to a mixture of 500 mg of the hydroxy compound (prepared as described in Reference Example 2), 456 mg of triphenylphosphine, 80 mg of formic acid and 8 ml of tetrahydrofuran, was added dropwise a solution of 0.273 ml of diethyl azodicarboxylate in 0.7 ml of tetrahydrofuran at 0° C., and the mixture was stirred at that temperature for 2 hours. The reaction mixture was poured into a saturated aqueous solution of sodium bicarbonate, then extracted with ethyl acetate. The extract was washed with water, and a saturated aqueous solution of sodium chloride, dried over magnesium sulphate and concentrated under reduced pressure. The residue was purified by column chromatography on silica gel using a mixture of cyclohexane and ethyl acetate (7:1) as eluent to give 380 mg of the title compound having the following physical characteristics:

TLC (cyclohexane:ethyl acetate=2:1): Rf=0.57;
IR: ν=1730, 1440, 1180, 1025, 975 cm$^{-1}$;
NMR: δ=7.85(1H,s), 5.70–5.20(4H,m), 4.95(1H,m), 4.60(2H,m), 3.60(3H,s), 0.90(3H,m).

The following compounds were prepared from the corresponding hydroxy compounds, prepared as described in Reference Example 1 or 2, by the procedure described above.

(A) (5Z,13E)-(9β,11α,15R)-9-Formyloxy-11,15-bis-(tetrahydropyran-2-yloxy)-16,16-dimethylprosta-5,13-dienoic acid methyl ester from the product of Reference Example 2(A).

TLC (cyclohexane:ethyl acetate=2:1): Rf=0.69;
IR: ν=3030, 2950, 2850, 1740, 1730, 1470, 1450, 1440, 1360, 1320, 1240, 1200, 1170, 1130, 1120, 1080, 1020, 975 cm$^{-1}$;
NMR: δ=7.95(1H,s), 5.75–5.20(4H,m), 5.20–4.73(1H,m), 4.73–4.40(2H,m), 4.40–3.00(9H,m), 1.20–0.80(9H,m).

(B) (5Z,13E)-(9β,11α,15S,16S)-9-Formyloxy-11,15-bis-(tetrahydropyran-2-yloxy)-16-methylprosta-5,13-dienoic acid methyl ester from the product of Reference Example 2(B).

TLC (benzene:ethyl acetate=4.1): Rf=0.60;
IR: ν=2960, 2880, 1735, 1445, 1210, 1180, 1140, 1085, 1030, 980 cm$^{-1}$;
NMR(CCl$_4$ solution): δ=7.80(1H,s), 5.60–5.10(4H,m), 5.10–4.70(1H,m), 4.70–4.40(2H,m), 3.55(3H,s), 1.10–0.70(6H,m).

(C) (5Z,13E)-(9β,11α,15R)-9-Formyloxy-11,15-bis(-tetrahydropyran-2-yloxy)-16-(4-chlorophenoxy)-17,18,19,20-tetranorprosta-5,13-dienoic acid methyl ester from the product of Reference Example 1.

TLC (cyclohexane:ethyl acetate=2:1): Rf=0.51;
IR: ν=1740, 1732 cm$^{-1}$;
NMR: δ=7.90(1H,s), 7.15(2H,d), 6.75(2H,d), 5.76–5.20(4H,m), 5.08(1H,m), 3.60(3H,s).

(D) (5Z,13E)-(9β,11α,15S,16R)-9-Formyloxy-11,15-bis-(tetrahydropyran-2-yloxy)-16-methylprosta-5,13-dienoic acid methyl ester from the product of Reference Example 2(C).

TLC (cyclohexane:ethyl acetate=4:1): Rf=0.35;
IR: ν=2950, 2875, 1740, 1440, 1370, 1175, 1080, 1020, 970 cm$^{-1}$;
NMR(CCl$_4$ solution): δ=7.80(1H, broad s), 6.10–4.33(7H,m), 3.56(3H,s), 4.33–2.90(6H,m), 1.1–0.50(6H,m).

(E) (4Z,13E)-(9β11α,15S)-9-Formyloxy-11,15-bis(-tetrahydropyran-2-yloxy)-prosta-4,13-dienoic acid methyl ester from (4Z,13E)-(9α,11α,15S)-9-hydroxy-11,15-bis(tetrahydropyran-2-yloxy)prosta-4,13-dienoic acid methyl ester.

TLC (cyclohexane:ethyl acetate=4:1): Rf=0.51;
IR: ν=2930, 2860, 1742, 1728, 1170, 1035, 1020 cm$^{-1}$;
NMR(CCl$_4$ solution): δ=7.82(1H,s), 5.60–5.12(4H,m), 5.12–4.75(1H,m), 4.60(2H,m), 4.58(3H,s), 4.20–3.20(6H,m), 2.27(4H,s).

(4Z,13E)-(9α,11α,15S)-9-Hydroxy-11,15-bis(tetrahydropyran-2-yloxy)-prosta-4,13-dienoic acid methyl ester, used as a starting material, was prepared as follows.

Under an atmosphere of nitrogen, 5.8 ml of a 25% (w/v) solutions of diisobutylaluminium hydride in toluene was added dropwise to a solution of 3.049 g of (E)-2-oxa-7-syn-[3S-(tetrahydropyran-2-yloxy)oct-1-enyl]-8-anti-(tetrahydropyran-2-yloxy)-cis-bicyclo[4.3.0]nonan-3-one in 80 ml of toluene at −78° C., and the mixture was stirred at that temperature for 30 minutes. The reaction mixture was quenched with aqueous methanol, filtered, and the filtrate washed with a saturated aqueous solution of sodium chloride, dried over magnesium sulphate and concentrated under reduced pressure to give 3.06 g of (E)-2-oxa-7-syn-[3S-(tetrahydropyran-2-yloxy)-oct-1-enyl]-8-anti-(tetrahydropyran-2-yloxy)-cis-bicyclo[4.3.0]nonan-3-ol having the following physical characteristic:

TLC (cyclohexane-ethyl acetate=1:1): Rf=0.50.

Under an atmosphere of nitrogen, a suspension of 1.54 g of sodium hydride (content 63%) in 20 ml of dimethyl sulphoxide was stirred at 60° to 65° C. for 1.5 hours. The obtained solution was added dropwise to a solution of 8.7 g of 3-carboxypropyltriphenylphosphonium bromide in 20 ml of dimethyl sulphoxide at room temperature, and a solution of 3.06 g of the [4.3.0]nonan-3-ol compound, prepared as described above, in 20 ml of dimethyl sulphoxide was added to it. After stirring for 45 minutes at ambient temperature, then for 45 minutes at 50° C., the reaction mixture was poured into 400 ml of ice-water containing 2 g of potassium carbonate, washed with a mixture of ethyl acetate and diethyl ether (1:1), acidified with oxalic acid to pH 2-3, and extracted with a mixture of diethyl ether and pentane (1:1). The extract was washed with water, and a saturated aqueous solution of sodium chloride, dried over magnesium sulphate and concentrated under reduced pressure. To the residue was added 4.2 ml of methyl iodide, 2.8 g of potassium carbonate and 50 ml of acetone, and the mixture was heated to the reflux temperature for one hour. The reaction mixture was then poured into a saturated aqueous solution of ammonium chloride, extracted with ethyl acetate, and the extract was washed with a saturated aqueous solution of sodium chloride, dried over magnesium sulphate and concentrated under reduced pressure. The residue was purified by column chromatography on silica gel using a mixture of cyclohexane and ethyl acetate (1:1) as eluent to give 1.799 g of (4Z,13E)-(9α,11α, 15S)-9-hydroxy-11,15-bis(tetrahydropyran-2-yloxy)prosta-4,13-dienoic acid methyl ester having the following physical characteristics:

TLC (cyclohexane: ethyl acetate=2:1): Rf=0.34;
IR: ν=3470, 2930, 2820, 1742, 1132, 1020 cm$^{-1}$;
NMR(CCl$_4$ solution): κ=5.30(4H,m), 4.60(2H,m), 3.60(3H,s), 4.20–3.16(7H,m), 2.27(4H,m).

REFERENCE EXAMPLE 4

(5Z,13E)-(9β,11α,15R)-9-Hydroxy-11,15-bis(tetrahydropyran-2-yloxy)-15-(1-butylcyclobutyl)-16,17,18,19,20-pentanorprosta-5,13-dienoic acid methyl ester Under an atmosphere of nitrogen, a mixture of 380 mg of the formyl compound (prepared as described in Reference Example 3), 6 ml of methanol and 98 mg of potassium carbonate was stirred at room temperature for one hour. To it was added 0.2 ml of acetic acid with cooling in an ice-bath, and the mixture was then concentrated under reduced pressure. The residue was dissolved in ethyl acetate, washed with a saturated aqueous solution of sodium bicarbonate, water, and a saturated aqueous solution of sodium chloride, dried over magnesium sulphate and concentrated under reduced pressure. The residue was purified by column chromatography on silica gel using a mixture of cyclohexane and ethyl acetate (4:1) as eluent to give 350 mg of the title compound having the following physical characteristics:

TLC (cyclohexane:ethyl acetate=2.1): Rf=0.15;
IR: ν=3450, 1740, 1440, 1020, 975 cm$^{-1}$;
NMR: δ=5.70–5.20(4H,m), 4.60(2H,m), 3.60(3H,s), 0.90(3H,m).

The following compounds were prepared from the corresponding formyl compounds, prepared as described in Reference Example 3, by the procedure described above.

(A) (5Z,13E)-(9β,11α, 15R)-9-Hydroxy-11,15-bis(tetrahydropyran-2-yloxy)-16,16-dimethylprosta-5,13-dienoic acid methyl ester from the product of Reference Example 3(A).

TLC (cyclohexane:ethyl acetate=2:1): Rf=0.35;
NMR: δ=5.55–5.15(4H,m), 4.90–4.50(2H,m), 4.50–3.15(10H,m), 1.05–0.59(9H,m).

(B) (5Z,13E)-(9β,11α,15S,16S)-9-Hydroxy-11,15-bis-(tetrahydropyran-2-yloxy)-16-methylprosta-5,13-dienoic acid methyl ester form the product of Reference Example 3(B).

TLC (benzene:ethyl acetate=2:1): Rf=0.30;
IR: ν=3450, 2950, 2870, 1745, 1450, 1440, 1360, 1200, 1140, 1080, 1025, 980 cm$^{-1}$;
NMR(CCl$_4$ solution): δ=5.60–5.10(4H,m) 4.70–4.40(2H,m), 3.55(3H,s), 1.10–0.70(6H,m).

(C) (5Z,13E)-(9β,11α,15R)-9-Hydroxy-11,15-bis(tetrahydropyran-2-yloxy)-16-(4-chlorophenoxy)-17,18,19,20-tetranorprosta-5,13-dienoic acid methyl ester from the product of Reference Example 3(C).

TLC (cyclohexane:ethyl acetate=1:1): Rf=0.36;
IR: ν=1740 cm$^{-1}$;
NMR: δ=7.14(2H,d), 6.74(2H,d), 5.75–5.20(4H,m), 3.58(3H,s).

(D) (5Z,13E)-(9β,11α,15S,16R)-9-Hydroxy-11,15-bis-(tetrahydropyran-2-yloxy)-16-methylprosta-5,13-dienoic acid methyl ester from the product of Reference Example 3(D).

TLC (methylene chloride:ethyl acetate=4:1): Rf=0.45;
IR: ν=3450, 2930, 1740, 1435, 1200, 1025, 970 cm$^{-1}$;
NMR: δ=6.00–4.85(4H,m) 4.85–4.30(2H,m), 3.58(3H,s), 4.30–3.00(7H,m), 1.03–0.50(6H,m).

(E) (4Z,13E)-(9β,11α,15S)-9-Hydroxy-11,15-bis(tetrahydropyran-2-yloxy)prosta-4,13-dienoic acid methyl ester from the product of Reference Example 3(E).

TLC (cyclohexane:ethyl acetate=2:1): Rf=0.22;
IR: ν=3470, 2930, 2850, 1740, 1440, 1020 cm$^{-1}$;
NMR: δ=5.70–5.15(4H,m), 4.60(2H,m), 3.60(3H,s), 4.35–3.20(7H,m), 2.30(4H,s).

REFERENCE EXAMPLE 5

(5Z,13E)-(9β,11α,15R)-9-Methanesulphonyloxy-11,15-bis(tetrahydropyran-2-yloxy)-15-(1-butylcyclobutyl)-16,17,18,19,20-pentanorprosta-5,13-dienoic acid methyl ester Under an atmosphere of nitrogen, 0.071 ml of methanesulphonyl chloride was added dropwise to a solution of 350 mg of the hydroxy compound (prepared as described in Reference Example 4) and 0.127 ml of triethylamine in 5 ml of methylene chloride at −20° C., and the mixture was stirred at that temperature for one hour. To the reaction mixture was added 5 ml of water, and the mixture extracted with ethyl acetate. The extract was washed with 1 N hydrochloric acid, water, and a saturated aqueous solution of sodium chloride, dried over magnesium sulphate and concentrated under reduced pressure. The residue was purified by column chromatography on silica gel using a mixture of cyclohexane and ethyl acetate (4:1) as eluent to give 390 mg of the title compound having the following physical characteristics:

TLC (cyclohexane:ethyl acetate=2:1): Rf=0.25;
IR: ν=1740, 1440, 1365, 1180, 1030, 975 cm$^{-1}$;
NMR: δ=5.70–5.20(4H,m), 4.90–4.45(3H,m), 3.60(3H,s), 2.95(3H,s), 0.90(3H,m).

The following compounds were prepared from the corresponding hydroxy compounds, prepared as described in Reference Example 4 or hereafter, by the procedure described above.

(A) (5Z,13E)-(9β,11α,15R)-9-Methanesulphonyloxy-11,15-bis(tetrahydropyran-2-yloxy)-16,16-dimethyl-prosta-5,13-dienoic acid methyl ester from the product of Reference Example 4(A).

TLC (cyclohexane:ethyl acetate=2:1): Rf=0.39;
IR: $\nu$=3030, 2950, 2850, 1740, 1470, 1450, 1370, 1350, 1210, 1190, 1140, 1090, 1040, 1010, 980 cm$^{-1}$;
NMR: $\delta$=5.75–5.10(4H,m), 5.35–5.00(3H,m), 5.35–3.20(9H,m), 2.98(3H,s), 1.10–0.80(9H,m).

(B) (5Z,13E)-(9β,11α,15S,16S)-9-Methanesulphonyloxy-11,15-bis(tetrahydropyran-2-yloxy)-16-methylprosta-5,13-dienoic acid methyl ester from the product of Reference Example 4(B).

TLC (benzene:ethyl acetate=2:1): Rf=0.63;
IR: $\nu$=2950, 2870, 1740, 1440, 1360, 1205, 1180, 1130, 1080, 1020, 970 cm$^{-1}$;
NMR(CCl$_4$ solution): $\delta$=5.60–5.10(4H,m), 4.90–4.40(3H,m), 3.55(3H,s), 2.90(3H,s), 1.10–0.70(6H,m).

(C) (5Z,13E)-(9β,11α,15R)-9-Methanesulphonyloxy-11,15-bis(tetrahydropyran-2-yloxy)-16-(4-chlorophenoxy)-17,18,19,20-tetranorprosta-5,13-dienoic acid methyl ester from the product of Reference Example 4(C).

TLC (cyclohexane:ethyl acetate=2:1): Rf=0.42;
IR:$\nu$=1740, 1370 cm$^{-1}$;
NMR:$\delta$=7.15(2H,d), 6.75(2H,d), 5.75–5.25(4H,m), 3.65(3H,s), 2.97(3H,s).

(D) (5Z,13E)-(9β,11α,15S,16R)-9-Methanesulphonyloxy-11,15-bis(tetrahydropyran-2-yloxy)-16-methylprosta-5,13-dienoic acid methyl ester from the product of Reference Example 4(D).

TLC (cyclohexane:ethyl acetate=2:1): Rf=0.22;
IR: $\nu$=2950, 2880, 1740, 1440, 1360, 1020, 970 cm$^{-1}$;
NMR(CCl$_4$ solution):$\delta$=5.90–4.90(4H,m), 4.90–4.32(3H,m), 3.53(3H,s), 2.86(3H,s), 1.05–0.50(6H,m).

(E) (5Z,13E)-(9β,15S)-9-Methanesulphonyloxy-15-(tetra-hydropyran-2-yloxy)prosta-5,13-dienoic acid methyl ester from (5Z,13E)-(9β,15S)-9-hydroxy-15-(tetrahydropyran-2-yloxy)prosta-5,13-dienoic acid methyl ester.

TLC (cyclohexane:ethyl acetate=2:1): Rf=0.28;
IR: $\nu$=1740, 1440, 1360, 1180, 1020, 980 cm$^{-1}$;
NMR: $\delta$=5.60–5.15(4H,m), 4.90–4.45(3H,m), 3.60(3H,s), 2.95(3H,s).

(5Z,13E)-(9β,15S)-9-Hydroxy-15-(tetrahydropyran-2-yloxy)prosta-5,13-dienoic acid methyl ester, used as a starting material, was prepared as follows:

A mixture of 2.4 g of PGE$_2$ methyl ester, 30 ml of acetic anhydride and 6 ml of pyridine was stirred at 35° C. for 40 hours. After concentration under reduced pressure, the residue was dissolved in diethyl ether, washed with water, and a saturated aqueous solution of sodium chloride, dried over magnesium sulphate and concentrated under reduced pressure to give 2.56 g of (5Z,13E)-(15S)-9-oxo-15-acetoxyprosta-5,10,13-trienoic acid methyl ester having the following physical characteristic:

TLC (cyclohexane:ethyl acetate=1:1): RF=0.55.

To a solution of 2.55 g of the trienoic acid thus obtained, in 51 ml of methanol was added dropwise a solution of 3.53 g of sodium borohydride in a mixture of 5.1 ml of water and 46 ml of methanol at −20° C. to −25° C., and the mixture was stirred at the temperature for 15 minutes. The reaction mixture was quenched with 3.53 ml of acetic acid, and then concentrated under reduced pressure. The residue was dissolved in ethyl acetate, washed with water, and a saturated aqueous solution of sodium chloride, dried over magnesium sulphate and concentrated under reduced pressure. The residue was purified by column chromatography on silica gel using a mixture of ethyl acetate and cyclohexane (1:1) as eluent to give 1.49 g of (5z,13E)-(9β,15S)-9-hydroxy-15-acetoxyprosta-5,13-dienoic acid methyl ester having the following physical characteristic:

TLC (cyclohexane-ethyl acetate=1:1): Rf=0.44 (9α-isomer, Rf=0.51).

To a solution of 1.49 g of the compound, prepared as described above, and 0.8 ml of pyridine in 18 ml of methylene chloride, was added dropwise 0.88 ml of benzoyl chloride at room temperature, the mixture was stirred at that temperature for 3 hours, and 0.3 ml of ethanol was added to it. After stirring for 10 minutes, the reaction mixture was extracted with ethyl acetate, and the extract was washed with 1N hydrochloric acid, water, a saturated aqueous solution of sodium bicarbonate, water, and a saturated aqueous solution of sodium chloride, dried over magnesium sulphate and concentrated under reduced pressure to give (5Z,13E)-(9β,15S)-9-benzoyloxy-15-acetoxyprosta-5,13-dienoic acid methyl ester having the following physical characteristic:

TLC (cyclohexane:ethyl acetate=2:1): Rf=0.57.

A mixture of the compound thus obtained, 25 ml of methanol and 552 mg of potassium carbonate was stirred at 0° C. for 3 hours, then at room temperature for 2 hours. After addition of 0.5 ml of acetic acid, the reaction mixture was concentrated under reduced pressure, the residue was dissolved in ethyl acetate, washed with water, a saturated aqueous solution of sodium bicarbonate, and a saturated aqueous solution of sodium chloride, dried over magnesium sulphate and concentrated under reduced pressure. The residue was purified by column chromatography on silica gel using a mixture of cyclohexane and ethyl acetate (7:2) as eluent to give 1.23 g of (5Z,13E)-(9β,15S)-9-benzoyloxy-15-hydroxyprosta-5,13-dienoic acid methyl ester having the following physical characteristic:

TLC (cyclohexane:ethyl acetate=2:1): Rf=0.39.

A mixture of 1.23 g of the 15-hydroxy compound, prepared as described above, 0.4 ml of 2,3-dihydropyran, a catalytic amount of p-toluenesulphonic acid and 15 ml of methylene chloride was stirred at room temperature for 15 minutes. The reaction mixture was poured into a saturated aqueous solution of sodium bicarbonate, extracted with ethyl acetate, the extract was washed with water, and a saturated aqueous solution of sodium chloride, dried over magnesium sulphate and concentrated under reduced pressure to give 1.45 g of (5Z,13E)-(9β,15S)-9-benzoyloxy-15-(tetrahydropyran-2-yloxy)prosta-5,13-dienoic acid methyl ester having the following physical characteristic:

TLC (cyclohexane:ethyl acetate=2:1): Rf=0.52.

A mixture of 1.49 g of the benzoyloxy compound, obtained above, 552 mg of potassium carbonate and 15 ml of methanol was stirred at 40° to 45° C. for 5.5 hours.

The reaction mixture was acidified to pH 3 with dilute hydrochloric acid, extracted with ethyl acetate, the extract washed with a saturated aqueous solution of sodium chloride, dried over magnesium sulphate and concentrated under reduced pressure. The residue was purified by column chromatography on silica gel using a mixture of cyclohexane and ethyl acetate (1:1) as eluent to give 1.12 g of (5Z,13E)-(9β,15S)-9-hydroxy-15-(tetrahydropyran-2-yloxy)prosta-5,13-dienoic acid methyl ester having the following physical characteristics:

TLC (cyclohexane:ethyl acetate=2:1); Rf=0.22
IR: ν=3450, 1740, 1440, 1020, 980 cm$^{-1}$;
NMR: δ=5.70–5.10(4H,m), 4.60(1H,m), 3.60(3H,s), 0.90(3H,m).

(F) (4Z,13E)-(9β,11α,15S)-9-Methanesulphonyloxy-11,15-bis(tetrahydropyran-2-yloxy)prosta-4,13-dienoic acid methyl ester from the product of Reference Example 4(E).

TLC (cyclohexane:ethyl acetate=2:1): Rf=0.38;
IR: ν=1740, 1360, 1173, 1033, 1020, 970 cm$^{-1}$;
NMR(CCl$_4$ solution): δ=5.65–5.00(4H,m), 4.80–4.42(3H,m), 3.55(3H,s), 4.25–3.13(6H,m), 2.90(3H,s), 2.26(4H,s).

REFERENCE EXAMPLE 6

(5Z,13E)-(9α,11α,15R)-9-Acetylthio-11,15-bis(tetrahydropyran-2-yloxy)-15-(1-butylcyclobutyl)-16,17,18,19,20-pentanorprosta-5,13-dienoic acid methyl ester Under an atmosphere of nitrogen, 0.335 ml of thioacetic S-acid was added dropwise to a suspension of 137 mg of sodium hydride (content 63%) in 3.5 ml of dimethyl sulphoxide with stirring at room temperature, and stirring was continued for 40 minutes. To the solution was added dropwise a solution of 390 mg of the methanesulphonyloxy compound (prepared as described in Reference Example 5) in 2 ml of dimethyl sulphoxide at room temperature, and the mixture was stirred at 40° to 45° C. for 2 hours. The reaction mixture was poured into 30 ml of ice-water, extracted with diethyl ether, the extract was washed with water, and a saturated aqueous solution of sodium chloride, dried over magnesium sulphate and concentrated under reduced pressure. The residue was purified by column chromatography on silica gel using a mixture of cyclohexane and ethyl acetate (6:1) as eluent to give 290 mg of the title compound having the following physical characteristics:

TLC (cyclohexane:ethyl acetate=2:1): Rf=0.50;
IR: ν=1740, 1695, 1440, 1130, 1025, 975 cm$^{-1}$;
NMR: δ=5.70–5.20(4H,m), 4.60(2H,m), 3.60(3H,s), 2.27(3H,s), 0.90(3H,m).

The following compounds were prepared from the corresponding methanesulphonyloxy compounds, prepared as described in Reference Example 5, by the same procedure as described above.

(A) (5Z,13E)-(9α,11α,15R)-9-Acetylthio-11,15-bis(-tetrahydropyran-2-yloxy)-16,16-dimethylprosta-5,13-dienoic acid methyl ester from the product of Reference Example 5(A).

TLC (cyclohexane:ethyl acetate=2:1): Rf=0.68;
NMR: δ=5.65–5.10(4H,m), 4.70–4.34(2H,m), 4.25–3.00(10H,m), 2.28(3H,s), 1.05–0.71(9H,m).

(B) (5Z,13E)-(9α,11α,15S,16S)-9-Acetylthio-11,15-bis-(tetrahydropyran-2-yloxy)-16-methylprosta-5,13-dienoic acid methyl ester from the product of Reference Example 5(B).

TLC (benzene:ethyl acetate=4:1): Rf=0.64;
IR: ν=2950, 2870, 1745, 1695, 1440, 1360, 1205, 1130, 1080, 1030, 975 cm$^{-1}$;
NMR(CCl$_4$ solution): δ=5.60–5.10(4H,m), 4.70–4.40(2H,m), 3.55(3H,s), 2.25(3H,s), 1.10–0.70(6H,m).

(C) (5Z,13E)-(9α,11α,15R)-9-Acetylthio-11,15-bis-(tetrahydropyran-2-yloxy)-16-(4-chlorophenoxy)-17,18,19,20-tetranorprosta-5,13-dienoic acid methyl ester from the product of Reference Example 5(C).

TLC (cyclohexane:ethyl acetate=2:1): Rf=0.72;
IR: ν=1740, 1696 cm$^{-1}$;
NMR: δ=7.10(2H,d), 6.72(2H,d), 5.72–5.20(4H,m), 3.60(3H,s), 2.30(3H,s).

(D) (5Z,13E)-(9α,11α,15S,16R)-9-Acetylthio-11,15-bis(tetrahydropyran-2-yloxy)-16-methylprosta-5,13-dienoic acid methyl ester from the product of Reference Example 5(D).

TLC (cyclohexane:ethyl acetate=2:1): Rf=0.51;
IR: ν=2950, 2875, 1740, 1690, 1435, 1030, 970 cm$^{-1}$;
NMR(CCl$_4$ solution):δ=6.00–4.82(4H,m), 4.82–4.27(2H,m), 4.27–3.00(7H,m), 3.56(3H,s), 2.26(3H,s), 1.10–0.53(6H,m).

(E) (5Z,13E)-(9α,15S)-9-Acetylthio-15-(tetrahydropyran-2-yloxy)prosta-5,13-dienoic acid methyl ester from the product of Reference Example 5(E).

TLC (cyclohexane-ethyl acetate=2:1): Rf=0.58;
IR: ν=1740, 1690,1440, 1360, 1200, 1130, 1115, 1020, 980 cm$^{-1}$;
NMR: δ=5.60–5.15(4H,m), 4.60(1H,m), 3.60(3H,s), 2.25(3H,s), 0.90(3H,m).

(F) (4Z,13E)-(9α,11α,15S)-9-Acetylthio-11,15-bis(-tetrahydropyran-2-yloxy)prosta-4,13-dienoic acid methyl ester from the product of Reference Example 5(F).

TLC (cyclohexane:ethyl acetate=2:1): Rf=0.54;
IR: ν=2930, 2550, 1740, 1690, 1125, 1020 cm$^{-1}$;
NMR(CCl$_4$ solution):δ=5.60–5.04(4H,m), 4.57(2H,m), 3.57(3H,s), 4.20–3.10(7H,m), 2.27(3H,s).

REFERENCE EXAMPLE 7

9α,9α'-Bi[(5Z,13E)-(11α,15R)-11,15-bis(tetrahydropyran-2-yloxy)-15-(1-butylcyclobutyl)-16,17,18,19,20-pentanorprosta-5,13-dienoic acid methyl ester] disulphide Under an atmosphere of nitrogen, a mixture of 290 mg of the acetylthio compound (prepared as described in Reference Example 6), 4 ml of methanol and 70 mg of potassium carbonate was stirred at room temperature for 1.5 hours, then at 35° C. for 1.5 hours. The reaction mixture was poured into 20 ml of ice-water, extracted with diethyl ether, the extract was washed with water, and a saturated aqueous solution of sodium chloride, dried over magnesium sulphate and concentrated under reduced pressure. The residue was purified by column chromatography on silica gel using a mixture of cyclohexane and ethyl acetate (6:1) as eluent to give 250 mg of the title compound having the following physical characteristics:

TLC (cyclohexane-ethyl acetate=4:1): Rf=0.25;
IR: ν=1740, 1440, 1030, 975 cm$^{-1}$;
NMR: δ=5.70–5.20(8H,m), 4.60(4H,m), 3.60(6H,s), 0.90(6H,m).

The following compound was prepared from the corresponding acetylthio compound, prepared as described in Reference Example 6(B), by the same procedure as described above.

(A) 9α,9α'-Bi[(5Z,13E)-(11α,15S,16S)-11,15-bis-(tetrahydropyran-2-yloxy)-16-methylprosta-5,13-dienoic acid methyl ester] disulphide.

TLC (benzene:ethyl acetate=4:1): Rf=0.48;

NMR(CCl$_4$ solution):δ=5.60–5.10(8H,m), 4.70–4.40(4H,m), 3.55(6H,s), 1.10–0.70(12H,m);
MS:m/e=480, 462, 378, 360.

REFERENCE EXAMPLE 8

9α,9α'-Bi[(5Z,13E)-(11α,15R)-11,15-dihydroxy-15-(1-butylcyclobutyl)-16,17,18,19,20-pentanorprosta-5,13-dienoic acid methyl ester] disulphide A mixture of 250 mg of the tetrahydropyran-2-yloxy compound (prepared as described in Reference Example 7), 8 ml of tetrahydrofuran and 4 ml of 1N hydrochloric acid was stirred at room temperature, then at 40° to 45° C. for 2 hours. The reaction mixture was extracted with ethyl acetate, the extract was washed with water, a saturated aqueous solution of sodium chloride, dried over magnesium sulphate and concentrated under reduced pressure. The residue was purified by column chromatography on silica gel using ethyl acetate as eluent to give 70 mg of the title compound having the following physical characteristics:

TLC (ethyl acetate): Rf=0.48;
NMR: δ=5.35(8H,m), 3.90(4H,m), 3.60(6H,s), 3.35(2H,m), 0.90(6H,m);
MS:m/e=406, 404, 388, 386, 375.

REFERENCE EXAMPLE 9

(5Z,13E)-(9α,11α,15R)-9-Mercapto-11,15-dihydroxy-15-(1-butylcyclobutyl)-16,17,18,19,20-pentanorprosta-5,13-dienoic acid methyl ester A mixture of 57 mg of the disulphide compound (prepared as described in Reference Example 8), 1.3 ml of 10% v/v aqueous methanol, 35 μl of tributylphosphine and 3 drops of acetone was stirred at room temperature for 2.5 hours. The reaction mixture was diluted with ethyl acetate, washed with a saturated aqueous solution of sodium chloride, dried over magnesium sulphate and concentrated under reduced pressure. The residue was purified by column chromatography on silica gel using a mixture of cyclohexane and ethyl acetate (1:2) as eluent to give 44 mg of the title compound having the following physical characteristics:

TLC (cyclohexane:ethyl acetate=1:2): Rf=0.44;
IR: ν=3400, 1740, 1440, 1250, 980 cm$^{-1}$;
NMR: δ=5.45(2H,m), 5.25(2H,m), 4.05–3.20(6H,m);
MS:m/e=406, 393, 388, 295.

The following compound was prepared from the compound, prepared as described in Reference Example 7(A), by the procedure described above.

(A) (5Z,13E)-(9α,11α,15S,16S)-9-Mercapto-11,15-bis-(tetrahydropyran-2-yloxy)-16-methylprosta-5,13-dienoic acid methyl ester.

TLC (benzene:ethyl acetate=4:1): Rf=0.68;
IR: ν=2950, 2870,1745, 1450, 1440, 1360, 1270, 1205, 1135, 1080, 1025, 975 cm$^{-1}$;
NMR(CCl$_4$ solution):δ=5.60–5.10(4H,m), 470–4.40(2H,m), 3.55(3H,s), 1.10–0.70(6H,m);
MS:m/e=535, 464, 380, 362.

REFERENCE EXAMPLE 10

(5Z,13E)-(9α,11α,15R)-9-Acetylthio-11,15-dihydroxy-16,16-dimethylprosta-5,13-dienoic acid methyl ester A mixture of 1.507 g of the tetrahydropyran-2-yloxy compound, (prepared as described in Reference Example 6(A)), 30 ml of 65% v/v acetic acid and 6 ml of tetrahydrofuran was stirred at 40° to 45° C. for 2 hours. The reaction mixture was poured into 150 ml of a saturated aqueous solution of sodium bicarbonate with cooling in an ice-bath, extracted with ethyl acetate, the extract was washed with a saturated aqueous solution of sodium bicarbonate, and a saturated solution of sodium chloride, dried over magnesium sulphate and concentrated under reduced pressure. The residue was purified by column chromatography on silica gel using a mixture of cyclohexane and ethyl acetate (1:2) as eluent to give 785 mg of the title compound having the following physical characteristics:

TLC (cyclohexane:ethyl acetate=1:2): Rf=0.52;
NMR:δ=5.70–5.00(4H,m), 4.20–3.00(8H,m), 2.28(3H,s), 1.01–0.60(9H,m).

The following compounds were prepared from the corresponding tetrahydropyran-2-yloxy compounds by the same procedure as described above.

(A) (5Z,13E)-(9α,11α,15R)-9-Acetylthio-11,15-dihydroxy-16-(4-chlorophenoxy)-17,18,19,20-tetranorprosta-5,13- dienoic acid methyl ester from the product of Reference Example 6(C).

TLC (ethyl acetate:cyclohexane=2:1): Rf=0.53;
IR: ν=1740, 1695 cm$^{-1}$;
NMR: δ=7.13(2H,d) 6.75(2H,d), 5.67(2H,m), 5.40(2H,m), 3.62(3H,s), 2.32(3H,s).

(B) (5Z,13E)-(9α,11α,15S,16R)-9-Acetylthio-11,15-dihydroxy-16-methylprosta-5,13-dienoic acid methyl ester from the product of Reference Example 6(D).

TLC (ethyl acetate:cyclohexane=2:1): Rf=0.31;
IR: ν=3400, 2950, 1740, 1690, 1430, 1120, 970 cm$^{-1}$;
NMR: δ=6.00–4.90(4H,m), 4.50–3.50(3H,m), 3.68(3H,s), 2.35(3H,s), 1.13–0.66(6H,m).

(C) (5Z,13E)-(9α,15S)-9-Acetylthio-15-hydroxyprosta-5,13-dienoic acid methyl ester from the product of Reference Example 6(E).

TLC (cyclohexane:ethyl acetate=2:1): Rf=0.40;
IR: ν=3450, 1740, 1690, 1430, 970 cm$^{-1}$;
NMR: δ5.60–5.10(4H,m), 4.05(2H,m), 3.60(3H,s), 2.25(3H,s), 0.90(3H,m).

(D) (4Z,13E)-(9α,11α,15S)-9-Acetylthio-11,15-dihydroxyprosta-4,13-dienoic acid methyl ester from the product of Reference Example 6(F).

TLC (ethyl acetate:cyclohexane=2:1): Rf=0.37;
IR: ν=3360, 2930, 2860, 1740, 1690, 1437, 1360, 1125 cm$^{-1}$
NMR:δ=5.56–5.07(4H,m), 3.65(3H,s), 4.20–3.65(3H,m), 2.30(7H,s).

REFERENCE EXAMPLE 11

The following compounds were prepared from the corresponding acetylthio compounds by the procedure described in Reference Example 7. The reaction was carried out at room temperature for 20 to 60 minutes.

(A) (5Z,13E)-(9α,11α, 15R)-9-Mercapto-11,15-dihydroxy-16,16-dimethylprosta-5,13-dienoic acid methyl ester from the product of Reference Example 10.

TLC (cyclohexane:ethyl acetate=1:2): Rf=0.52;
IR: ν=3400, 3030, 2950, 2850, 1740, 1440, 1370, 1320, 1240, 1200, 1180, 1155, 1080, 1020, 980 cm$^{-1}$;
NMR: δ=5.60–5.05(4H,m), 4.10–3.10(6H,m), 1.10–0.62(9H,m).

(B) (5Z,13E)-(9α,11α,15R)-9-Mercapto-11,15-dihydroxy-16-(4-chlorophenoxy)-17,18,19,20-tetranorprosta-5,13-dienoic acid methyl ester from the product of Reference Example 10(A).

TLC (cyclohexane:ethyl acetate=1:2): Rf=0.53;
IR: ν=1740 cm$^{-1}$;
NMR: δ=7.10(2H,d), 6.73(2H,d), 5.65(2H,m), 5.42(2H,m), 3.63(3H,s).

(C) (5Z,13E)-(9α,11α,15S,16R)-9-Mercapto-11,15-dihydroxy-16-methylprosta-5,13-dienoic acid methyl ester from the product of Reference Example 10(B).

TLC (cyclohexane:ethyl acetate=1:2): Rf=0.30;
IR: ν=3400, 2950, 1740, 1430, 970 cm⁻¹;
NMR: δ=5.85–4.90(4H,m), 3.60(3H,s), 1.06–0.50(6H,m).

(D) (5Z,13E)-(9α,15S)-9-Mercapto-15-hydroxyprosta-5,13-dienoic acid methyl ester from the product of Reference Example 10(C).

TLC (cyclohexane:ethyl acetate=2:1): Rf=0.45;
IR: ν=3450, 1740, 1440, 970 cm⁻¹;
NMR: δ=5.60–5.15(4H,m), 4.00(1H,m), 3.60(3H,s), 3.45(1H,m), 0.90(3H,m).

(E) (4Z,13E)-(9α,11α,15S)-9-Mercapto-11,15-dihydroxyprosta-4,13-dienoic acid methyl ester from the product of Reference Example 10(D).

TLC (ethyl acetate:cyclohexane=2:1): RF=0.37;
IR: ν=3370, 2930, 2860, 1740, 1438 cm⁻¹;
NMR: δ=5.62–5.10(4H,m), 3.61(3H,s), 2.30(4H, m).

(F) (5Z,13E)-(9α,11α,15S)-9-Mercapto-11,15-bis(tetrahydropyran-2-yloxy)prosta-5,13-dienoic acid methyl ester from (5Z,13E)-(9α,11α,15S)-9-acetylthio-11,15-bis(tetrahydropyran-2-yloxy)prosta-5,13-dienoic acid methyl ester [prepared as described in 'Tetrahedron Letters', 559(1978)].

TLC (hexane:ethyl acetate=7:3): Rf=0.43;
IR: ν=1741, 1460, 1450, 1437, 1353, 1200, 1130, 1075, 1033, 1020, 972 cm⁻¹.

EXAMPLE 1

(13E)-(6RS,9α, 11α, 15R)-6,9-Epithio-11,15-dihydroxy-15-(1-butylcyclobutyl)-16,17,18,19,20-pentanorprost-13-enoic acid methyl ester [or 15-(1-butylcyclobutyl)-16,17,18,19,20-pentanor-thio PGI₁ methyl ester]

A mixture of 43 mg of the mercapto compound (prepared as described in Reference Example 9), 1 ml of methanol and 0.5 ml of 1N hydrochloric acid was stirred at room temperature for one hour. The reaction mixture was diluted with ethyl acetate, washed with water, a saturated aqueous solution of sodium bicarbonate, water, and a saturated aqueous solution of sodium chloride, dried over magnesium sulphate and concentrated under reduced pressure. The residue was purified by column chromatography on silica gel using a mixture of cyclohexane and ethyl acetate (1:2) as eluent to give 25 mg of the title compound having the following physical characteristics:

TLC (cyclohexane:ethyl acetate=2:1): Rf=0.44;
IR: ν=3400, 1740, 1440, 1100, 980 cm⁻¹;
NMR: δ=5.57(2H,m), 3.97(1H,m), 3.85–3.20(6H,m), 0.91(3H,m);
MS: m/e=406, 398, 388, 362, 295, 263, 252.

The following compounds were prepared from the corresponding mercapto compounds by the same procedure as described above.

(A) (13E)-(6RS,9α,11α,15R)-6,9-Epithio-11,15-dihydroxy-16,16-dimethylprost-13-enoic acid methyl ester [or 16,16-dimethyl-thio-PGI₁ methyl ester] from the product of Reference Example 11(A).

TLC (cyclohexane:ethyl acetate=1:2): Rf=0.52;
IR: ν=3400, 2950, 2850, 1740, 1460, 1440, 1370, 1260, 1210, 1180, 1020, 980 cm⁻¹;
NMR: δ=5.81–5.29(2H,m), 4.20–3.30(7H,m). 1.05–0.62(9H,m);
MS: m/e=394, 381, 350.

(B) (13E)-(6RS,9α,11α,15S,16S)-6,9-Epithio-11,15-dihydroxy-16-methylprost-13-enoic acid methyl ester [or 16S-methyl-thio-PGI₁ methyl ester] from the product of Reference Example 9(A).

TLC (benzene:ethyl acetate=1:2): Rf=0.41;
IRν=3450, 2930, 1740, 1715, 1440, 1380, 1170, 1080, 1010, 975 cm⁻¹;
NMR: δ=5.60–5.40(2H,m), 4.00–3.20(4H,m), 3.68(3H,s), 1.05–0.75(6H,m);
MS: m/e=398, 380, 367, 362.

(C) (13E)-(6RS,9α,11α,15R)-6,9-Epithio-11,15-dihydroxy-16-(4-chlorophenoxy)-17,18,19,20-tetranorprost-13-enoic acid methyl ester [or 16-(4-chlorophenoxy)-17,18,19,20-tetranor-thio-PGI₁ methyl ester] from the product of Reference Example 11(B).

TLC (cyclohexane:ethyl acetate=1:2): Rf=0.53;
IR:ν=1740 cm⁻¹;
NMR:δ=7.12(2H,d), 6.74(2H,d), 5.63(2H,m), 3.58(3H,s).

(D) (13E)-(6RS,9α,11α,15S,16R)-6,9-Epithio-11,15-dihydroxy-16-methylprost-13-enoic acid methyl ester [or 16R-methyl-thio-PGI₁ methyl ester] from the product of Reference Example 11(C).

TLC (ethyl acetate:cyclohexane=2:1): Rf=0.33;
IR: ν=3450, 2940, 2875, 1740, 1710, 1170, 1010, 970 cm⁻¹;
NMR: δ=5.89–5.14(2H,m), 4.47–3.15(8H,m), 1.50–0.60(6H,m);
MS:m/e=380, 295, 277, 263, 252, 113, 85, 43.

(E) (13E)-(6RS,9α,15S)-6,9-Epithio-15-hydroxyprost-13-enoic acid methyl ester [or 11-deoxy-thio-PGI₁ methyl ester] from the product of Reference Example 11(D).

TLC (cyclohexane:ethyl acetate=2:1): Rf=0.43;
IR: ν=3450, 1740, 1440, 970 cm⁻¹;
NMR: δ=5.51(2H,m), 4.04(1H,m), 3.78(1H,m) 3.66(3H,s), 3.40(1H,m), 0.89(3H,m);
MS: m/e=368, 350, 337, 317, 297, 290, 279, 265, 224, 211, 189.

(F) (13E)-(5RS,9α,11α,15S)-5,9-Epithio-11,15-dihydroxyprost-13-enoic acid methyl ester from the product of Reference example 11(E).

TLC (ethyl acetate:cyclohexane=2:1): Rf=0.41;
IR: ν=3370, 2920, 2850, 1740, 1433 cm⁻¹;
NMR: δ=5.51(2H,m), 3.66(3H,s), 4.15–3.15(4H,m), 2.32(3H,t).

(G) (13E)-(6RS,9α,11α,15S)-6,9-Epithio-11,15-dihydroxyprost-13-enoic acid methyl ester [or thio-PGI₁ methyl ester] from the product of Reference Example 11(F).

TLC (ethyl acetate): Rf=0.46;
IR: ν=3380, 1740, 1440, 1260, 1200, 1176, 1020, 975 cm⁻¹;
NMR: δ=5.78–5.30(2H,m), 4.26–3.20(4H,m), 3.66(3H,s).

EXAMPLE 2

(13E)-(6RS,9α,11α,15S)-6,9-Epithio-11,15-dihydroxyprost-13-enoic acid [or thio-PGI₁]

A mixture of 45 mg of the thio-PGI₁ methyl ester [prepared as described in Example 1(G)], 1 ml of methanol and 0.7 ml of 1N aqueous potassium hydroxide was stirred at room temperature for 30 minutes. The reaction mixture was acidified with 1N hydrochloric acid to pH2, diluted with ethyl acetate, washed with water, a saturated, aqueous solution of sodium chloride, dried over magnesium sulphate and concentrated under reduced pressure. The residue was purified by column chromatography on silica gel using a mixture of ethyl acetate and cyclohexane (3:1) as eluent to give 30 mg of the title compound as white amorphous crystals having the following physical characteristics: melting point: 72°–73° C.;

IR(KBr tablet):ν=3350, 1950, 1850, 1700, 1450, 1390, 1350, 1330, 1260, 1210, 1180, 1080, 1000, 980 cm$^{-1}$;

MS: m/e=352, 334, 308.

EXAMPLE 3

(13E)-(6R,9α,11α,15S)-6,9-Epithio-11,15-dihydroxy-prost-13-enoic acid methyl ester [or 6R-thio-PGI$_1$ methyl ester] and (13E)-(6S,9α,11α,15S)-6,9-epithio-11,15-dihydroxy-prost-13-enoic acid methyl ester [or 6S-thio-PGI$_1$ methyl ester]

25 mg of (13E)-(6RS, 9α,11α,15S)-6,9-epithio-11,15-dihydroxyprost-13-enoic acid methyl ester [prepared as described in Example 1(G)] were separated by thin layer chromatography on silica gel developing three times with a mixture of ethyl acetate and hexane (3:1) as developing solvent to give 7 mg of the 6R-compound and 6 mg of the 6S-compound. The compounds showed the following physical characteristics.

(a) 6R-Thio-PGI$_1$ methyl ester;

TLC (ethyl acetate:hexane=3:1, three times development); Rf=0.48;

NMR: δ=5.60–5.40(2H,m), 4.15–3.20(4H,m), 3.66(3H,s), 1.00–1.70(3H,m);

MS: m/e=366, 353, 348, 332, 322, 315, 306, 295, 252.

(b) 6S-Thio-PGI$_1$ methyl ester;

TLC (ethyl acetate:hexane=3:1, three times development); RF=0.43;

NMR: δ=5.80–5.30(2H,m), 4.04(1H,m), 3.85–3.20(3H,m), 3.67(3H,s), 1.00–0.70(3H,m);

MS: m/e=366, 353, 348, 332, 322, 315, 306, 295, 252.

REFERENCE EXAMPLE 12

(13E)-(6RS,9α,11α,15S)-6,9-Epithio-11,15-bis(tetrahydropyran-2-yloxy)-prost-13-enoic acid methyl ester The title compound (552 mg) was prepared from (13E)-(6RS,9α,11α,15S)-6,9-epithio-11,15-dihydroxy-prost-13-enoic acid methyl ester [prepared as described in Example 1(G)] (384 mg) by the tetrahydropyran-2-ylation described in Reference Example 1.

TLC (ethyl acetate:hexane=3:7): Rf=0.40.

REFERENCE EXAMPLE 13

(13E)-(2RS,6RS,9α,11α,15S)-2-Phenylseleno-6,9-epithio-11,15-bis(tetrahydropyran-2-yloxy)prost-13-enoic acid methyl ester Under an atmosphere of argon, 1 ml of a 1.5M solution of butyllithium in hexane was added to a mixture of 0.28 ml of diisopropylamine and 2 ml of tetrahydrofuran at −78° C., and the mixture was stirred at that temperature for 10 minutes. To it was added dropwise a solution of 500 mg of the tetrahydropyran-2-yloxy compound (prepared as described in Reference Example 12) in 5 ml of tetrahydrofuran at −78° C., the mixture was stirred at the same temperature for 30 minutes, a solution of 468 mg of diphenyl diselenide in 3 ml of tetrahydrofuran was added to it, and the mixture was stirred at −78° C. for 20 minutes. The reaction mixture was poured into a saturated aqueous solution of ammonium chloride, extracted with ethyl acetate, the extract was washed with 0.5N hydrochloric acid, a saturated aqueous solution of sodium bicarbonate, and a saturated aqueous solution of sodium chloride, dried over sodium sulphate and concentrated under reduced pressure. The residue was purified by column chromatography on silica gel using a mixture of cyclohexane and ethyl acetate (9:1) as eluent to give 624 mg of the title compound having the following physical characteristics:

TLC (cyclohexane:ethyl acetate=4:1) Rf=0.40 and 0.37;

IR: ν=1735, 1580, 1452, 1435, 1378, 1358, 1345, 1326, 1268, 1245, 1200, 1185, 1135, 1078, 1035, 1021, 975 cm$^{-1}$;

NMR(CC$_4$ solution):δ=7.60–7.00(5H,m), 5.60–5.10(2H,m), 4.56(2H,m), 3.54(3H,s), 1.10–0.70(3H,m);

MS: m/e=606, 551, 522, 504, 478.

REFERENCE EXAMPLE 14

(2E,13E)-(6RS,9α,11α,15S)-6,9-Epithio-11,15-bis-(tetrahydropyran-2-yloxy)prosta-2,13-dienoic axid methyl ester A mixture of 600 mg of the phenylseleno compound [prepared as described in Reference Example 13], 14 ml of tetrahydrofuran, 107 mg of sodium bicarbonate and 1 ml of 30% v/v hydrogen peroxide was stirred at 15° to 60° C. for 5.5 hours. The reaction mixture was diluted with ethyl acetate, dried over sodium sulphate and concentrated under reduced pressure. The residue was purified by column chromatography on silica gel using a mixture of methylene chloride and ethyl acetate (19:1) as eluent to give 42 mg of the title compound, and 415 mg of a mixture of (2E,13E)-(6RS,9α,11α,15S)-6,9-sulphinyl-11,15-bis(tetrahydropyran-2-yloxy)prosta-2,13-dienoic acid methyl ester and (13E)-(2RS,6RS,9α,11α,15S)-2-phenylseleno-6,9-sulphinyl-11,15-bis-(tetrahydropyran-2-yloxy)prost-13-enoic acid methyl ester. The compounds showed the following physical characteristics.

(a) The title compound:

TLC (methylene chloride:ethyl acetate=9:1): Rf=0.52;

NMR: δ=7.30–6.60(1H,m), 5.77(1H,d), 5.70–5.20(2H,m), 4.63(2H,m), 3.65(3H,s).

(b) (2E,13E)-(6RS,9α,11α,15S)-6,9-Sulphinyl-11,15-bis(tetrahydropyran-2-yloxy)prosta-2,13-dienoic acid methyl ester:

TLC (ethyl acetate): Rf=0.20 and 0.28.

(c) (13E)-(2RS,6RS,9α,11α,15S)-2-Phenylseleno-6,9-sulphinyl-11,15-bis(tetrahydropyran-2-yloxy)prost-13-enoic acid methyl ester:

TLC(ethyl acetate): Rf=0.28.

EXAMPLE 4

(2E,13E)-(6RS,9α,11α,15S)-6,9-Epithio-11,15-dihydroxyprosta-2,13-dienoic acid methyl ester The title compound (17 mg) was prepared from (2E,13E)-(6RS,9α,11α,15S)-6,9-epithio-11,15-bis(tetrahydropyran-2-yloxy)prosta-2,13-dienoic acid methyl ester (prepared as described in Reference Example 14; 40 mg) by the same procedure as described in Reference Example 10.

TLC (ethyl acetate): Rf=0.44;

IR(KBr tablet):ν=3460, 1728, 1705, 1655, 1438, 1325, 1293, 1200, 1180, 1080, 1025, 973 cm$^{-1}$;

NMR: δ=7.15–6.13(1H,m), 5.84(1H,d), 5.70–5.25(2H,m), 4.20–3.20(4H,m), 3.72(3H,s), 1.04–0.82(3H,m);
MS: m/e=382, 364, 351, 346, 330, 320.

EXAMPLE 5

(2E,13E)-(6RS,9α,11α,15S)-6,9-Sulphinyl-11,15-dihydroxyprosta-2,13-dienoic acid methyl ester and (2E,13E)-(6RS,9α,11α,15S)-6,9-sulphonyl-11,15-dihydroxyprosta-2,13-dienoic acid methyl ester A mixture of 371 mg of the mixture (prepared as described in Reference Example 14), 5 ml of ethyl acetate, 100 mg of sodium bicarbonate and 0.1 ml of 35% v/v hydrogen peroxide was stirred at room temperature for 30 minutes, then to it was added 20 mg of sodium hydrosulphite, and the mixture was stirred at room temperature for 10 minutes. The reaction mixture was diluted with ethyl acetate, dried over sodium sulphate and concentrated under reduced pressure to give 360 mg of a mixture of (2E,13E)-(6RS,9α,11α,15S)-6,9-sulphinyl-11,15-bis(tetrahydropyran-2-yloxy)prosta-2,13-dienoic acid methyl ester and (2E,13E)-(6RS,9α,11α,15S)-6,9-sulphonyl-11,15-bis(tetrahydropyran-2-yloxy)prosta-2,13-dienoic acid methyl ester. The sulphonyl compound showed the following physical characteristic:
TLC (ethyl acetate): Rf=0.66.

A mixture of 360 mg of the mixture, prepared above, 1 ml of tetrahydrofuran and 4 ml of 65% v/v acetic acid was stirred at 45° to 60° C. for 4 hours. The reaction mixture was diluted with ethyl acetate, washed with water, a saturated aqueous solution of sodium bicarbonate, a saturated aqueous solution of sodium chloride, dried over sodium sulphate and concentrated under reduced pressure. The residue was purified by column chromatography on silica gel using ethyl acetate as eluent to give 108 mg of the sulphinyl title compound, and 63 mg of the sulphonyl title compound. The compounds showed the following physical characteristics.
(a) The sulphinyl compound:
TLC (methanol:ethyl acetate=1:19) Rf=0.09;
NMR: δ=6.99(1H,m), 5.91(1H,d), 5.74–5.35(2H,m), 4.43–3.55(4H,m), 3.67(3H,s), 1.00–0.70(3H,m);
MS: m/e=398, 380, 367, 362, 331, 323, 313, 188, 187.
(b) The sulphonyl compound:
TLC (methanol:ethyl acetate=1:19): Rf=0.39;
NMR: δ=6.94(1H,m), 5.89(1H,d), 5.70–5.40(2H,m), 4.20–3.00(4H,m), 3.68(3H,s), 1.00–0.70(3H,m);
MS: m/e=396, 378, 364, 346, 343, 330, 312, 298, 293, 213.

EXAMPLE 6

(13E)-(9α,11α,15S)-6,9-Sulphinyl-11,15-dihydroxyprost-13-enoic acid methyl ester and (13E)-(9α,11α,15S)-6,9-sulphonyl-11,15-dihydroxyprost-13-enoic acid methyl ester Under an atmosphere of argon, a solution of 270 mg of m-chloroperbenzoic acid (content 70%) in 6 ml of methylene chloride was added dropwise to a mixture of 300 mg of (13E)-(9α,11α,15S)-6,9-epithio-11,15-dihydroxyprost-13-enoic acid methyl ester [prepared as described in Example 1(G)], 131 mg of sodium bicarbonate and 3 ml of methylene chloride at −78° C., and the mixture was stirred at that temperature for 1.5 hours. To it was added 98 mg of sodium hydrosulphite, and the mixture was stirred at room temperature for 10 minutes. The reaction mixture was filtered through a pad of sodium sulphate, and the filtrate was concentrated under reduced pressure. The residue was purified by column chromatography on silica gel using a 2% v/v solution of methanol in ethyl acetate as eluent to give 90 mg of the sulphinyl compound, and 165 mg of the sulphonyl compound. The sulphonyl compound showed the following physical characteristics:
TLC (methanol:ethyl acetate=1:19): Rf=0.49;
IR: ν=3430, 1735, 1439, 1370, 1220, 1175, 1075, 973 cm$^{-1}$;
NMR: δ=5.80–5.25(2H,m), 4.20–3.20(4H,m), 3.68(3H,s), 1.04–0.74(3H,m);
MS: m/e=398, 385, 380, 367, 349.

The sulphinyl compound, thus obtained, (25 mg) was separated into a less polar isomer (13 mg) and a more polar isomer (11 mg) by thin layer chromatography on silica gel developing three times with a 5% v/v solution of methanol in ethyl acetate as developing solvent.

The isomers showed the following physical characteristics:
(a) The less polar isomer:
TLC (methanol:ethyl acetate=1:19): Rf=0.13;
NMR: δ=5.65–5.36(2H,m), 4.18–3.81(2H,m), 3.80–3.10(2H,m), 3.67(3H,s).
(b) The more polar isomer:
TLC (methanol:ethyl acetate=1:19): Rf=0.08;
NMR: δ=5.71–5.28(2H,m), 4.20–3.20(4H,m), 3.67(3H,s).

EXAMPLE 7

(13E)-(9α,11α,15S,16R)-6,9-Sulphonyl-11,15-dihydroxy-16-methylprost-13-enoic acid methyl ester Under an atmosphere of nitrogen, a solution of 53.8 mg of m-chloroperbenzoic acid (content 70%) in 1 ml of methylene chloride was added dropwise to a mixture of 56 mg of (13E)-(9α,11α,15S,16R)-6,9-epithio-11,15-dihydroxy-16-methylprost-13-enoic acid methyl ester [prepared as described in Example 1(D)], 23.6 mg of sodium bicarbonate and 6 ml of methylene chloride at −70° C., and the mixture was stirred at room temperature for 2 hours. The reaction mixture was quenched with sodium hydrosulphite, diluted with ethyl acetate, washed with water, and a saturated aqueous solution of sodium chloride, dried over magnesium sulphate and concentrated under reduced pressure. The residue was purified by column chromatography on silica gel using a mixture of cyclohexane and ethyl acetate (1:2) as eluent to give 44 mg of the title compound having the following physical characteristics:
TLC (ethyl acetate): Rf=0.35;
IR: ν=3450, 2975, 2945, 2875, 1735, 1310, 1270, 1120, 975 cm$^{-1}$;
NMR: δ=6.00–5.05(2H,m), 4.45–2.75(6H,m), 3.67(3H,s), 1.05–0.60(6H,m);
MS: m/e=412, 394, 381, 346, 328, 295.

EXAMPLE 8

(13E)-(6RS,9α,11α,15S)-N-Methanesulphonyl-6,9-epithio-11,15-dihydroxyprost-13-en-1-amide To a mixture of 100 mg of (13E)-(6RS,9α,11α,15S)-6,9-epithio-11,15-dihydroxyprost-13-enoic acid (prepared as described in Example 2), 1.5 ml of N,N-dimethylformamide and 37 μl of triethylamine was added 35 μl of isobutyl chloroformate at 0° C., and the mixture was stirred at that temperature for 25 minutes. To it was added a mixture of 128 mg of sodium methanesulphonylamide and 0.233 ml of hexamethylphosphoramide at room temperature, and the mixture was stirred at ambient temperature for 20 hours. The reaction mixture was acidified to pH 4–5 with dilute hydrochloric acid, extracted with ethyl acetate, the extract washed with water, and a saturated aqueous solution of sodium chloride, dried over magnesium sulphate and concentrated under reduced pressure. The residue was purified by column chromatography on silica gel using a 5% v/v solution of methanol in ethyl acetate as eluent to give 75 mg of the title compound having the following physical characteristics.

TLC (ethyl acetate): RF=0.27;

IR: $\nu$=3380, 3250, 3040, 2945, 2860, 1720, 1450, 1410, 1380, 1340, 1250, 1155, 1125, 1080, 1050, 970 cm$^{-1}$;

NMR (acetone-d$_6$+CDCl$_3$ solution): $\delta$=5.85–5.25(2H,m), 4.41–2.98(7H,m), 3.24(3H,s), 0.89(3H,s);

MS: m/e=429, 411, 385, 321, 315, 295, 67, 55, 43.

EXAMPLE 9

(13E)-(6RS,9α,11α,15S)-6,9-Epithio-11,15-dihydroxyprost-13-enoic acid decyl ester An ethereal solution of diazodecane was added dropwise to a solution of 100 mg of (13E)-(6RS,9α,11α,15S)-6,9-epithio-11,15-dihydroxyprost-13-enoic acid (prepared as described in Example 2) in 5 ml of methylene chloride at room temperature with stirring until the starting material was not detected by thin layer chromatography on silica gel using a 2% v/v solution of methanol in ethyl acetate as developing solvent. The reaction mixture was concentrated under reduced pressure, and the residue was purified by column chromatography on silica gel using a mixture of cyclohexane and ethyl acetate (1:1) as eluent to give 109 mg of the title compound having the following physical characteristics:

TLC (methanol:ethyl acetate=1:49): Rf=0.61;

IR: $\nu$=3400, 2975, 2950, 2875, 1740, 1460, 1260, 1175, 1095, 1080, 970 cm$^{-1}$;

NMR: $\delta$=5.80–5.25(2H,m), 4.05(2H,t), 4.34–3.20(6H,m), 0.89(3H,t);

MS: m/e=492, 474, 448, 378, 193, 187.

EXAMPLE 10

(13E)-(6RS,9α,11α,15S)-6,9-Epithio-11,15-dihydroxyprost-13-enoic acid 2-hydroxyethyl ester A mixture of 70 mg of (13E)-(6RS,9α,11α,15S)-6,9-epithio-11,15-dihydroxyprost-13-enoic acid (prepared as described in Example 2), 3 ml of tetrahydrofuran and 34.5 μl of triethylamine was stirred at room temperature for 5 minutes, and then stirred with 27.7 μl of pivaloyl chloride. To the mixture were added 70 μl of triethylamine and 0.5 ml of 2-hydroxyethanol, and the mixture was stirred at room temperature for 18 hours. The reaction mixture was diluted with ethyl acetate, washed with water, and a saturated aqueous solution of sodium chloride, dried over magnesium sulphate and concentrated under reduced pressure. The residue was purified by column chromatography on silica gel using a mixture of ethyl acetate and cyclohexane (2:1) as eluent to give 92 mg of the title compound having the following physical characteristics:

TLC (methanol:ethyl acetate=1:49): Rf=0.35;

IR: $\nu$=3375, 2970, 2950, 2875, 1740, 1450, 1440, 1420, 1385, 1265, 1180, 1100, 970 cm$^{-1}$;

NMR: $\delta$=5.80–5.12(2H,m), 4.65–3.19(8H,m), 0.88(3H,t);

MS: m/e=396, 378, 353, 282, 236, 99.

The following compounds were prepared from the corresponding alcohols by the procedure described above.

(A) (13E)-(6RS,9α,11α,15S)-6,9-Epithio-11,15-dihydroxyprost-13-enoic acid 4-ethylphenyl ester from 4-ethylphenol.

TLC (ethyl acetate): Rf=0.57;

IR: $\nu$=3375, 2970, 2940, 2860, 1750, 1510, 1460, 1200, 965, 750 cm$^{-1}$;

NMR: $\delta$=7.18(2H,d), 6.96(2H,d), 5.80–5.27(2H,m), 4.42–3.20(4H,m), 0.88(3H,t);

MS: m/e=456, 438, 353, 335, 317, 122, 107, 43.

(B) (13E)-(6RS,9α,11α,15S)-6,9-Epithio-11,15-dihydroxyprost-13-enoic acid 4-benzoylaminophenyl ester from 4-benzoylaminophenol.

TLC (ethyl acetate): Rf=0.54;

IR: $\nu$=3350, 2945, 2860, 1760, 1660, 1530, 1510, 1410, 1320, 1200, 970 cm$^{-1}$;

NMR (acetone-d$_6$+dimethyl sulphoxide-d$_6$ solution): $\delta$=8.22–7.72(4H,m), 7.72–7.25(3H,m), 7.19(2H,d), 5.75–5.24(2H,m), 0.88(3H,t);

MS: m/e=547, 529, 503, 352, 335, 317, 213, 105, 77.

(C) (13E)-(6RS,9α,11α,15S)-6,9-Epithio-11,15-dihydroxyprost-13-enoic acid 4-methylthiophenyl ester from 4-methylthiophenol.

TLC (ethyl acetate): Rf=0.56;

IR: $\nu$=3375, 2950, 1760, 1490, 1205, 1170, 1130, 1090, 970, 760 cm$^{-1}$;

NMR: $\delta$=7.27(2H,d), 7.00(2H,d), 5.80–5.25(2H,m), 4.45–3.25(4H,m), 2.47(3H,s), 0.89(3H,t);

MS: m/e=492, 474, 456, 353, 335, 317, 140, 125, 99, 43.

(D) (13E)-(6RS,9α,11α,15S)-6,9-Epithio-11,15-dihydroxyprost-13-enoic acid 2,3-dihydroxypropyl ester from glycerol.

TLC (ethyl acetate): RF=0.16;

IR: $\nu$=3350, 2940, 2860, 1735, 1450, 1175, 1050, 965, 750 cm$^{-1}$;

NMR(acetone-d$_6$+CDCl$_3$ solution): $\delta$=5.85–5.20(2H,m), 4.50–2.95(13H,m), 0.89(3H,t);

MS: m/e=426, 408, 382, 353, 335, 312, 149, 99, 67, 55, 43.

(E) (13E)-(6RS,9α,11α,15S)-6,9-Epithio-11,15-dihydroxyprost-13-enoic acid 2-ethylthioethyl ester from 2-ethylthioethanol.

TLC (ethyl acetate): Rf=0.50;

IR: $\nu$=3400, 2945, 2860, 1740, 1450, 1380, 1265, 1170, 1085, 970 cm$^{-1}$;

NMR: $\delta$=5.80–5.15(2H,m), 4.23(2H,t), 4.55–3.15(4H,m), 2.75(2H,t), 2.60(2H,q), 3.15–2.15(6H,m), 1.27(3H,t), 0.89(3H,t);

MS: m/e=440, 422, 396, 352, 238, 149, 89, 61, 43.

(F) (13E)-(6RS,9α,11α,15S)-6,9-Epithio-11,15-dihydroxyprost-13-enoic acid furfuryl ester from furfuryl alcohol.

TLC (ethyl acetate): Rf=0.51;

IR: $\nu$=3400, 2950, 2875, 1740, 1500, 1450, 1380, 1155, 970, 760 cm$^{-1}$;

NMR: $\delta$7.53–7.34(1H,m), 6.55–6.20(2H,m), 5.80–5.27(2H,m), 5.07(2H, broad s), 4.42–3.19(4H,m), 0.89(3H,t);

MS: m/e=450, 432, 414, 379, 351, 333, 235, 99, 81, 71, 43.

(G) (13E)-(6RS,9α,11α,15S)-6,9-Epithio-11,15-dihydroxyprost-13-enoic acid tetrahydrofurfuryl ester from tetrahydrofurfuryl alcohol.

TLC (ethyl acetate): Rf=0.40;

IR: $\nu=3400, 2975, 2950, 2875, 1740, 1460, 1250, 1180, 1085, 1020, 970, 745$ cm$^{-1}$;

NMR: $\delta=5.75$–$5.25$(2H,m), 4.64–3.10(9H,m), 0.89(3H,t);

MS: m/e=436, 418, 392, 352, 334, 322, 263, 238, 99, 85, 71, 43.

(H) (13E)-(6RS,9α,11α,15S)-6,9-Epithio-11,15-dihydroxyprost-13-enoic acid phthalid-3-yl ester from 3-hydroxyphthalide.

TLC (ethyl acetate): Rf=0.50
MS: m/e=352, 334, 308, 238, 154, 149, 105, 99.

EXAMPLE 11

(13E)-(6RS,9α,11α,15S)-6,9-Epithio-11,15-dihydroxyprost-13-enoic acid 4-semicarbazonotolyl ester To a solution of 98 mg of (13E)-(6RS,9α,11α,15S)-6,9-epithio-11,15-dihydroxyprost-13-enoic acid (prepared as described in Example 2) and 52 μl of triethylamine in 3 ml of acetone was added 49 μl of isobutyl chloroformate at 0° C., and the mixture was stirred at 0° C. for 30 minutes. To it were added 1.4 ml of pyridine and 202 mg of 4-hydroxybenzaldehyde semicarbazone at ambient temperature, and the mixture was stirred at room temperature for 5 hours. The reaction mixture was concentrated under reduced pressure. The residue was purified by recrystallization from acetonitrile to give 29.5 mg of the title compound having the following physical characteristics: melting point: 90°–91° C.;

TLC (chloroform:tetrahydrofuran:acetic acid=10:2:1):
Rf=0.20;

IR(KBr tablet): $\nu=3475, 2950, 2870, 1760, 1680, 1580, 1190, 970$ cm$^{-1}$;

NMR(acetone-d$_6$+CDCl$_3$ solution): $\delta=9.75$(1H, broad s), 7.90(1H, broad s), 7.66(2H,d), 7.10(2H,d) 6.02(2H, broad s), 5.70–5.25(2H,m), 4.30–3.08(6H,m);

MS: m/e=469, 452, 424, 352, 334, 251, 240, 147, 65.

EXAMPLE 12

(13E)-(6RS,9α,11α,15S)-6,9-Epithio-11,15-dihydroxyprost-13-enoic acid 1,3-bisstearoyloxy-2-propyl ester Under an atmosphere of nitrogen, a mixture of 51 mg of (13E)-(6RS,9α,11α,15S)-6,9-epithio-11,15-bis-(tetrahydropyran-2-yloxy)prost-13-enoic acid 1,3-bis-stearoyloxy-2-propyl ester, 2.5 mg of p-toluenesulphonic acid-pyridine complex and 2 ml of methanol was stirred at 50° C. for 1.5 hours, and then concentrated under reduced pressure. The residue was purified by column chromatography on silica gel using a mixture of cyclohexane and ethyl acetate (2:1) as eluent to give 29 mg of the title compound having the following physical characteristics:

TLC (cyclohexane:ethyl acetate=1:1): Rf=0.49;
IR(CCl$_4$ solution): $\nu=2950, 2850, 1745, 1460, 1160$ cm$^{-1}$;

NMR(CCl$_4$ solution): $\delta=5.70$–4.80(3H,m), 4.50–3.00(10H,m), 2.70–0.70(95H,m);

MS: m/e=846, 692, 674, 648, 606.

(13E)-(6RS,9α,11α,15S)-6,9-Epithio-11,15-bis(tetrahydropyran-2-yloxy)prost-13-enoic acid 1,3-bis-stearoyloxy-2-propyl ester, used as a starting material, was prepared as follows.

Under an atmosphere of nitrogen, a mixture of 2.0 g of glycerol, 13.0 g of stearoyl chloride, 35 ml of pyridine and 70 ml of chloroform was stirred at room temperature for 3 hours, and then concentrated under reduced pressure. The residue was dissolved in chloroform, washed with water, and a saturated aqueous solution of sodium chloride, dried over sodium sulphate and concentrated under reduced pressure. The residue was recrystallized from acetone to give 3.548 g of 1,3-bis-stearoyloxy-2-propanol having the following physical characteristics:

m.p.=78.5°–79° C.
TLC (chloroform:ethyl acetate=10:1): Rf=0.67;
IR(KBr tablet): $\nu=3450, 2925, 1740, 1200$ cm$^{-1}$;
NMR: $\delta=4.1$(5H, broad s), 2.7–2.0(5H,m), 2.0–0.6(66H,m);
MS: m/e=606, 593, 578.

Under an atmosphere of nitrogen, a mixture of 122 mg of (13E)-(6RS,9α,11α,15S)-6,9-epithio-11,15-bis(tetrahydropyran-2-yloxy)prost-13-enoic acid [prepared from (13E)-(6RS,9α,11α,15S)-6,9-epithio-11,15-dihydroxyprost-13-enoic acid (prepared as described in Example 2) by the tetrahydropyran-2-ylation procedure described in Reference Example 1], 143 mg of 1,3-bis-stearoyloxy-2-propanol, prepared as described above, 75 mg of dipyridyl disulphide, 90 mg of triphenylphosphine and 3 ml of xylene was stirred at room temperature for 2 hours, then at 40° C. for 2 hours, and at 80° C. overnight. The reaction mixture was poured into water, extracted with ethyl acetate, the extract was washed with water, and a threaded aqueous solution of sodium chloride, dried over magnesium sulphate and concentrated under reduced pressure. The residue was purified by column chromatography on silica gel using a mixture of cyclohexane and ethyl acetate (8:1) as eluent to give 51 mg of (13E)-(6RS,9α,11α,15S)-6,9-epithio-11,15-bis(tetrahydropyran-2-yloxy)prost-13-enoic acid 1,3-bisstearoyloxy-2-propyl ester having the following physical characteristic:

MS: m/e=675, 606.

EXAMPLE 13

α-Cyclodextrin clathrate of (13E)-(6RS,9α,11α,15S)-6,9-epithio-11,15-dihydroxyprost-13-enoic acid methyl ester A solution of 6.3 mg of (13E)-(6RS,9α,11α,15S)-6,9-epithio-11,15-dihydroxyprost-13-enoic acid methyl ester [prepared as described in Example 1(G)] in 0.5 ml of ethanol was added to a solution of 212.6 mg of α-cyclodextrin in 1.5 ml of a 1% v/v solution of triethylamine in water, and the mixture was stirred at room temperature for one minute. The reaction mixture was concentrated under reduced pressure to give 217 mg of the α-cyclodextrin clathrate of the compound specified in the title. The content of the compound in the cyclodextrin clathrate was 2.9% w/w.

EXAMPLE 14

β-Cyclodextrin clathrate of (13E)-(6RS,9α,11α,15S)-6,9-epithio-11,15-dihydroxyprost-13-enoic acid methyl ester A solution of 6.4 mg of (13E)-(6RS,9α,11α,15S)-6,9-epithio-11,15-dihydroxyprost-13-enoic acid methyl ester [prepared as described in Example 1(G)] in 0.5 ml of ethanol was added to a solution of 93.6 mg of β-cyclodextrin in 3.5 ml of a 1% v/v solution of triethylamine in water, and the mixture was stirred at room temperature for one minute. The reaction mixture was concentrated under reduced pressure to give 89.8 mg of the β-cyclodextrin clathrate of the compound specified in the title. The content of the compound in the cyclodextrin clathrate was 7.1% w/w.

By proceeding as described in Examples 13 and 14, but replacing the (13E)-(6RS,9α,11α,15S)-6,9-epithio-11,15-dihydroxyprost-13-enoic acid methyl ester by (13E)-(6RS,9α,11α,15R)-6,9-epithio-11,15-dihydroxy-15-(1-butylcyclobutyl)-16,17,18,19,20-pentanorprost-13-enoic acid methyl ester, (13E)-(6RS,9α,11α,15R)-6,9-epithio-11,15-dihydroxy-16,16-dimethylprost-13-enoic acid methyl ester and (13E)-(6RS,9α,11α,15S,16S)-6,9-epithio-11,15-dihydroxy-16-methylprost-13-enoic acid methyl ester, there were obtained the α- and β-cyclodextrin clathrates thereof.

The present invention includes within its scope pharmaceutical compositions which comprise at least one new therapeutically useful compound of general formula V, or cyclodextrin clathrate, non-toxic salt or non-toxic acid addition salt thereof, together with a pharmaceutical carrier or coating. In clinical practice, the new compounds of the present invention will normally be administered orally, vaginally, rectally or parenterally.

Solid compositions for oral administration include compressed tablets, pills, dispersible powders and granules. In such solid compositions one or more of the active compounds is, or are, admixed with at least one inert diluent such as calcium carbonate, potato starch, dextrin, alginic acid, lactose, mannitol, glucose or cacao butter. The compositions may also comprise, as is normal practice, additional substances other than inert diluents, e.g. lubricating agents such as magnesium stearate. The tablets or pills may, if desired, be coated and made into sugar-coated, gelatin-coated, enteric-coated or film-coated tablets or pills, or tablets or pills coated with two or more layers.

Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants such as wetting and suspending agents, and sweetening, flavouring, perfuming and preserving agents.

The compositions according to the invention for oral administration, also include capsules of absorbable material such as gelatin containing one or more of the active substances with or without the addition of diluents or excipients.

Solid compositions for intrarectal administration include suppositories formulated in manner known per se and containing one or more of the active compounds.

Solid or ointment compositions for vaginal administration include pessaries, silicone rubber pessaries and ointments formulated in manner known per se and containing one or more of the active compounds with one or more carriers, diluents or supports such as cacao butter, macrosol, Witepsol (registered trade mark), silicone rubber or vaseline.

Preparations according to the invention for parenteral administration include sterile aqueous or non-aqueous solutions, suspensions or emulsions. Examples of non-aqueous solvents or suspending media are propylene glycol, polyethylene glycol, ethanol, vegetable oils such as olive oil, and injectable organic esters such as ethyl oleate and sorbitan esters. These compositions may also include adjuvants such as preserving, wetting, emulsifying and dispersing agents. They may be sterilised, for example by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active subtance when required for administration by injection; for oral administration the preparations will normally contain at least 0.1% by weight of active substance.

The dosage employed depends upon the desired therapeutic effect, the route of administration, the duration of the treatment, and the age and body weight of the patient.

In the human adult female, each dose per person is generally from 5 μg to 5 mg by oral, intravaginal, intrarectal, intrauterine, intravenous, intramuscular or extraamniotic, preferably oral or intravaginal, administration in treatment for the control of oestrus, contraception and menstrual regulation in females, and the termination of pregnancy and the induction of labour in pregnant females. The dosage will normally be administered once or several times per day. The preferred dose per person is from 0.2 to 1.5 mg by oral or intravaginal administration.

The following Examples illustrate pharmaceutical compositions according to the present invention.

EXAMPLE 15

(13E)-(6RS,9α,11α,15S)-6,9-Epithio-11,15-dihydroxyprost-13-enoic acid methyl ester (2 mg) was dissolved in ethanol (10 ml), mixed with mannitol (18.5 g), sieved through a 30-mesh sieve, dried at 30° C. for 90 minutes and again sieved through a 30-mesh sieve. Microfine silica (e.g. "Aerosil", a registered Trade Mark, 200 mg) was added and the powder obtained was machine-filled into one hundred No. 2 hard gelatin capsules to give capsules each containing 20 μg of (13E)-(6RS,9α,11α,15S)-6,9-epithio-11,15-dihydroxyprost-13-enoic acid methyl ester which after swallowing of the capsule is released into the stomach.

EXAMPLE 16

By proceeding as described in Example 15, but replacing the (13E)-(6RS,9α,11α,15S)-6,9-epithio-11,15-dihydroxyprost-13-enoic acid methyl ester by (13E)-(6RS,9α,11α,15R)-6,9-epithio-11,15-dihydroxy-15-(1-butylcyclobutyl)-16,17,18,19,20-pentanorprost-13-enoic acid methyl ester, (13E)-(6RS,9α,11α,15R)-6,9-epithio-11,15-dihydroxy-16,16-dimethylprost-13-enoic acid methyl ester, or (13E)-(6RS,9α,11α,15S,16S)-6,9-epithio-11,15-dihydroxy-16-methylprost-13-enoic acid methyl ester, there were obtained capsules each containing 20 μg of these compounds.

EXAMPLE 17

One thousand tablets for oral administration were prepared from the following compounds in manner known per se, each tablet containing 0.5 mg of the active substance.

| | |
|---|---|
| (13E)-(6RS,9α,11α,15S)-6,9-epithio-11,15-dihydroxyprost-13-enoic acid methyl ester | 500 mg |

| | |
|---|---|
| calcium carboxymethylcellulose | 2 g |
| silicon dioxide | 0.2 g |
| magnesium stearate | 2 g |
| mannitol | 95.3 g |

By proceeding as described above, but replacing the (13E)-(6RS,9α,11α,15S)-6,9-epithio-11,15-dihydroxyprost-13-enoic acid methyl ester by 250 mg of (13E)-(6RS,9α,11α,15R)-6,9-epithio-11,15-dihydroxy-15-(1-butylcyclobutyl)-16,17,18,19,20-pentanorprost-13-enoic acid methyl ester, (13E)-(6RS,9α,11α,15R)-6,9-epithio-11,15-dihydroxy-16,16-dimethylprost-13-enoic acid methyl ester or (13E)-(6RS,9α,11α,15S,16S)-6,9-epithio-11,15-dihydroxy-16-methylprost-13-enoic acid methyl ester, there were obtained one thousand tablets for oral administration, each tablet containing 0.25 mg of the active substance.

EXAMPLE 18

One hundred buccal tablets for oral administration were prepared from the following compounds in manner known per se, each buccal tablet containing 0.5 mg of the active substance.

| | |
|---|---|
| (13E)-(6RS,9α,11α,15S)-6,9-epithio-11,15-dihydroxyprost-13-enoic acid methyl ester | 50 mg |
| silicon dioxide | 0.03 g |
| magnesium stearate | 0.1 g |
| dextrin | 9.82 g |

By proceeding as described above, but replacing the (13E)-(6RS,9α,11α,15S)-6,9-epithio-11,15-dihydroxyprost-13-enoic acid methyl ester by (13E)-(6RS,9α,11α,15R)-6,9-epithio-11,15-dihydroxy-15-(1-butylcyclobutyl)-16,17,18,19,20-pentanorprost-13-enoic acid methyl ester, (13E)-(6RS,9α,11α,15R)-6,9-epithio-11,15-dihydroxy-16,16-dimethylprost-13-enoic acid methyl ester or (13E)-(6RS,9α,11α,15S,16S)-6,9-epithio-11,15-dihydroxy-16-methylprost-13-enoic acid methyl ester, there were obtained one hundred buccal tablets for oral administration, each buccal tablet containing 0.5 mg of the active substance.

EXAMPLE 19

One hundred units of dispersible powder for oral administration were prepared from the following in manner known per se, each unit containing 0.5 mg of the active substance.

| | |
|---|---|
| (13E)-(6RS,9α,11α,15S)-6,9-epithio-11,15-dihydroxyprost-13-enoic acid methyl ester | 50 mg |
| lactose | 99.95 g |

EXAMPLE 20

One hundred capsules for oral administration were prepared from the following compounds using No. 3 gelatin capsules in manner known per se, each capsule containing 0.5 mg of the active substance.

| | |
|---|---|
| (13E)-(6RS,9α,11α,15S)-6,9-epithio-11,15-dihydroxyprost-13-enoic acid methyl ester | 50 mg |
| magnesium stearate | 0.23 g |
| lactose | 22.72 g |

By proceeding as described above, but replacing the (13E)-(6RS,9α,11α,15S)-6,9-epithio-11,15-dihydroxyprost-13-enoic acid methyl ester by 25 mg of (13E)-(6RS,9α,11α,15R)-6,9-epithio-11,15-dihydroxy-15-(1-butylcyclobutyl)-16,17,18,19,20-pentanorprost-13-enoic acid methyl ester, (13E)-(6RS,9α,11α,15R)-6,9-epithio-11,15-dihydroxy-16,16-dimethylprost-13-enoic acid methyl ester or (13E)-(6RS,9α,11α,15S,16S)-6,9-epithio-11,15-dihydroxy-16-methylprost-13-enoic acid methyl ester, there were obtained one hundred capsules, each capsule containing 0.25 mg of the active substance.

EXAMPLE 21

One hundred pessaries for vaginal administration were prepared from the following compounds in manner known per se, each pessary containing 1 mg of the active substance.

| | |
|---|---|
| (13E)-(6RS,9α,11α,15S)-6,9-epithio-11,15-dihydroxyprost-13-enoic acid methyl ester | 100 mg |
| ethanol | 2 ml |
| Witepsol S-52 | 80 g |

By proceeding as described above, but using 20 mg instead of 100 mg of (13E)-(6RS,9α,11α,15S)-6,9-epithio-11,15-dihydroxyprost-13-enoic acid methyl ester there were obtained one hundred pessaries, each pessary containing 0.2 mg of the active compound.

One hundred pessaries were prepared from 50 mg of (13E)-(6RS,9α,11α,15R)-6,9-epithio-11,15-dihydroxy-15-(1-butylcyclobutyl)-16,17,18,19,20-pentanorprost-13-enoic acid methyl ester, (13E)-(6RS,9α,11α,15R)-6,9-epithio-11,15-dihydroxy-16,16-dimethylprost-13-enoic acid methyl ester or (13E)-(6RS,9α,11α,15S,16S)-6,9-epithio-11,15-dihydroxy-16-methylprost-13-enoic acid methylester by the procedure described above, each pessary containing 0.5 mg of the active substance.

EXAMPLE 22

Fifty silicone rubber pessaries for vaginal administration were obtained from the following compounds using 100 sheets of silicone rubber (10 cm² area and 0.25 mm thick) and gelatin (used as a jointing material) in manner known per se, each silicone rubber pessary containing 1 mg of the active substance.

| | |
|---|---|
| (13E)-(6RS,9α,11α,15S)-6,9-epithio-11,15-dihydroxyprost-13-enoic acid methyl ester | 50 mg |
| ethanol | 10 ml |

The following Clinical Examples illustrate the use of the compounds according to the invention.

CLINICAL EXAMPLE 1

One pessary containing 0.2 mg of (13E)-(6RS,9α,11α,15S)-6,9-epithio-11,15-dihydroxyprost-13-enoic acid methyl ester (prepared as described in Example 21) was administered vaginally one to three times at one- to three-hour intervals to five women aged from twenty to forty years in the expired stage of pregnancy. The induction of labour was confirmed in all the cases.

CLINICAL EXAMPLE 2

One pessary containing 1 mg of (13E)-(6RS,9α,11α,15S)-6,9-epithio-11,15-dihydroxyprost-13-enoic acid methyl ester (prepared as described in Example 21) was administered vaginally one to five times at one- to three-hour intervals to fifteen women aged from twenty to forty years two or three days before the expected date of menstruation. The beginning of menstruation was confirmed in all the cases.

CLINICAL EXAMPLE 3

One pessary containing 0.5 mg of (13E)-(6RS,9α,11α,15R)-6,9-epithio-11,15-dihydroxy-16,16-dimethyl-prost-13-enoic acid methyl ester (prepared as described in Example 21) was administered vaginally one to three times at one- to three-hour intervals to three women aged twenty or twenty-one years two or three days before the expected date of menstruation. The beginning of menstruation was confirmed in all the cases.

CLINICAL EXAMPLE 4

One to three tablets containing 0.5 mg of (13E)-(6RS,9α,11α,15S)-6,9-epithio-11,15-dihydroxyprost-13-enoic acid methyl ester (prepared as described in Example 17) were administered orally to five women aged from twenty to twenty-two years two or three days before the expected date of menstruation. The beginning of menstruation was confirmed in all the cases.

CLINICAL EXAMPLE 5

One pessary containing 1 mg of (13E)-(6RS,9α,11α,15S)-6,9-epithio-11,15-dihydroxyprost-13-enoic acid methyl ester (prepared as described in Example 21) was administered vaginally two to five times at one- to three-hour intervals to fifteen women aged from twenty to forty years in the early stages of pregnancy. The termination of pregnancy was confirmed in all the cases.

CLINICAL EXAMPLE 6

One to three tablets containing 0.25 mg of (13E)-(6RS,9α,11α,15R)-6,9-epithio-11,15-dihydroxy-16,16-dimethylprost-13-enoic acid methyl ester (prepared as described in Example 17) were administered orally one to five times to seven women aged from twenty-five to thirty years in the early stages of pregnancy. The termination of pregnancy was confirmed in all the cases.

We claim:

1. Method for the termination of pregnancy and the induction of labour in pregnant human females and for the control of oestrus, contraception or menstrual regulation in human females which comprises administering to the human female an effective amount of a compound of the formula:

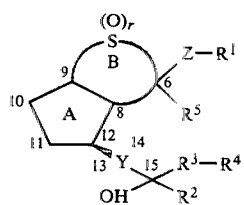

wherein the ring A represents a grouping of the formula:

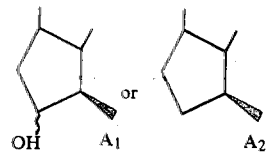

(wherein the wavy line represents α- or β-configuration, or mixtures thereof), the ring B represents a grouping of the formula:

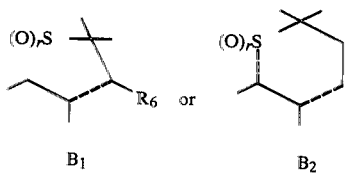

(wherein $R^6$ represents a hydrogen atom or a methyl or ethyl group, and r is zero, one or two), Y represents an ethylene group, or a cis- or trans-vinylene group, Z represents a grouping of the formula:

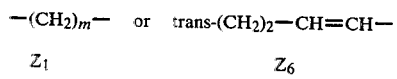

(wherein m is 3, 4 or 5) $R^1$ represents a grouping of the formula:

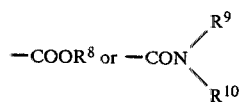

(wherein $R^8$ represents
 (1) a hydrogen atom,
 (2) an alkyl group containing from 1 to 12 carbon atoms,
 (3) an aralkyl group containing from 7 to 13 carbon atoms,
 (4) a cycloalkyl group containing from 4 to 7 carbon atoms unsubstituted or substituted by at least one alkyl group containing from 1 to 4 carbon atoms,
 (5) a phenyl group unsubstituted or substituted by at least one halogen atom, trifluoromethyl group, alkyl, alkoxy or alkylthio group containing from 1 to 4 carbon atoms, or by a phenyl group,
 (6) a naphthyl group,
 (7) a 2,3- or 1,3-dihydroxypropyl group,
 (8) a 2,3- or 1,3-bisalkanoyloxypropyl group,
 (9) a grouping of the formula:

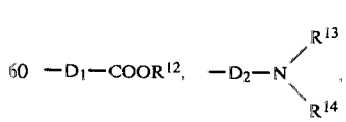

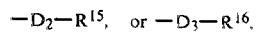

wherein $D_1$ represents an alkylene group containing from 1 to 12 carbon atoms, $D_2$ represents an alkylene group containing from 2 to 12 carbon atoms, $D_3$ represents a single bond, or an alkylene group containing from 1 to 12 carbon atoms, $R^{12}$, $R^{13}$ and $R^{14}$, which may be the same or different, each represent an alkyl group containing from 1 to 4 carbon atoms, $R^{15}$ represents a hydroxy group or an alkoxy or alkylthio group containing from 1 to 4 carbon atoms, and $R^{16}$ represents a furyl, tetrahydrofuryl, 3-phthalidyl, pyridyl or thienyl ring, or (10) a grouping of the formula:

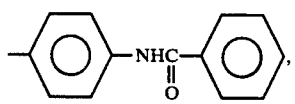

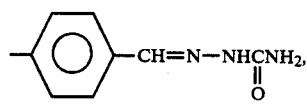

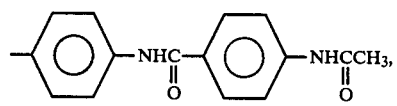

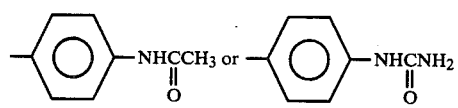

and $R^9$ and $R^{10}$, which may be the same or different, each represent a hydrogen atom, an alkyl group containing from 1 to 12 carbon atoms, an alkylsulphonyl group containing from 1 to 4 carbon atoms, an alkanoyl group containing from 2 to 5 carbon atoms, or

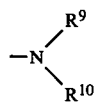

represents a pyrrolidyl, piperidino, morpholino, hexamethyleneiminyl or piperazinyl ring), $R^2$ represents a hydrogen atom, or a methyl or ethyl group, $R^3$ represents a single bond or an alkylene group containing from 1 to 5 carbon atoms, $R^4$ represents a hydrogen atom, an alkyl or alkoxy group containing from 1 to 8 carbon atoms, a cycloalkyl or cycloalkyloxy group containing from 4 to 7 carbon atoms unsubstituted or substituted by at least one alkyl group containing from 1 to 8 carbon atoms, or represents a phenyl or phenoxy group unsubstituted or substituted by at least one halogen atom, trifluoromethyl group, or alkyl group containing from 1 to 4 carbon atoms, with the proviso that, when $R^3$ represents a single bond, $R^4$ does not represent an alkoxy, cycloalkyloxy or phenoxy group, $R^5$ represents a hydrogen atom, or a methyl or ethyl group, the absolute configuration of $C_6$ and $C_{15}$, which may be the same or different, is R or S, or mixtures thereof, i.e. RS, and with the proviso that, when one of the groups $R^5$, $R^6$ and $R^7$ represents a methyl or ethyl group the other two groups are hydrogen atoms, or of a cyclodextrin clathrate thereof or, when the compound of general formula V contains a carboxy group, of a non-toxic salt thereof or, when the compound of general formula V contains an amino group, of a non-toxic acid addition salt thereof.

2. Method according to claim 1 in which the compound of general formula V is (13E)-(6RS,9α,11α,15S)-6,9-epithio-11,15-dihydroxyprost-13-enoic acid methyl ester or (13E)-(6RS,9α,11α,15R)-6,9-epithio-11,15-dihydroxy-16,16-dimethylprost-13-enoic acid methyl ester.

3. Method according to claim 1 or 2 in which the dose per person is from 5 μg to 5 mg by oral, intravaginal, intrarectal, intrauterine, intravenous, intramuscular or extra-amniotic administration.

4. Method according to claim 1 or 2 in which the dose per person is from 0.2 to 1.5 mg by oral or intravaginal administration.

5. (13E)-(6RS,9α,11α,15R)-6,9-Epithio-11,15-dihydroxy-15-(1-butylcyclobutyl)-16,17,18,19,20-pentanorprost-13-enoic acid methyl ester or a cyclodextrin clathrate thereof.

6. (13E)-(6RS,9α,11α,15R)-6,9-Epithio-11,15-dihydroxy-16,16-dimethylprost-13-enoic acid methyl ester or a cyclodextrin clathrate thereof.

7. (13E)-(6RS,9α,11α,15R)-6,9-Epithio-11,15-dihydroxy-16-(4-chlorophenoxy)-17,18,19,20-tetranorprost-13-enoic acid methyl ester or a cyclodextrin clathrate thereof.

8. (13E)-(6RS,9α,11α,15S)-6,9-Epithio-15-hydroxyprost-13-enoic acid methyl ester or a cyclodextrin clathrate thereof.

9. (13E)-(6RS,9α,11α,15S)-N-Methanesulphonyl-6,9-epithio-11,15-dihydroxyprost-13-en-1-amide or a cyclodextrin clathrate thereof.

* * * * *